United States Patent
Kass et al.

(10) Patent No.: US 10,525,269 B2
(45) Date of Patent: Jan. 7, 2020

(54) METHODS FOR IMPROVING HEART FUNCTION

(71) Applicant: THE JOHNS HOPKINS UNIVERSITY, Baltimore, MD (US)

(72) Inventors: David Kass, Columbia, MD (US); Gordon Tomaselli, Lutherville, MD (US); Jonathan Kirk, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 186 days.

(21) Appl. No.: 15/359,041

(22) Filed: Nov. 22, 2016

(65) Prior Publication Data

US 2017/0182321 A1 Jun. 29, 2017

Related U.S. Application Data

(62) Division of application No. 13/884,144, filed as application No. PCT/US2011/059787 on Nov. 8, 2011, now Pat. No. 9,539,427.

(60) Provisional application No. 61/411,218, filed on Nov. 8, 2010.

(51) Int. Cl.
| | |
|---|---|
| *A61N 1/362* | (2006.01) |
| *A61N 1/368* | (2006.01) |
| *A61N 1/365* | (2006.01) |
| *C12Q 1/6876* | (2018.01) |
| *G01N 27/447* | (2006.01) |

(52) U.S. Cl.
CPC ............ *A61N 1/3627* (2013.01); *A61N 1/365* (2013.01); *A61N 1/3682* (2013.01); *A61N 1/3684* (2013.01); *A61N 1/3688* (2013.01); *A61N 1/36507* (2013.01); *C12Q 1/6876* (2013.01); *G01N 27/447* (2013.01)

(58) Field of Classification Search
CPC ................ A61N 1/3627; A61N 1/3682–36843
See application file for complete search history.

(56) References Cited

U.S. PATENT DOCUMENTS

| | | | |
|---|---|---|---|
| 4,405,712 A | 9/1983 | Vande Woude et al. | |
| 4,777,127 A | 10/1988 | Suni et al. | |
| 4,816,567 A | 3/1989 | Cabilly et al. | |
| 4,843,155 A | 6/1989 | Chomczynski | |
| 4,861,719 A | 8/1989 | Miller | |
| 4,873,316 A | 10/1989 | Meade et al. | |
| 4,980,289 A | 12/1990 | Temin et al. | |

(Continued)

FOREIGN PATENT DOCUMENTS

| | | |
|---|---|---|
| EP | 0125023 A1 | 11/1984 |
| EP | 0171496 A2 | 2/1986 |

(Continued)

OTHER PUBLICATIONS

Cleland, J et al Longer-term effects of cardiac resynchronization therapy on mortality in heart failure [the cardiac resynchronization-heart failure (care-hf) trial extension phase]. Eur Heart J. 2006,17:1928-1932.

(Continued)

*Primary Examiner* — Michael W Kahelin
(74) *Attorney, Agent, or Firm* — MH2 Technology Law Group LLP

(57) ABSTRACT

The invention provides methods related to improving heart function.

16 Claims, 20 Drawing Sheets

Specification includes a Sequence Listing.

(56) References Cited

U.S. PATENT DOCUMENTS

| | | | |
|---|---|---|---|
| 5,219,740 | A | 6/1993 | Miller et al. |
| 5,225,539 | A | 7/1993 | Winter |
| 5,328,470 | A | 7/1994 | Nabel et al. |
| 5,580,859 | A | 12/1996 | Felgner et al. |
| 5,604,251 | A | 2/1997 | Heitsch et al. |
| 5,631,236 | A | 5/1997 | Woo et al. |
| 5,679,847 | A | 10/1997 | Ohkoshi et al. |
| 5,834,306 | A | 11/1998 | Webster et al. |
| 6,174,530 | B1 | 1/2001 | Rose et al. |
| 6,184,344 | B1 | 2/2001 | Kent et al. |
| 6,282,447 | B1 | 8/2001 | Cook et al. |
| 6,973,349 | B2 | 12/2005 | Salo |
| 7,078,510 | B2 | 7/2006 | Robbins |
| 7,130,683 | B2 | 10/2006 | Casavant et al. |
| 2002/0169484 | A1 | 11/2002 | Mathis et al. |
| 2003/0144703 | A1* | 7/2003 | Yu ............ A61N 1/056 607/17 |
| 2005/0137631 | A1* | 6/2005 | Yu ............ A61N 1/365 607/9 |
| 2005/0181386 | A1 | 8/2005 | Diamond et al. |
| 2005/0222640 | A1* | 10/2005 | Schwartz ...... A61N 1/3627 607/44 |
| 2006/0094038 | A1 | 5/2006 | Wagner et al. |
| 2006/0275770 | A1 | 12/2006 | Bednarik |
| 2008/0086174 | A1 | 4/2008 | Libbus et al. |
| 2009/0082823 | A1 | 3/2009 | Shuros et al. |
| 2009/0234416 | A1* | 9/2009 | Zielinski ...... A61N 1/3627 607/25 |
| 2016/0262635 | A1* | 9/2016 | McCullouch ...... G16H 50/50 |

FOREIGN PATENT DOCUMENTS

| | | |
|---|---|---|
| EP | 0173494 A2 | 3/1986 |
| EP | 0184187 A2 | 6/1986 |
| EP | 0264166 A1 | 4/1988 |
| EP | 0345242 A2 | 12/1989 |
| EP | 0415731 A2 | 3/1991 |
| GB | 2200651 A | 8/1988 |
| WO | 1986001533 A1 | 3/1986 |
| WO | 1987002671 A1 | 5/1987 |
| WO | 1989002468 A1 | 3/1989 |
| WO | 1989005349 A1 | 6/1989 |
| WO | 1990002806 A1 | 3/1990 |
| WO | 1990007936 A1 | 7/1990 |
| WO | 1990011092 A1 | 10/1990 |
| WO | 1991002805 A2 | 3/1991 |
| WO | 1993010218 A1 | 5/1993 |
| WO | 1993011230 A1 | 6/1993 |
| WO | 1993025234 A1 | 12/1993 |
| WO | 1993025698 A1 | 12/1993 |
| WO | 1994003622 A1 | 2/1994 |
| WO | 1998033791 A1 | 8/1998 |
| WO | 1999031241 A1 | 6/1999 |
| WO | 2000008191 A2 | 2/2000 |

OTHER PUBLICATIONS

Cleland, J et al. The effect of cardiac resynchronization on morbidity and mortality in heart failure. N Engl. J. Med.352, 1439-1549 (2005).

Lloyd-Jones, D. et al. Executive summary:Heart disease and stroke statistics—2010 update: A report from the American HeartAssociation. Circulation 121, 948-954 (2010).

Bristow, M. et al Comparison of Medical Therapy, Pacing, and Defibrillation in Heart Failure (Companion) Investigators, Cardiac resynchronization therapy with or without an implantable defibrillator in advanced chronic heart failure. N. Engl. J. Med. 350, 2140-2150 (2004).

Abraham, W. et al. Multicenter InSync Randomized Clinical Evaluation, Cardiac resynchronization in chronic heart failure. N. Engl. J. Med. 346, 1845-1852 (2002).

Kass, D et al Nevo, Improved left ventricular mechanics from acute VDD pacing in patients with dilated cardiomyopathy and ventricular conduction delay. Circulation 99, 1567-1573 (1999).

Sutton, J. et al. Cardiac resynchronization induces major structural and functional reverse remodeling in patients with New York Heart Association class I/II heart failure. Circulation 120, 1858-1865 (2009).

Chakir, K. et al. Mechanisms of enhanced b-adrenergic reserve from cardiac resynchronization therapy. Circulation 119, 1231-1240 (2009).

Ward, S. et al. Binding activities of a repertoire of single immunoglobulin variable domains secreted from Escherichai coli (1989) Nature 341: 544-546.

Bird, R. et al. Single-chain antigen-binding proteins. (1989) Science 242:423-426.

Huston et al. Protein engineering of antibody binding sites: recovery of specific activity in an anti-digoxin single-chain Fv analogue produced in Escherichia coli (1988) Proc Natl Acad Sci USA 85: 5879-5883.

Osbourn, J. et al. Directed selection of MIP-1alpha neutralizing CCR5 antibodies from a phage display human antibody library (1998) Nat Biotech 16: 778.

Hollinger et al. "Diabodies": small bivalent and bispecific antibody fragments. (1993) PNA USA 90:6444-6448.

Poljak et al. Production and structure of diabodies. (1994) Structure 2: 1121-1123.

Kipriyanov et al. Single-chain antibody streptavidin fusions: tetrameric bifunctional scFv-complexes with biotin binding activity and enhanced affinity to anitgen. (1995) Human antibodies and hybridomas 6:93-101.

Kipriyanov et al. Recombinant single-chain Fv fragments carrying C-terminal cysteine residues: Production of bivalent and biotinylated miniantibodies (1994) Mol Immunol 31: 1047-1058.

Rahkonen et al. Characterization of the murine Timp4 gene, localization within intron 5 of the synapsin 2 gene and tissue distribution of the mRNA (2002) Biochem Biophys Acta 1577:45-52.

Thuerauf et al. Differential Effects of Protein Kinase C, Ras, and Raf-1 Kinase on the Induction of the Cardiac B-type Natriuretic Peptide Gene through a Critical Promoter-proximal M-CAT Element (1997) J. Biol. Chem. 272:7464-7472.

Lapointe et al. Tissue-Specific Expression of the Human Brain Natriuretic Peptide Gene in Cardiac Myocytes (1996) Hypertension 27:715-722.

Grepin et al. A hormone-encoding gene identifies a pathway for cardiac but not skeletal muscle gene transcription (1994) Mol Cell Biol 14:3115-29.

Flesch. On the trail of cardiac specific transcription factors (2001) Cardiovasc Res 50:3-6.

Kiewitz et al. Transcriptional regulation of S100A1 and expression during mouse heart development (2000) Biochem Biophys Acta 1498:207-219.

Majalahti-Palvianen et al. Gene Structure of a New Cardiac Peptide Hormone: A Model for Heart Specific Gene Expression. (2000) Endocrinology 141:731-740.

Charron et al. Cooperative Interaction between GATA-4 and GATA-6 Regulates Myocardial Gene Expression (1999) Molecular and cellular biology 19: 4355-4365.

Franz et al. Analysis of tissue-specific gene delivery by recominant adenoviruses containing cardiac-specific promoters (1997) Cardiovasc. Res 35: 560-566.

Robbins et al. In vivo definition of a cardiac specific promoter and its potential utility in remodeling the heart. (1995) Ann. NY Acad Sci 752: 492-505.

Linn et al. Conservation of an AE3 Cl—/HCO3—exchanger cardiac specific exon and promoter region and AE3 mRNA expression patterns in murine and human hearts (1995) Circ Res 76:584-591.

Parmacek et al. A novel myogenic regulatory circuit controls slow/cardiac troponin C gene transcription in skeletal muscle. (1994) Mol Cell Biol. 14:1870-1885.

Hunter et al. Targeting gene expression to specific cardiovascular cell types in transgenic mice. (1993) Hypertension 22: 608-617.

Sartorelli et al. Myocardial activation of the human cardiac alpha-actin promoter by helix-loop-helix proteins (1992) PNAS USA 89: 4047-4051.

(56) References Cited

OTHER PUBLICATIONS

Lasko et al. Targeted oncogene activation by site-specific recombination in transgenic mice. (1992) PNAS 89: 6232-6236.
Bunn et al. Oxygen sensing and molecular adaptation to hypoxia. (1996) Physiol. Rev 76: 839-885.
Dachs et al. The molecular response of mammalian cells to hypoxia and the potential for exploitation in cancer therapy (1996) Br. J. Cancer 74: S126-S132.
Guillemin et al. The hypoxic response: huffing and HIFing (1997) Cell 89:9-12.
Firth et al. Oxygen-regulated control elements in the phosphoglycerate kinase 1 and lactate dehydrogenase A genes: Similarities with the erythropoietin 3'enhancer (1994)PNAS 91: 6496-6500.
Jiang et al. V-SRC Induces Expression of Hypoxia-inducible Factor 1 (HIF-1) and Transcription of Genes Encoding Vascular Endothelial Growth Factor and Enolase 1: Involvement of HIF-1 in Tumor Progressio. (1997) Cancer Res. 57:5328-5335.
Chirgwin et al. Isolation of Biologically Active Ribonucleic Acid from Sources Enriched in Ribonuclease (1979) Biochemistry 18: 5294-5299.
Smith et al. Single-step purification of polypeptides expressed in *Escherichia coli* as fusions with glutathione S-transferase. (1988) Gene 67:31-40.
Amann et al. Tightly regulated tuc promoter vectors useful for the expression of unfused and fused proteins in *Escherchia coli*. (1988) Gene 69:301-315.
Gottesman et al. [11] Minimizing proteolysis in *Escherichia coli*: genetic solutions (1990) Gene Expression Technology: Methods in Enzymology 185, 119-128.
Wada et al. Codon usage tabulated from the GenBank genetic sequence data. (1992) Nucleic Acids Res. 20: 2211-2118.
Baldari et al. A novel leader peptide which allows efficient secretion of a fragment of human interleukin 1 beta in *Saccharomyces cerevisiae*. (1987) EMBO J 6: 229-234.
Kurjan et al. Structure of a yeast pheromone gene (MFα): A putative α-factor precursor contains four tandem copies of mature α-factor (1982) Cell 30: 933-943.
Schultz et al. Expression and secretion in yeast of a 400-kda envelope glycoprotein derived from epstein-barr virus (1987) Gene 54 113-123.
Smith et al. Production of human beta interferon in insect cells infected with a baculovirus expression vector. (1983) Mol Cell Biol 3: 2156-2165.
Lucklow et al. High level expression of nonfused foreign genes with Autographa californica nuclear polyhedrosis virus expression vectors. (1969) Virology 179: 31-39.
Seed. B. An LFA-3 cDNA encodes a phospholipid-linked membrane protein homologous to its receptor CD2. (1987) Nature 329: 840.
Kaufman et al. Translational efficiency of polycistronic mRNAs and their utilization to express heterologous genes in mammalian cells. (1987) EMBO J. 6: 187-195.
Pnkert et al. An albumin enhancer located 10 kb upstream functions along with its promoter to direct efficient, liver-specific expression in transgenic mice. (1987) Genes Dev. 1 268-277.
Winoto et al. A novel inducible and T cell-specific enhancer located at the 3' end of the T cell receptor alpha locus. (1989) EMBO J. 8: 729-733.
Banerji et al. A lymphocyte-specific cellular enhancer is located downstream of the joining region in immunoglobulin heavy chain genes. (1983) Cell 33: 729-740.
Queen et al. Immunoglobulin gene transcription is activated by downstream sequence elements. (1983) Cell 33 741-748.
Byrne et al Multiplex gene regulation: a two-tiered approach to transgene regulation in transgenic mice (1989) PNAS USA 86: 5473-5477.
Edlund et al. Cell-specific expression of the rat insulin gene: evidence for role of two distinct 5'flanking elements. (1985) Science 230-912-916.
Kessel et al Murine developmental control genes (1990) Science 249 374-379.
Camper et al. Postnatal repression of the alpha-fetoprotein gene is enhancer independent. (1989) Genes Dev. 3: 537-546.
Muir et al. The Chemical Synthesis of Proteins. Curr Opin Biotech (1993) vol. 4 p. 420.
Miller et al. Structure of complex of synthetic HIV-1 protease with a substrate-based inhibitor at 2.3 A resolution Science (1989) vol. 246, p. 1149.
Wlodawer et al. Conserved folding in retroviral proteases: crystal structure of a synthetic HIV-1 protease. Science (1989) vol. 245, p. 616.
Huang et al. Sequence-specific 1H NMR assignments, secondary structure, and location of the calcium binding site in the first epidermal growth factor like domain of blood coagulation factor IX Biochemistry (1991) vol. 30 p. 7402.
Schnolzer et al. In Situ neutralization in Boc-chemistry solid phase peptide synthesis. Int J Peptide Prot Res (1992) vol. 40, p. 180-193.
Rajaranthnam et al. Neutrophil activation by monomeric interleukin-8. Science (1994) vo. 264, p. 90.
Wallace et al. Functional role of heme ligation in cytochrome c. Effects of replacement of methionine 80 with natural and non-natural residues by semisynthesis. J. Biol Chem (1992) vol. 267, p. 3852.
Abrahmsen et al. Engineering subtilisin and its substrates for efficient ligation of peptide bonds in aqueous solution. Biochemistry (1991) vol. 30, p. 4151.
Chang et al. Subtiligase: a tool for semisynthesis of proteins. PNAS USA (1994) 91: 12544-12548.
Schnolzer et al. Constructing Proteins by Dovetailing Unprotectd Synthetic Peptides: Backbone-Engineered HIV Protease. Science (1992) vol. 3256, p. 221.
Akaji et al. Studies on Peptides. CXXVII. Synthesis of a Tripentacontapeptide with Epidermal Growth Factor Activity Chem Pharm Bull (Tokyo) (1985) 33:184.
Cosman et al. ULBPs, Novel MHC Class I-Related Molecules, Bind to CMV Glycoprotein UL16 and Stimulate NK Cytotoxicity through the NKG2D Receptor. 2001 Immunity 14: 123-133.
Kohler et al. Continuous cultures of fused cells secreting antibody of predefined specificity. (1975) Nature 256: 495-497.
Brown et al Structural characterization of human melanoma-associated antigen p97 with monoclonal antibodies. (1981) J Immunol 127: 539-546.
Brown et al. Protein antigens of normal and malignant human cells identified by immunoprecipitation with monoclonal antibodies. (1980) J Biol Chem 255: 4980-83.
Yeh et al. Cell surface antigens of human melanoma identified by monoclonal antibody. (1976) PNAS USA 76: 2927-2931.
Yeh et al. A cell-surface antigen which is present in the ganglioside fraction and shared by human melanomas (1982) Int J Cancer 29: 269-275.
Kozbor et al. The production of monoclonal antibodies from human lymphocytes (1983) Immunol Today 4: 72.
Lerner. How to make a hybridoma. (1981) Yale J. Biol. Med. 54: 387-402.
Gefter et al. A simple method for polyethylene glycol-promoted hybridization of mouse myeloma cells. (1977) Somatic Cell Genet. 3: 231-236.
Galfre et al. Antibodies to major histocompatibility antigens produced by hybrid cell lines. (1977) Nature 266: 550-552.
Better et al *Escherichia coli* secretion of an active chimeric antibody fragment (1988) Science 240: 1041-1043.
Liu et al. Chimeric mouse-human IgG1 antibody that can mediate lysis of cancer cells (1987) PNAS USA 84: 3439-3443.
Liu et al. Production of a mouse-human chimeric monoclonal antibody to CD20 with potent Fc-dependent biologic activity (1987) J Immunol 139: 3521-3526.
Sun et al. Chimeric antibody with human constant regions and mouse variable regions directed against carcinoma-associated antigen 17-1A (1987) PNAS USA 84: 214:218.
Nishimura et al. Recombinant Human-Mouse Chimeric Monoclonal Antibody Specific for Common Acute Lymphocytic Leukemia Antigen. (1987) Canc Res 47 999-1005.

(56) References Cited

OTHER PUBLICATIONS

Wood et al. The synthesis and in vivo assembly of functional antibodies in yeast. (1985) Nature 314: 446-449.
Shaw et al. Mouse/Human Chimeric Antibodies to a Tumor-Associated Antigen: Biologic Activity of the Four Human IgG Subclasses. (1988) J Natl Cancer Inst. 80: 1553-1559.
Morrison. Transfectomas Provide Novel Chimeric Antibodies. (1985) Science 229 1202-1207.
Ellison et al. Epitope-tagged ubiquitin. A new probe for analyzing ubiquitin function. (1991) J Biol Chem 266: 21150-21157.
Jones et al. Replacing the complementarity-determining regions in a human antibody with those from a mouse (1986) Nature 321: 552-525.
Verhoeyan et al. Reshaping Human Antibodies: Grafting an Antifysozyme Activity (1988) Science 239: 1534.
Beidler et al Cloning and high level expression of a chimeric antibody with specificity for human carcinoembryonic antigen. (1986) J. Immunol 141: 4053-4060.
Chaudri et al. Interaction between increased SERCA2a activity and β-adrenoceptor stimulation in adult rabbit myocytes. (2002) Am. J Physiol Heart Circ Physiol. 283: H2450-H2457.
Slack et al. Ectopic expression of phospholamban in fast-twitch skeletal muscle alters sarcoplasmic reticulum Ca2+ transport and muscle relaxation (1997) J Biol Chem 272: 18862-18868.
Felgner et al. Improved cationic lipid formulations for in vivo gene therapy. Ann NY Acad Sci 126-139, 1995.
Canonico et al. Aerosol and intravenous transfection of human alpha 1-antitrypsin gene to lungs of rabbits. Am J Respir Cell Mol Biol 10: 24-29, 1994.
Tsan et al. Lung-specific direct in vivo gene transfer with recombinant plasmid DNA. Am J Physiol 268: L1052-1056.
Alton et al. Non-invasive liposome-mediated gene delivery can correct the ion transport defect in cystic fibrosis mutant mice. Nat Genet, 5: 135-142, 1993.
Curiel et al. High-efficiency gene transfer mediated by adenovirus coupled to DNA-polylysine complexes. Hum Gene Ther 3: 147-154. 1992.
Wu et al. Targeting genes delivery and persistent expression of a foreign gene driven by mammalian regulatory elements in vivo. J Biol Chem. 264: 16985-16987 (1989).
Felgner et al. Lipofection: a highly efficient, lipid-mediated DNA-transfection procedure. PNAS USA 84: 7413-7417.
Wang et al. pH-sensitive immunolipsomes mediate target-cell-specific delivery and controlled expression of a foreign gene in mouse. PNAS 84: 7851-7855, 1987.
Williams et al. Introduction of foreign genes into tissues of living mice by DNA-coated microprojectiles. PNAS 88: 2726-2730 1991.
Mann et al, Construction of a retrovirus packaging mutant and its use to produce helper-free defective retrovirus. Cell 33:153, 1983.
Cone et al. High-efficiency gene transfer into mammalian cells: generation of helper-free recombinant retrovirus with broad mammalian host range. PNAS, USA 81: 6349, 1984.
Miller et al. Retrovirus packaging cells. Human Gene Therapy 1:5-14, 1990.
Vile et al. Use of Tissue-specific Expression of the Herpes Simplex Virus Thymidine Kinase Gene to Inhibit Growth of Established Murine Melanomas following Direct Intratumoral Injection of DNA. Cancer Res, 53:3860-3864, 1993.
Vile et al, In Vitro and in Vivo Targeting of Gene Expression to Melanoma Cells. Cancer Res. 53: 962-967 1993.
Ram et al. In situ retroviral-mediated gene transfer for the treatment of brain tumors in rats. Cancer Res 53: 83-88 1993.
Takamiya et al. Gene Therapy of Malignant Brain Tumors: A Rat Glioma Line Bearing the Herpes Simplex Virus Type 1-Thymidine Kinase Gene and Wild Type Retrovirus Kills Other Tumor Cells. J Neurosci Res 33: 493-503 1992.
Baba et al, Thymidine kinase-mediated killing of rat brain tumors. J Neurosurg 79: 729-735.
Coupar et al. A general method for the construction of recombinant vaccinia viruses expressing multiple foreign genes (1988) Gene. 68: 1-10.
Friedmann (1989). Progress Toward Human Gene Therapy Science, 244: 1275-1281.
Horwich et al. Synthesis of hepadnavirus particles that contain replication-defective duck hepatitis B virus genomes in cultured HuH7 cells. (1990) J. Virol. 64: 642-650.
Braunwald et al. Contemporary evaluation and management of hypertrophic cardiomyopathy. (2002) Circ. 106: 1312-1316.
Wigle et al. Hypertrophic cardiomyopathy clinical spectrum and treatment (1995) Circ. 92: 1680-1692.
Pi et al. Diacylglycerol and fatty acids synergistically increase cardiomyocyte contraction via activation of PKC. (2000) Am. J. Physiol Heart Circ Physiol. 279: H26-H34.
Braz et al. PKCα regulates the hypertrophic growth of cardiomyocytes through extracellular signal-regulated kinase1/2 (ERK1/2). (2002) J. Cell Biol 156: 905-919.
Sohal et al. Temporally regulated and tissue-specific gene manipulations in the adult and embryonic heart using a tamoxifen-inducible Cre protein. (2001) Circ Res 89: 20-25.
Nagueh et al. Tissue Doppler Imaging Consistently Detects Myocardial Contraction and Relaxation Abnormalities, Irrespective of Cardiac Hypertrophy, in a Transgenic Rabbit Model of Human Hypertrophic Cardiomyopathy (2000) Circ 102: 1346-1350.
Sanbe et al. (2001). Examining the in vivo role of the amino terminus of the essential myosin light chain. J. Biol Chem. 276: 32682-32686.
Sanbe et al. Abnormal cardiac structure and function in mice expressing nonphosphorylatable cardiac regulatory myosin light chain 2. (1999) J. Biol Chem 274: 21085-21094.
Berge et al. Pharmaceutical Salts, (1977) J. Pharm Sci. 66-1-19.
Chen et al. Gene therapy for brain tumors: regression of experimental gliomas by adenovirus-mediated gene transfer in vivo. (1994) PNAS USA 91: 3054-3057.
Zhou et al. Spontaneous activation of β2-but not β1-adrenoceptors expressed in cardiac myocytes from β1β2 double knockout mice. (2000) Mol Pharmacol 58: 887-894.
Kuschel et al. Gi protein-mediated functional compartmentalization of cardiac β2-adrenergic signaling (1999) J Bio Chem. 274: 22048-22052.
Liu et al. FRET-based direct detection of dynamic protein kinase A activity on the sarcoplasmic reticulum in cardiomyocytes. (2011) Biochem Biophys Res Commun. 404: 581-586.
Vanderheyden et al. Myocardial gene expression in heart failure patients treated with cardiac resynchronization therapy: responders versus nonresponders (2008) J Am Coll Cardiol. 51: 129-136.
Woo et al. Stereochemistry of an agonist determines coupling preference of β2-adrenoceptor to different G proteins in cardiomyocytes. (2009) Mol Pharmacol. 75: 158-165.
Xiao et al. Enhanced Gi signaling selectively negates β2-adrenergic receptor (AR)—but not β1-AR-mediated positive inotropic effect in myocytes from failing rat hearts. (2003) Circulation. 108: 1633-1639.
Gong et al. The effect of Gi-protein inactivation on basal. and β1-and β2AR-stimulated contraction of myocytes from transgenic mice overexpressing the β2-adrenoceptor. (2000) Br. J Pharmacol 131: 594-600.
Rau et al. Overexpression of wild-type Gαi-2 suppresses β-adrenergic signaling in cardiac myocytes. (2003) FASEB J. 17: 523-525.
Raake et al. G protein-coupled receptor kinase 2 ablation in cardiac myocytes before or after myocardial infarction prevents heart failure (2008) Circ Res. 103: 413-422.
Baillie et al. β-Arrestin-mediated PDE4 cAMP phosphodiesterase recruitment regulates β-adrenoceptor switching from Gs to Gi. (2003) PNAS USA 100: 940-945.
Rapti et al. Targeted gene therapy for the treatment of heart failure. (2011) Can J Cardiol 27: 265-283.
Pearce, The use of beta agonists and the risk of death and near death from asthma. (2009) J Clin Epidemiol. 62: 582-587.
Chakir et al. Reversal of global apoptosis and regional stress kinase activation by cardiac resynchronization. Circulation. 2008;117:1369-1377.

(56) References Cited

OTHER PUBLICATIONS

Spragg et al. Regional alterations in protein expression in the dyssynchronous failing heart. (2003) Circulation 108: 929-932.

Leclercq et al. Systolic improvement and mechanical resynchronization does not require electrical synchrony in the dilated failing heart with left bundle-branch block. (2002) Circulation 106: 1760-1763.

Gao et al. Myofilament Ca2+ sensitivity in intact versus skinned rat ventricular muscle. (1994) Circ Res 74: 408-415.

Arrell et al. Proteomic analysis of pharmacologically preconditioned cardiomyocytes revels novel phosphorylation of myosin light chain 1. (2001) Circ Res 89: 480-487.

Kirk et al. Left ventricular any myocardial function in mice expressing constitutively pseudophosphoryated cardiac troponin I. (2009) Circ Res. 105: 1232-1239.

Iuliano et al. QRS duration and mortality in patients with congestive heart failure. (2002) Am Heart J 143: 1085-1019.

Kiuchi et al. Myocardial beta-adrenergic receptor function during the development of pacing-induced heart failure. (1993) J. Clin Invest 91: 907-914.

Parissis et al. Levosimendan from basic science to clinical practice. (2009) Heart Fail Rev 14: 265-275.

Gupta et al. HDAC4 and PCAF bind to cardiac sarcomeres and play a role in regulating myofilament contractile activity. (2008) J Biol Chem 283 10135-10146.

Cassidy et al. Asparaginyl deamidation-methylation of rat ventricular myosin light chains. (1991) J Mol Cell Cardio 23: 589-601.

Avner et al. H2O2 alters rat cardiac sarcomere function and protein phosphorylation through redox signaling. (2010) Am J Physiol Heart Circ Physiol 299: H723-H730.

Burkhart et al. Phosphorylation or glutamic acid substitution at protein kinase C sites on cardiac troponin I differentially depress myofilament tension and shortening velocity. (2003) J Biol Chem 278: 11265-11272.

Wang et al. PKC-βII sensitizes cardiac myofilaments to Ca 2+ by phosphorylating troponin I on threonine-144. (2006) J Mol Cell Cardiol 41: 823-833.

Kooij et al. Protein kinase C α and ε phosphorylation of troponin and myosin binding protein C reduce Ca2+ sensitivity in human myocardium. (2009) Basic Res Cardiol 105: 289-300.

Biesiadecki et al. The troponin C G159D mutation blunts myofilament desensitization induced by troponin I Ser23/24 phosphorylation. (2007) Circ Res 100: 1486-1493.

Bardswell et al Distinct sarcomeric substrates are responsible for protein kinase D-mediated regulation of cardiac myofilament Ca2+ sensitivity and cross-bridge cycling. (2010) J. Biol. Chem. 285: 5674-5682.

Colson et al. Differential roles of regulatory light chain and myosin binding protein-C phosphorylations in the modulation of cardiac force development. (2010) J. Physiol 588: 981-993.

Anderson et al. The effects of PKCα phosphorylation on the extensibility of titins's PEVK element. (2010) J. Struct Biol 170: 270-277.

Jia et al. Identification of Novel Protein Kinase A Phosphorylatin Sites in the M-domain of Human and Murine Cardiac Myosin Binding Protein-C Using Mass Spectrometry Analysis (2010) J Proteome Res 9: 1843-1853.

Wang. et al., "Brief rapid pacing depresses contractile function via Ca2+/PKC-dependent signaling in cat ventricular myocytes", AJP Heart and Circulatory Physiology, Feb. 2001, 11 pages.

Wu, et al., "Protein Kinase C A Novel Regulator of Both Phosphorylation and De-Phosphoryaltion of Cardiac Sarcomeric Proteins", The Journal of Biological Chemistry, vol. 282, No. 42, pp. 30691-30698, 2007.

International Search Report for PCT/US2011/059787 dated May 30, 2012.

Chung, E. et al., "Effect of Peri-Infarct Pacing Early After Myocardial Infarction", Downloaded from http://ahajournals.org by on Apr. 5, 2019, 9 pages.

* cited by examiner

REPLACEMENT SHEET
FIG. 1A
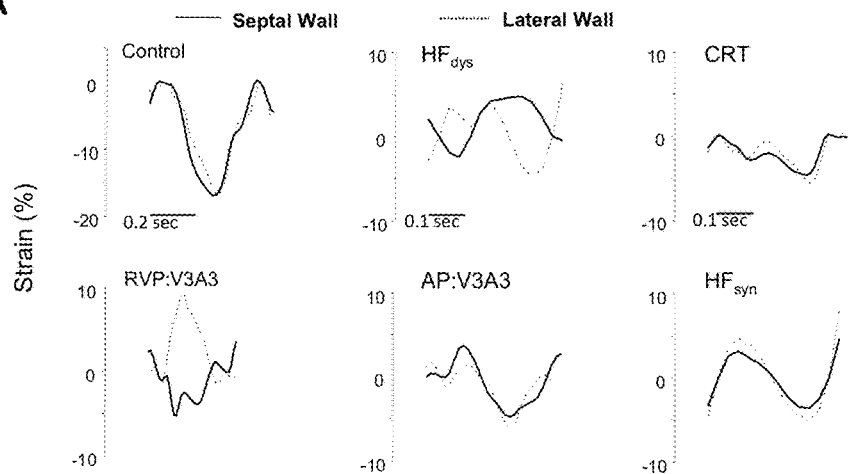

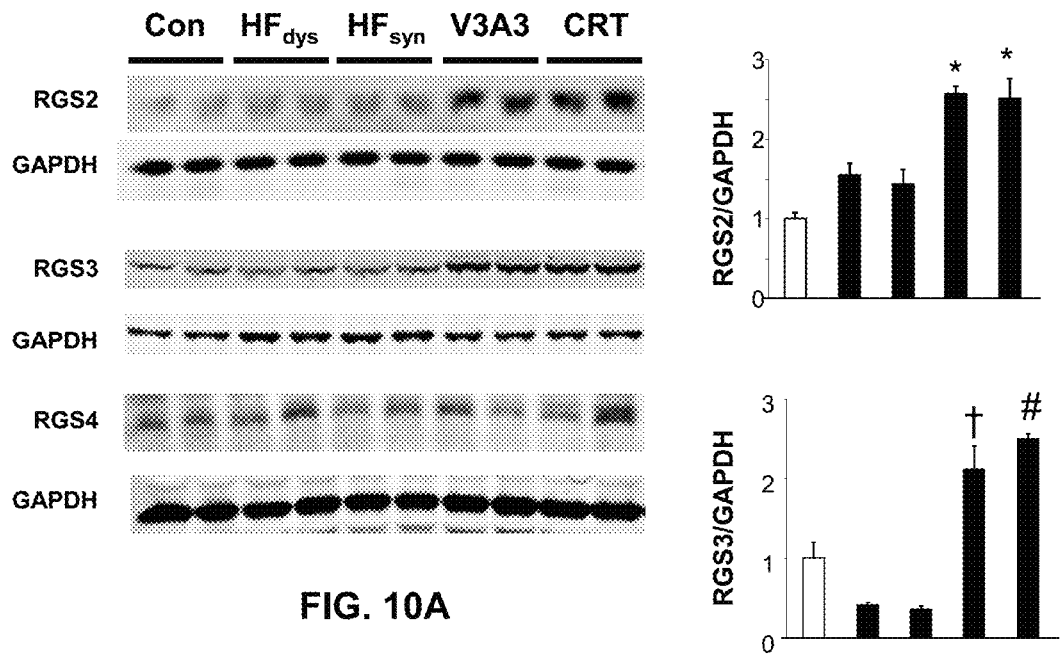
FIG. 10A
FIG. 10B
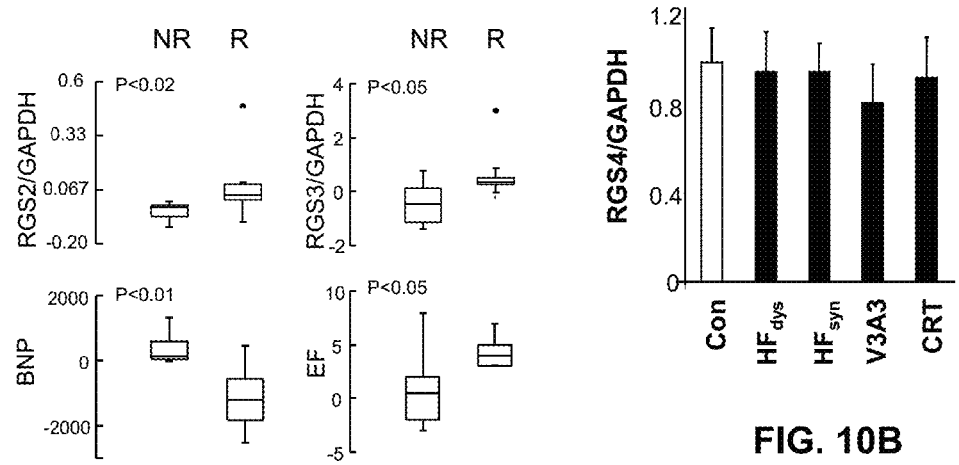
FIG. 10C

FIG. 19A
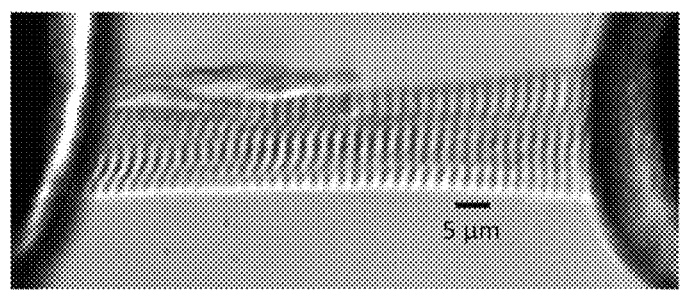
FIG. 19B
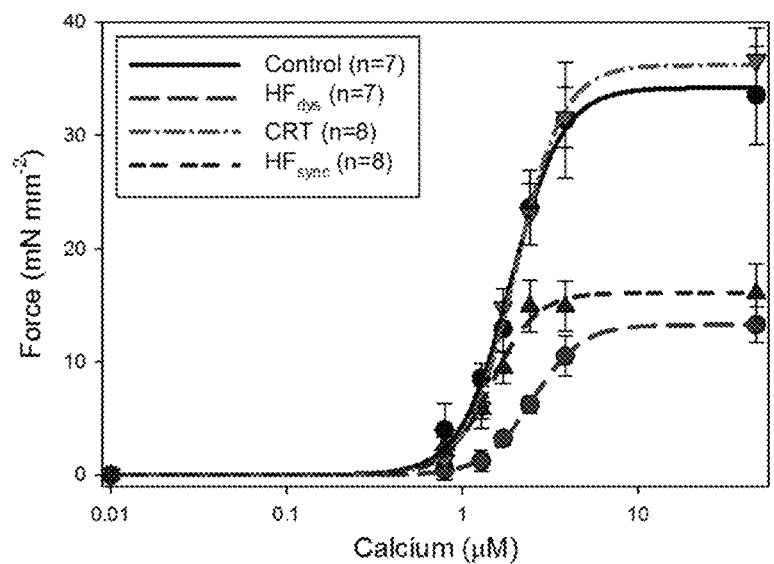
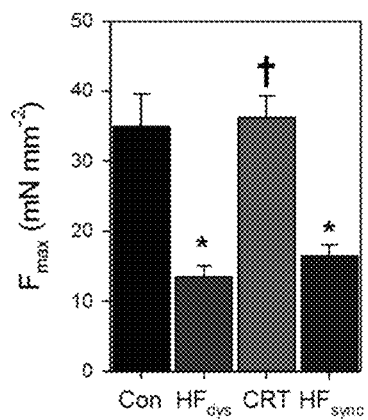
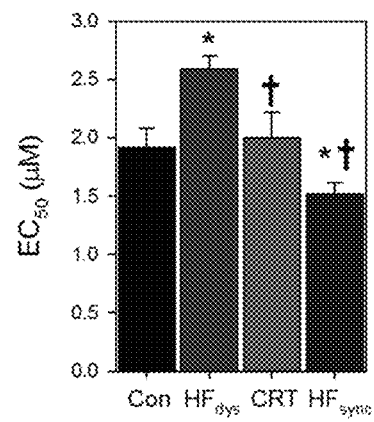
FIG. 19C  FIG. 19D FIG. 20A
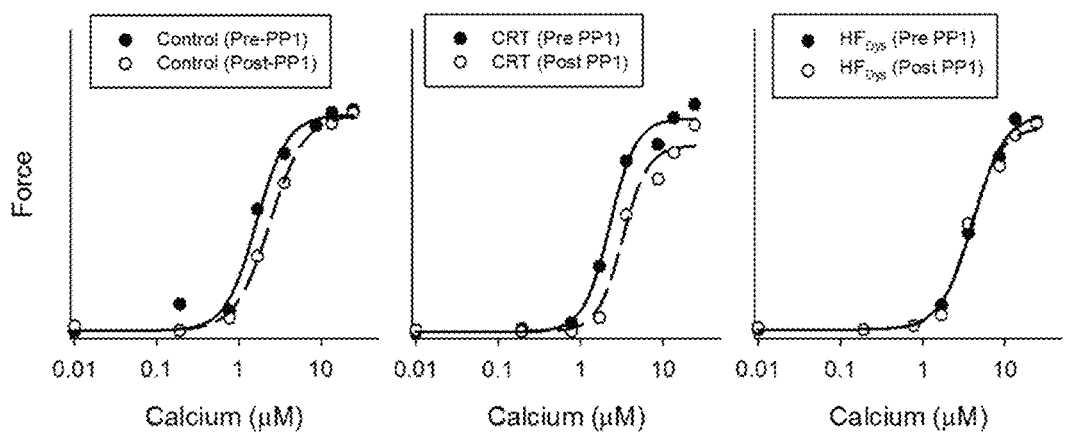
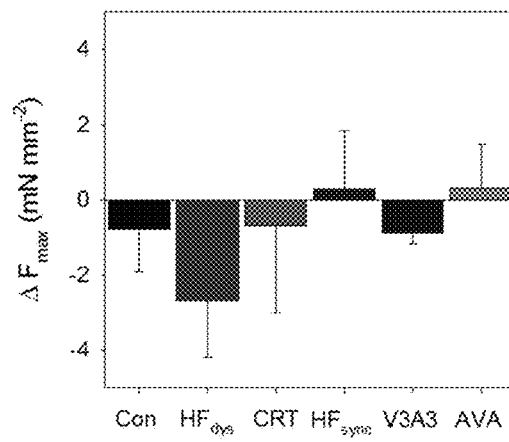
FIG. 20B
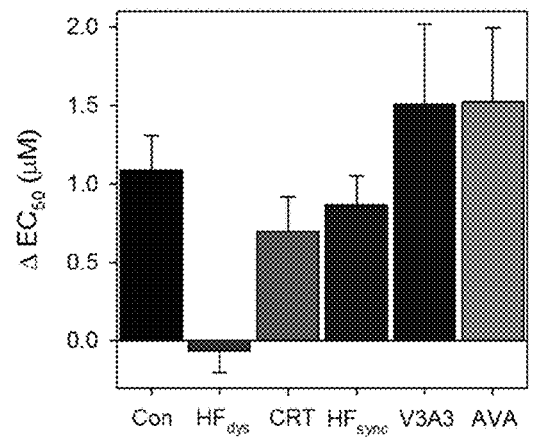
FIG. 20C

SEQUENCE LISTING

<160> NUMBER OF SEQ ID NOS: 29

<210> SEQ ID NO 1
<211> LENGTH: 636
<212> TYPE: DNA
<213> ORGANISM: Homo Sapiens

<400> SEQUENCE: 1

```
atgcaaagtg ctatgttctt ggctgttcaa cacgactgca gacccatgga caagagcgca        60
ggcagtggcc acaagagcga ggagaagcga gaaaagatga acggaccct tttaaaagat       120 tggaagaccc gtttgagcta cttcttacaa aattcctcta ctcctgggaa gcccaaaacc       180
ggcaaaaaaa gcaaacagca agctttcatc aagccttctc ctgaggaagc acagctgtgg       240
tcagaagcat tgacgagct gctagccagc aaatatggtc ttgctgcatt cagggctttt       300
ttaaagtcgg aattctgtga agaaaatatt gaattctggc tggcctgtga agacttcaaa       360 aaaccaaat caccccaaaa gctgtcctca aaagcaagga aaatatatac tgacttcata       420
```

```
gaaaaggaag ctccaaaaga gataaacata gattttcaaa ccaaaactct gattgcccag    480
aatatacaag aagctacaag tggctgcttt acaactgccc agaaaagggt atacagcttg    540
atggagaaca actcttatcc tcgtttcttg gagtcagaat tctaccagga cttgtgtaaa    600
aagccacaaa tcaccacaga gcctcatgct acatga                              636
```

<210> SEQ ID NO 2
<211> LENGTH: 211
<212> TYPE: PRT
<213> ORGANISM: Homo Sapiens
<400> SEQUENCE: 2

```
Met Gln Ser Ala Met Phe Leu Ala Val Gln His Asp Cys Arg Pro Met
1               5                   10                  15

Asp Lys Ser Ala Gly Ser Gly His Lys Ser Glu Glu Lys Arg Glu Lys
            20                  25                  30

Met Lys Arg Thr Leu Leu Lys Asp Trp Lys Thr Arg Leu Ser Tyr Phe
        35                  40                  45

Leu Gln Asn Ser Ser Thr Pro Gly Lys Pro Lys Thr Gly Lys Lys Ser
    50                  55                  60

Lys Gln Gln Ala Phe Ile Lys Pro Ser Pro Glu Glu Ala Gln Leu Trp
65                  70                  75                  80

Ser Glu Ala Phe Asp Glu Leu Leu Ala Ser Lys Tyr Gly Leu Ala Ala
                85                  90                  95

Phe Arg Ala Phe Leu Lys Ser Glu Phe Cys Glu Glu Asn Ile Glu Phe
            100                 105                 110

Trp Leu Ala Cys Glu Asp Phe Lys Lys Thr Lys Ser Pro Gln Lys Leu
        115                 120                 125

Ser Ser Lys Ala Arg Lys Ile Tyr Thr Asp Phe Ile Glu Lys Glu Ala
    130                 135                 140

Pro Lys Glu Ile Asn Ile Asp Phe Gln Thr Lys Thr Leu Ile Ala Gln
145                 150                 155                 160

Asn Ile Gln Glu Ala Thr Ser Gly Cys Phe Thr Thr Ala Gln Lys Arg
                165                 170                 175

Val Tyr Ser Leu Met Glu Asn Asn Ser Tyr Pro Arg Phe Leu Glu Ser
            180                 185                 190

Glu Phe Tyr Gln Asp Leu Cys Lys Lys Pro Gln Ile Thr Thr Glu Pro
        195                 200                 205

His Ala Thr
    210
```

<210> SEQ ID NO 3
<211> LENGTH: 636
<212> TYPE: DNA
<213> ORGANISM: Mus Musculus
<400> SEQUENCE: 3

```
atgcaaagtg ccatgttcct ggctgtccag cacgactgcg tacccatgga caagagtgca    60
ggcaacggcc ccaaggtcga ggagaagcgg gagaaaatga gcggacact cttaaaggat    120 tggaagaccc gtttgagcta cttcttgcag aattcctctg ctcctgggaa gcccaaaact    180
ggcaagaaaa gcaaacagca aacttttatc aagccttctc ctgaggaagc gcagctctgg    240
gcagaagcat ttgatgaact gctggccagt aaatatgggc tggctgcatt cagggcgttt    300
ttaaagtccg agttctgtga agaaacatt gaattctggt tggcttgtga agacttcaaa    360 aaaccaaat caccccaaaa actgtcctca aaagcaagga aaatctatac cgacttcata    420
```

```
gagaaggaag ctcccaaaga gataaacata gacttccaaa cgaaatctct gattgcccaa    480
aatatccaag aggctacaag tggctgcttc accacagctc agaagagggt gtacagtttg    540
atggagaaca attcttatcc tcggttcttg gagtccgaat tctaccagga cttatgtaaa    600
aagccacaga tcaccacgga gccccatgct acatga                              636
```

<210> SEQ ID NO 4
<211> LENGTH: 211
<212> TYPE: PRT
<213> ORGANISM: Mus Musculus

<400> SEQUENCE: 4

```
Met Gln Ser Ala Met Phe Leu Ala Val Gln His Asp Cys Val Pro Met
1               5                   10                  15

Asp Lys Ser Ala Gly Asn Gly Pro Lys Val Glu Glu Lys Arg Glu Lys
            20                  25                  30

Met Lys Arg Thr Leu Leu Lys Asp Trp Lys Thr Arg Leu Ser Tyr Phe
        35                  40                  45

Leu Gln Asn Ser Ser Ala Pro Gly Lys Pro Lys Thr Gly Lys Lys Ser
    50                  55                  60

Lys Gln Gln Thr Phe Ile Lys Pro Ser Pro Glu Ala Gln Leu Trp
65                  70                  75                  80

Ala Glu Ala Phe Asp Glu Leu Leu Ala Ser Lys Tyr Gly Leu Ala Ala
                85                  90                  95

Phe Arg Ala Phe Leu Lys Ser Glu Phe Cys Glu Glu Asn Ile Glu Phe
            100                 105                 110

Trp Leu Ala Cys Glu Asp Phe Lys Lys Thr Lys Ser Pro Gln Lys Leu
        115                 120                 125

Ser Ser Lys Ala Arg Lys Ile Tyr Thr Asp Phe Ile Glu Lys Glu Ala
    130                 135                 140

Pro Lys Glu Ile Asn Ile Asp Phe Gln Thr Lys Ser Leu Ile Ala Gln
145                 150                 155                 160

Asn Ile Gln Glu Ala Thr Ser Gly Cys Phe Thr Thr Ala Gln Lys Arg
                165                 170                 175

Val Tyr Ser Leu Met Glu Asn Asn Ser Tyr Pro Arg Phe Leu Glu Ser
            180                 185                 190

Glu Phe Tyr Gln Asp Leu Cys Lys Lys Pro Gln Ile Thr Thr Glu Pro
        195                 200                 205

His Ala Thr
    210
```

<210> SEQ ID NO 5
<211> LENGTH: 858
<212> TYPE: DNA
<213> ORGANISM: Canis familiaris

<400> SEQUENCE: 5

```
atgaggaaac cctgcatcct tgcactccca ggacgaggat ggctctggcg catcacagtt     60
tccacgtctt ggtgtttccc tccgtctcct cgtgaggaga ctgggacttc tctgtcctg    120 gaaggagaag caaccaagga tttcggagaa aaagctttgc aaccccacgg aagacccaa    180 tcacgcaggt tgcggggagc aaggctgcac accctcttaa acacggccg tcggataaag    240 tcccttcctc cgcacgactg cggatccatg acaagagct cgagcaacag ctccaagcac    300
gaggagaagc gggaaaagat gaagcggacc ctattaaaag attggaagac ccgtttgagc    360
```

```
tacttcttac aaaattcgtc gtctcctggg aagcccaaaa atggcaagaa aagcaaacag      420
caaaccttca tcaagccttc tcctgaggaa gcacagctgt ggtcagaagc gtttgatgag      480
ctgctagcca gtaaatatgg tcttgctgca ttcagggctt ttttaaaatc tgagttttgt      540
gaagaaaata ttgagttctg gctggcctgc gaagacttca aaaaaaccaa gtcaccccaa      600
aagctgtcct ccaaagcaag gaaaatatat actgatttca tagaaaaaga agcacctaaa      660
gagataaaca tagactttca aaccaaaact ctgattgccc aaaacataca agaagctaca      720
agtggctgct ttacaaccgc ccagaaaagg gtctacagct tgatggagaa caactcttat      780
ccccgtttct tggagtcaga attctatcag gacttgtgta aaaagccaca gatcgccaca      840
gagccccatg ctacatga                                                   858
```

<210> SEQ ID NO 6
<211> LENGTH: 285
<212> TYPE: PRT
<213> ORGANISM: Canis familiaris

<400> SEQUENCE: 6

```
Met Arg Lys Pro Cys Ile Leu Ala Leu Pro Gly Arg Gly Trp Leu Trp
1               5                   10                  15

Arg Ile Thr Val Ser Thr Ser Trp Cys Phe Pro Ser Pro Arg Glu
            20                  25                  30

Glu Ser Trp Asp Phe Ser Val Leu Glu Gly Glu Ala Thr Lys Asp Phe
            35                  40                  45

Gly Glu Lys Ala Leu Gln Pro His Gly Lys Thr Gln Ser Arg Arg Leu
        50                  55                  60

Arg Gly Ala Arg Leu His Thr Leu Leu Lys His Gly Arg Arg Ile Lys
65                  70                  75                  80

Ser Leu Ser Pro His Asp Cys Gly Ser Met Asp Lys Ser Ser Asn
                85                  90                  95

Ser Ser Lys His Glu Glu Lys Arg Glu Lys Met Lys Arg Thr Leu Leu
            100                 105                 110

Lys Asp Trp Lys Thr Arg Leu Ser Tyr Phe Leu Gln Asn Ser Ser Ser
        115                 120                 125

Pro Gly Lys Pro Lys Asn Gly Lys Ser Lys Gln Gln Thr Phe Ile
    130                 135                 140

Lys Pro Ser Pro Glu Glu Ala Gln Leu Trp Ser Glu Ala Phe Asp Glu
145                 150                 155                 160

Leu Leu Ala Ser Lys Tyr Gly Leu Ala Ala Phe Arg Ala Phe Leu Lys
                165                 170                 175

Ser Glu Phe Cys Glu Glu Asn Ile Glu Phe Trp Leu Ala Cys Glu Asp
            180                 185                 190

Phe Lys Lys Thr Lys Ser Pro Gln Lys Leu Ser Ser Lys Ala Arg Lys
        195                 200                 205

Ile Tyr Thr Asp Phe Ile Glu Lys Glu Ala Pro Lys Glu Ile Asn Ile
    210                 215                 220

Asp Phe Gln Thr Lys Thr Leu Ile Ala Gln Asn Ile Gln Glu Ala Thr
225                 230                 235                 240

Ser Gly Cys Phe Thr Thr Ala Gln Lys Arg Val Tyr Ser Leu Met Glu
                245                 250                 255

Asn Asn Ser Tyr Pro Arg Phe Leu Glu Ser Glu Phe Tyr Gln Asp Leu
            260                 265                 270

Cys Lys Lys Pro Gln Ile Ala Thr Glu Pro His Ala Thr
        275                 280                 285
```

<210> SEQ ID NO 7
<211> LENGTH: 2754
<212> TYPE: DNA
<213> ORGANISM: Homo Sapiens

<400> SEQUENCE: 7

| | | | | | |
|---|---|---|---|---|---|
| atgaaccgct | tcaatgggct | ctgcaaggtg | tgctcggagc | gccgctaccg | ccagatcacc | 60 |
| atcccgaggg | gaaaggacgg | ctttggcttc | accatctgct | gcgactctcc | agttcgagtc | 120 |
| caggccgtgg | attccggggg | tccggcggaa | cgggcagggc | tgcagcagct | ggacacggtg | 180 |
| ctgcagctga | atgagaggcc | tgtggagcac | tggaaatgtg | tggagctggc | cacgagatc | 240 |
| cggagctgcc | ccagtgagat | catcctactc | gtgtggcgca | tggtccccca | ggtcaagcca | 300 |
| ggaccagatg | gcggggtcct | gcggcgggcc | tcctgcaagt | cgacacatga | cctccagtca | 360 |
| ccccccaaca | aacgggagaa | gaactgcacc | catggggtcc | aggcacggcc | tgagcagcgc | 420 |
| cacagctgcc | acctggtatg | tgacagtctc | tgatgggctgc | tgctcggcgg | ctgggagcgc | 480 |
| tacaccgagg | tggccaagcg | cgggggccag | cacaccctgc | ctgcactgtc | ccgtgccact | 540 |
| gcccccaccg | accccaacta | catcatcctg | gcccgctga | atcctgggag | ccagctgctc | 600 |
| cggcctgtgt | accaggagga | taccatcccc | gaagaatcag | ggagtccag | taaagggaag | 660 |
| tcctacacag | gctggggaa | gaagtccgg | ctgatgaaga | cagtgcagac | catgaagggc | 720 |
| cacgggaact | accaaaactg | cccggttgtg | aggccgcatg | ccacgcactc | aagctatggc | 780 |
| acctacgtca | ccctggcccc | caaagtcctg | gtgttccctg | tctttgttca | gcctctagat | 840 |
| ctctgtaatc | ctgccccggac | cctcctgctg | tcagaggagc | tgctgctgta | tgaagggagg | 900 |
| aacaaggctg | ccgaggtgac | actgtttgcc | tattcggacc | tgctgctctt | caccaaggag | 960 |
| gacgagcctg | gccgctgcga | cgtcctgagg | aaccccctct | acctccagag | tgtgaagctg | 1020 |
| caggaaggtt | cttcagaaga | cctgaaattc | tgcgtgctct | atctagcaga | gaaggcagag | 1080 |
| tgcttattca | ctttggaagc | gcactcgcag | gagcagaaga | agagagtgtg | ctggtgcctg | 1140 |
| tcggagaaca | tcgccaagca | gcaacagctg | gcagcatcac | cccggacag | caagatgttt | 1200 |
| gagacggagg | cagatgagaa | gagggagatg | gccttggagg | aagggaaggg | gcctggtgcc | 1260 |
| gaggattccc | cacccagcaa | ggagccctct | cctggccagg | agcttcctcc | aggacaagac | 1320 |
| cttccaccca | caaggactc | cccttctggg | caggaacccg | ctcccagcca | agaaccactg | 1380 |
| tccagcaaag | actcagctac | ctctgaagga | tcccctccag | gcccagatgc | tccgcccagc | 1440 |
| aaggatgtgc | caccatgcca | ggaaccccct | ccagcccaag | acctctcacc | ctgccaggac | 1500 |
| ctacctgctg | gtcaagaacc | cctgcctcac | caggaccctc | tactcaccaa | agacctccct | 1560 |
| gccatccagg | aatcccccac | ccgggacctt | ccacctgtc | aagatctgcc | tcctagccag | 1620 |
| gtctccctgc | cagccaaggc | ccttactgag | gacaccatga | gctccgggga | cctactagca | 1680 |
| gctactgggg | acccacctgc | ggcccccagg | ccagccttcg | tgatccctga | ggtccggctg | 1740 |
| gatagcacct | acagccagaa | ggcaggggca | gagcagggct | gctcgggaga | tgaggaggat | 1800 |
| gcagaagagg | ccgaggaggt | ggaggagggg | gaggaagggg | aggaggacga | ggatgaggac | 1860 |
| accagcgatg | acaactacgg | agagcgcagt | gaggccaagc | gcagcagcat | gatcgagacg | 1920 |
| ggccaggggg | ctgagggtgg | cctctcactg | cgtgtgcaga | actcgctgcg | gcgccggacg | 1980 |
| cacagcgagg | gcagcctgct | gcaggagccc | gagggccct | gctttgcctc | cgacaccacc | 2040 |
| ttgcactgct | cagacggtga | gggcgccgcc | tccacctggg | gcatgccttc | gcccagcacc | 2100 |

-continued

```
ctcaagaaag agctgggccg caatggtggc tccatgcacc acctttccct cttcttcaca      2160
ggacacagga agatgagcgg ggctgacacc gttgggatg atgacgaagc ctcccggaag       2220
agaaagagca aaacctagc caaggacatg aagaacaagc tggggatctt cagacggcgg      2280
aatgagtccc ctggagcccc tcccgcgggc aaggcagaca aaatgatgaa gtcattcaag     2340
cccacctcag aggaagccct caagtggggc gagtccttgg agaagctgct ggttcacaaa    2400
tacgggttag cagtgttcca agccttcctt cgcactgagt tcagtgagga gaatctggag    2460
ttctggttgg cttgtgagga cttcaagaag gtcaagtcac agtccaagat ggcatccaag    2520
gccaagaaga tctttgctga atacatcgcg atccaggcat gcaaggaggt caacctggac    2580
tcctacacgc gggagcacac caaggacaac ctgcagagcg tcacgcgggg ctgcttcgac    2640
ctggcacaga gcgcatctt cgggctcatg gaaaaggact cgtaccctcg ctttctccgt     2700
tctgacctct acctggacct tattaaccag aagaagatga gtccccccgct ttag         2754
```

<210> SEQ ID NO 8
<211> LENGTH: 917
<212> TYPE: PRT
<213> ORGANISM: Homo Sapiens

<400> SEQUENCE: 8

```
Met Asn Arg Phe Asn Gly Leu Cys Lys Val Cys Ser Glu Arg Arg Tyr
1               5                   10                  15

Arg Gln Ile Thr Ile Pro Arg Gly Lys Asp Gly Phe Gly Phe Thr Ile
                20                  25                  30

Cys Cys Asp Ser Pro Val Arg Val Gln Ala Val Asp Ser Gly Gly Pro
            35                  40                  45

Ala Glu Arg Ala Gly Leu Gln Gln Leu Asp Thr Val Leu Gln Leu Asn
        50                  55                  60

Glu Arg Pro Val Glu His Trp Lys Cys Val Glu Leu Ala His Glu Ile
65                  70                  75                  80

Arg Ser Cys Pro Ser Glu Ile Ile Leu Leu Val Trp Arg Met Val Pro
                85                  90                  95

Gln Val Lys Pro Gly Pro Asp Gly Gly Val Leu Arg Arg Ala Ser Cys
                100                 105                 110

Lys Ser Thr His Asp Leu Gln Ser Pro Pro Asn Lys Arg Glu Lys Asn
            115                 120                 125

Cys Thr His Gly Val Gln Ala Arg Pro Glu Gln Arg His Ser Cys His
        130                 135                 140

Leu Val Cys Asp Ser Ser Asp Gly Leu Leu Gly Gly Trp Glu Arg
145                 150                 155                 160

Tyr Thr Glu Val Ala Lys Arg Gly Gly Gln His Thr Leu Pro Ala Leu
                165                 170                 175

Ser Arg Ala Thr Ala Pro Thr Asp Pro Asn Tyr Ile Ile Leu Ala Pro
                180                 185                 190

Leu Asn Pro Gly Ser Gln Leu Leu Arg Pro Val Tyr Gln Glu Asp Thr
            195                 200                 205

Ile Pro Glu Glu Ser Gly Ser Pro Ser Lys Lys Ser Tyr Thr Gly
        210                 215                 220

Leu Gly Lys Lys Ser Arg Leu Met Lys Thr Gln Thr Met Lys Gly
225                 230                 235                 240

His Gly Asn Tyr Gln Asn Cys Pro Val Val Arg Pro His Ala Thr His
                245                 250                 255

Ser Ser Tyr Gly Thr Tyr Val Thr Leu Ala Pro Lys Val Leu Val Phe
```

```
                260                 265                 270
Pro Val Phe Val Gln Pro Leu Asp Leu Cys Asn Pro Ala Arg Thr Leu
            275                 280                 285
Leu Leu Ser Glu Glu Leu Leu Tyr Glu Gly Arg Asn Lys Ala Ala
        290                 295                 300
Glu Val Thr Leu Phe Ala Tyr Ser Asp Leu Leu Phe Thr Lys Glu
305                 310                 315                 320
Asp Glu Pro Gly Arg Cys Asp Val Leu Arg Asn Pro Leu Tyr Leu Gln
                325                 330                 335
Ser Val Lys Leu Gln Glu Gly Ser Ser Glu Asp Leu Lys Phe Cys Val
            340                 345                 350
Leu Tyr Leu Ala Glu Lys Ala Glu Cys Leu Phe Thr Leu Glu Ala His
        355                 360                 365
Ser Gln Glu Gln Lys Lys Arg Val Cys Trp Cys Leu Ser Glu Asn Ile
    370                 375                 380
Ala Lys Gln Gln Gln Leu Ala Ala Ser Pro Pro Asp Ser Lys Met Phe
385                 390                 395                 400
Glu Thr Glu Ala Asp Glu Lys Arg Glu Met Ala Leu Glu Glu Gly Lys
                405                 410                 415
Gly Pro Gly Ala Glu Asp Ser Pro Ser Lys Glu Pro Ser Pro Gly
            420                 425                 430
Gln Glu Leu Pro Pro Gly Gln Asp Leu Pro Pro Asn Lys Asp Ser Pro
        435                 440                 445
Ser Gly Gln Glu Pro Ala Pro Ser Gln Glu Pro Leu Ser Ser Lys Asp
    450                 455                 460
Ser Ala Thr Ser Glu Gly Ser Pro Gly Pro Asp Ala Pro Pro Ser
465                 470                 475                 480
Lys Asp Val Pro Pro Cys Gln Glu Pro Pro Ala Gln Asp Leu Ser
                485                 490                 495
Pro Cys Gln Asp Leu Pro Ala Gly Gln Glu Pro Leu Pro His Gln Asp
            500                 505                 510
Pro Leu Leu Thr Lys Asp Leu Pro Ala Ile Gln Glu Ser Pro Thr Arg
        515                 520                 525
Asp Leu Pro Pro Cys Gln Asp Leu Pro Pro Ser Gln Val Ser Leu Pro
    530                 535                 540
Ala Lys Ala Leu Thr Glu Asp Thr Met Ser Ser Gly Asp Leu Leu Ala
545                 550                 555                 560
Ala Thr Gly Asp Pro Pro Ala Ala Pro Arg Pro Ala Phe Val Ile Pro
                565                 570                 575
Glu Val Arg Leu Asp Ser Thr Tyr Ser Gln Lys Ala Gly Ala Glu Gln
            580                 585                 590
Gly Cys Ser Gly Asp Glu Asp Ala Glu Ala Glu Val Glu
        595                 600                 605
Glu Gly Glu Gly Glu Glu Asp Glu Asp Thr Ser Asp Asp
    610                 615                 620
Asn Tyr Gly Glu Arg Glu Ala Lys Arg Ser Met Ile Glu Thr
625                 630                 635                 640
Gly Gln Gly Ala Glu Gly Leu Ser Leu Arg Val Gln Asn Ser Leu
                645                 650                 655
Arg Arg Arg Thr His Ser Glu Gly Ser Leu Leu Gln Glu Pro Arg Gly
            660                 665                 670
Pro Cys Phe Ala Ser Asp Thr Thr Leu His Cys Ser Asp Gly Glu Gly
        675                 680                 685
```

```
Ala Ala Ser Thr Trp Gly Met Pro Ser Pro Ser Thr Leu Lys Lys Glu
        690                 695                 700
Leu Gly Arg Asn Gly Gly Ser Met His His Leu Ser Leu Phe Phe Thr
705                 710                 715                 720
Gly His Arg Lys Met Ser Gly Ala Asp Thr Val Gly Asp Asp Asp Glu
                725                 730                 735
Ala Ser Arg Lys Arg Lys Ser Lys Asn Leu Ala Lys Asp Met Lys Asn
            740                 745                 750
Lys Leu Gly Ile Phe Arg Arg Asn Glu Ser Pro Gly Ala Pro Pro
        755                 760                 765
Ala Gly Lys Ala Asp Lys Met Met Lys Ser Phe Lys Pro Thr Ser Glu
        770                 775                 780
Glu Ala Leu Lys Trp Gly Glu Ser Leu Glu Lys Leu Leu Val His Lys
785                 790                 795                 800
Tyr Gly Leu Ala Val Phe Gln Ala Phe Leu Arg Thr Glu Phe Ser Glu
                805                 810                 815
Glu Asn Leu Glu Phe Trp Leu Ala Cys Glu Asp Phe Lys Lys Val Lys
            820                 825                 830
Ser Gln Ser Lys Met Ala Ser Lys Ala Lys Lys Ile Phe Ala Glu Tyr
        835                 840                 845
Ile Ala Ile Gln Ala Cys Lys Glu Val Asn Leu Asp Ser Tyr Thr Arg
850                 855                 860
Glu His Thr Lys Asp Asn Leu Gln Ser Val Thr Arg Gly Cys Phe Asp
865                 870                 875                 880
Leu Ala Gln Lys Arg Ile Phe Gly Leu Met Glu Lys Asp Ser Tyr Pro
                885                 890                 895
Arg Phe Leu Arg Ser Asp Leu Tyr Leu Asp Leu Ile Asn Gln Lys Lys
            900                 905                 910
Met Ser Pro Pro Leu
        915

<210> SEQ ID NO 9
<211> LENGTH: 1560
<212> TYPE: DNA
<213> ORGANISM: Homo Sapiens

<400> SEQUENCE: 9
atgtttgaga cggaggcaga tgagaagagg gagatggcct tggaggaagg gaagggggcct    60 ggtgccgagg attccccacc cagcaaggag ccctctcctg gccaggagct tcctccagga   120
caagaccttc cacccaacaa ggactcccct tctgggcagg aacccgctcc cagccaagaa   180
ccactgtcca gcaaagactc agctacctct gaaggatccc ctccaggccc agatgctccg   240
cccagcaagg atgtgccacc atgccaggaa cccctccag cccaagacct ctcaccctgc   300
caggacctac ctgctggtca gaacccctg cctcaccagg accctctact caccaaagac   360
ctccctgcca tccaggaatc ccccacccgg gaccttccac cctgtcaaga tctgcctcct   420
agccaggtct ccctgccagc caaggccctt actgaggaca ccatgagctc cggggaccta   480
ctagcagcta ctggggaccc acctgcggcc ccaggccag ccttcgtgat ccctgaggtc   540
cggctggata gcacctacag ccagaaggca ggggcagagc agggctgctc gggagatgag   600
gaggatgcag aagaggccga ggaggtggag gaggggaggg aagggggagga ggacgaggat   660 gaggacacca gcgatgacaa ctacggagag cgcagtgagg ccaagcgcag cagcatgatc   720 gagacggcc agggggctga gggtggcctc tcactgcgtg tgcagaactc gctgcggcgc   780
```

```
cggacgcaca gcgagggcag cctgctgcag gagccccgag ggccctgctt tgcctccgac      840
accaccttgc actgctcaga cggtgagggc gccgcctcca cctggggcat gccttcgccc      900
agcaccctca agaaagagct gggccgcaat ggtggctcca tgcaccacct ttccctcttc      960
ttcacaggac acaggaagat gagcggggct gacaccgttg gggatgatga cgaagcctcc     1020
cggaagagaa agagcaaaaa cctagccaag gacatgaaga caagctggg atcttcaga      1080 cggcggaatg agtcccctgg agcccctccc gcgggcaagg cagacaaaat gatgaagtca     1140
ttcaagccca cctcagagga agccctcaag tggggcgagt ccttggagaa gctgctggtt     1200
cacaaatacg ggttagcagt gttccaagcc ttccttcgca ctgagttcag tgaggagaat     1260
ctggagttct ggttggcttg tgaggacttc aagaaggtca agtcacagtc caagatggca     1320
tccaaggcca agaagatctt tgctgaatac atcgcgatcc aggcatgcaa ggaggtcaac     1380
ctggactcct acacgcggga gcacaccaag gacaacctgc agagcgtcac gcggggctgc     1440
ttcgacctgg cacagaagcg catcttcggg ctcatggaaa aggactcgta ccctcgcttt     1500
ctccgttctg acctctacct ggaccttatt aaccagaaga gatgagtcc cccgctttag     1560
```

<210> SEQ ID NO 10
<211> LENGTH: 519
<212> TYPE: PRT
<213> ORGANISM: Homo Sapiens

<400> SEQUENCE: 10

```
Met Phe Glu Thr Glu Ala Asp Glu Lys Arg Glu Met Ala Leu Glu Glu
1               5                   10                  15

Gly Lys Gly Pro Gly Ala Glu Asp Ser Pro Ser Lys Glu Pro Ser
                20                  25                  30

Pro Gly Gln Glu Leu Pro Pro Gly Gln Asp Leu Pro Pro Asn Lys Asp
            35                  40                  45

Ser Pro Ser Gly Gln Glu Pro Ala Pro Ser Gln Glu Pro Leu Ser Ser
        50                  55                  60

Lys Asp Ser Ala Thr Ser Glu Gly Ser Pro Pro Gly Pro Asp Ala Pro
65                  70                  75                  80

Pro Ser Lys Asp Val Pro Pro Cys Gln Glu Pro Pro Ala Gln Asp
                85                  90                  95

Leu Ser Pro Cys Gln Asp Leu Pro Ala Gly Gln Glu Pro Leu Pro His
            100                 105                 110

Gln Asp Pro Leu Leu Thr Lys Asp Leu Pro Ala Ile Gln Glu Ser Pro
        115                 120                 125

Thr Arg Asp Leu Pro Pro Cys Gln Asp Leu Pro Pro Ser Gln Val Ser
    130                 135                 140

Leu Pro Ala Lys Ala Leu Thr Glu Asp Thr Met Ser Ser Gly Asp Leu
145                 150                 155                 160

Leu Ala Ala Thr Gly Asp Pro Ala Ala Pro Arg Pro Ala Phe Val
                165                 170                 175

Ile Pro Glu Val Arg Leu Asp Ser Thr Tyr Ser Gln Lys Ala Gly Ala
            180                 185                 190

Glu Gln Gly Cys Ser Gly Asp Glu Glu Ala Glu Glu Ala Glu Glu
        195                 200                 205

Val Glu Glu Gly Glu Glu Gly Glu Glu Asp Glu Asp Glu Asp Thr Ser
    210                 215                 220

Asp Asp Asn Tyr Gly Glu Arg Ser Glu Ala Lys Arg Ser Ser Met Ile
225                 230                 235                 240
```

Glu Thr Gly Gln Gly Ala Glu Gly Gly Leu Ser Leu Arg Val Gln Asn
                    245                 250                 255

Ser Leu Arg Arg Arg Thr His Ser Glu Gly Ser Leu Leu Gln Glu Pro
            260                 265                 270

Arg Gly Pro Cys Phe Ala Ser Asp Thr Thr Leu His Cys Ser Asp Gly
        275                 280                 285

Glu Gly Ala Ala Ser Thr Trp Gly Met Pro Ser Pro Ser Thr Leu Lys
    290                 295                 300

Lys Glu Leu Gly Arg Asn Gly Gly Ser Met His His Leu Ser Leu Phe
305                 310                 315                 320

Phe Thr Gly His Arg Lys Met Ser Gly Ala Asp Thr Val Gly Asp Asp
                    325                 330                 335

Asp Glu Ala Ser Arg Lys Arg Lys Ser Lys Asn Leu Ala Lys Asp Met
                340                 345                 350

Lys Asn Lys Leu Gly Ile Phe Arg Arg Arg Asn Glu Ser Pro Gly Ala
            355                 360                 365

Pro Pro Ala Gly Lys Ala Asp Lys Met Met Lys Ser Phe Lys Pro Thr
        370                 375                 380

Ser Glu Glu Ala Leu Lys Trp Gly Glu Ser Leu Glu Lys Leu Leu Val
385                 390                 395                 400

His Lys Tyr Gly Leu Ala Val Phe Gln Ala Phe Leu Arg Thr Glu Phe
                    405                 410                 415

Ser Glu Glu Asn Leu Glu Phe Trp Leu Ala Cys Glu Asp Phe Lys Lys
                420                 425                 430

Val Lys Ser Gln Ser Lys Met Ala Ser Lys Ala Lys Lys Ile Phe Ala
            435                 440                 445

Glu Tyr Ile Ala Ile Gln Ala Cys Lys Glu Val Asn Leu Asp Ser Tyr
        450                 455                 460

Thr Arg Glu His Thr Lys Asp Asn Leu Gln Ser Val Thr Arg Gly Cys
465                 470                 475                 480

Phe Asp Leu Ala Gln Lys Arg Ile Phe Gly Leu Met Glu Lys Asp Ser
                    485                 490                 495

Tyr Pro Arg Phe Leu Arg Ser Asp Leu Tyr Leu Asp Leu Ile Asn Gln
                500                 505                 510

Lys Lys Met Ser Pro Pro Leu
        515

<210> SEQ ID NO 11
<211> LENGTH: 1809
<212> TYPE: DNA
<213> ORGANISM: Homo Sapiens

<400> SEQUENCE: 11
atggagcgct ccctgcaccg cgtctccctc gggagccggc gtgcccaccc ggacttgtcc      60
ttctacctca ccacctttgg tcagctgagg ctgtccattg atgcccagga ccgggttctg     120
ctgcttcaca ttatagaagg taaaggcctg atcagcaaac agcctggcac ctgtgatccg     180
tatgtgaaga tttctttgat ccctgaagat agtagactac gccaccagaa gacgcagacc     240
gttccagact gcagagaccc ggctttccac gagcacttct ctttcctgt ccaagaggag      300 gatgatcaga agcgtctctt ggttactgtg tggaacaggg ccagccagtc cagacagagt     360
ggactcattg gctgcatgag ctttggggtg aagtctctcc tgactccaga caaggagatc     420
agtggttggt actacctcct aggggagcac ctgggccgga ccaagcactt gaaggtggcc     480

| | | | | |
|---|---|---|---|---|
| aggcggcgac | tgcggccgct | gagagacccg | ctgctgagaa | tgccaggagg tggggacact | 540 |
| gagaatggga | agaaactaaa | gatcaccatc | ccgaggggaa | aggacggctt tggcttcacc | 600 |
| atctgctgcg | actctccagt | tcgagtccag | gccgtggatt | ccggggtcc ggcggaacgg | 660 |
| gcagggctgc | agcagctgga | cacggtgctg | cagctgaatg | agaggcctgt ggagcactgg | 720 |
| aaatgtgtgg | agctggccca | cgagatccgg | agctgcccca | gtgagatcat cctactcgtg | 780 |
| tggcgcatgg | tcccccaggt | caagccagga | ccagatggcg | gggtcctgcg gcgggcctcc | 840 |
| tgcaagtcga | cacatgacct | ccagtcaccc | cccaacaaac | gggagaagaa ctgcacccat | 900 |
| ggggtccagg | cacggcctga | gcagcgccac | agctgccacc | tggtatgtga cagctctgat | 960 |
| gggctgctgc | tcggcggctg | ggagcgctac | accgaggtgg | ccaagcgcgg gggccagcac | 1020 |
| accctgcctg | cactgtcccg | tgccactgcc | ccaccgacc | ccaactacat catcctggcc | 1080 |
| ccgctgaatc | ctgggagcca | gctgctccgg | cctgtgtacc | aggaggatac catccccgaa | 1140 |
| gaatcaggga | gtcccagtaa | agggaagtcc | tacacaggcc | tggggaagaa gtcccggctg | 1200 |
| atgaagacag | tgcagaccat | gaagggccac | gggaactacc | aaaactgccc ggttgtgagg | 1260 |
| ccgcatgcca | cgcactcaag | ctatggcacc | tacgtcaccc | tggcccccaa agtcctggtg | 1320 |
| ttccctgtct | ttgttcagcc | tctagatctc | tgtaatcctg | cccggaccct cctgctgtca | 1380 |
| gaggagctgc | tgctgtatga | agggaggaac | aaggctgccg | aggtgacact gtttgcctat | 1440 |
| tcggacctgc | tgctcttcac | caaggaggac | gagcctggcc | gctgcgacgt cctgaggaac | 1500 |
| cccctctacc | tccagagtgt | gaagctgcag | gaaggttctt | cagaagacct gaaattctgc | 1560 |
| gtgctctatc | tagcagagaa | ggcagagtgc | ttattcactt | tggaagcgca ctcgcaggag | 1620 |
| cagaagaaga | gagtgtgctg | gtgcctgtcg | gagaacatcg | ccaagcagca acagctggca | 1680 |
| gcatcacccc | cggacagcaa | gaaactccac | cctttcgggct | ctctccagca ggagatgggg | 1740 |
| ccggtcaact | caaccaatgc | cacccaggat | agaagcttta | cctcaccagg acagactctg | 1800 |
| attggctga | | | | | 1809 |

<210> SEQ ID NO 12
<211> LENGTH: 602
<212> TYPE: PRT
<213> ORGANISM: Homo Sapiens

<400> SEQUENCE: 12

Met Glu Arg Ser Leu His Arg Val Ser Leu Gly Ser Arg Arg Ala His
1               5                   10                  15

Pro Asp Leu Ser Phe Tyr Leu Thr Thr Phe Gly Gln Leu Arg Leu Ser
            20                  25                  30

Ile Asp Ala Gln Asp Arg Val Leu Leu Leu His Ile Ile Glu Gly Lys
        35                  40                  45

Gly Leu Ile Ser Lys Gln Pro Gly Thr Cys Asp Pro Tyr Val Lys Ile
    50                  55                  60

Ser Leu Ile Pro Glu Asp Ser Arg Leu Arg His Gln Lys Thr Gln Thr
65                  70                  75                  80

Val Pro Asp Cys Arg Asp Pro Ala Phe His Glu His Phe Phe Phe Pro
                85                  90                  95

Val Gln Glu Glu Asp Asp Gln Lys Arg Leu Leu Val Thr Val Trp Asn
            100                 105                 110

Arg Ala Ser Gln Ser Arg Gln Ser Gly Leu Ile Gly Cys Met Ser Phe
        115                 120                 125

Gly Val Lys Ser Leu Leu Thr Pro Asp Lys Glu Ile Ser Gly Trp Tyr

```
            130                 135                 140
Tyr Leu Leu Gly Glu His Leu Gly Arg Thr Lys His Leu Lys Val Ala
145                 150                 155                 160

Arg Arg Arg Leu Arg Pro Leu Arg Asp Pro Leu Leu Arg Met Pro Gly
                165                 170                 175

Gly Gly Asp Thr Glu Asn Gly Lys Lys Leu Lys Ile Thr Ile Pro Arg
                180                 185                 190

Gly Lys Asp Gly Phe Gly Phe Thr Ile Cys Cys Asp Ser Pro Val Arg
                195                 200                 205

Val Gln Ala Val Asp Ser Gly Gly Pro Ala Glu Arg Ala Gly Leu Gln
        210                 215                 220

Gln Leu Asp Thr Val Leu Gln Leu Asn Glu Arg Pro Val Glu His Trp
225                 230                 235                 240

Lys Cys Val Glu Leu Ala His Glu Ile Arg Ser Cys Pro Ser Glu Ile
                245                 250                 255

Ile Leu Leu Val Trp Arg Met Val Pro Gln Val Lys Pro Gly Pro Asp
                260                 265                 270

Gly Gly Val Leu Arg Arg Ala Ser Cys Lys Ser Thr His Asp Leu Gln
                275                 280                 285

Ser Pro Pro Asn Lys Arg Glu Lys Asn Cys Thr His Gly Val Gln Ala
        290                 295                 300

Arg Pro Glu Gln Arg His Ser Cys His Leu Val Cys Asp Ser Ser Asp
305                 310                 315                 320

Gly Leu Leu Leu Gly Gly Trp Glu Arg Tyr Thr Glu Val Ala Lys Arg
                325                 330                 335

Gly Gly Gln His Thr Leu Pro Ala Leu Ser Arg Ala Thr Ala Pro Thr
                340                 345                 350

Asp Pro Asn Tyr Ile Ile Leu Ala Pro Leu Asn Pro Gly Ser Gln Leu
                355                 360                 365

Leu Arg Pro Val Tyr Gln Glu Asp Thr Ile Pro Glu Glu Ser Gly Ser
        370                 375                 380

Pro Ser Lys Gly Lys Ser Tyr Thr Gly Leu Gly Lys Lys Ser Arg Leu
385                 390                 395                 400

Met Lys Thr Val Gln Thr Met Lys Gly His Gly Asn Tyr Gln Asn Cys
                405                 410                 415

Pro Val Val Arg Pro His Ala Thr His Ser Ser Tyr Gly Thr Tyr Val
                420                 425                 430

Thr Leu Ala Pro Lys Val Leu Val Phe Pro Val Phe Val Gln Pro Leu
                435                 440                 445

Asp Leu Cys Asn Pro Ala Arg Thr Leu Leu Leu Ser Glu Glu Leu Leu
        450                 455                 460

Leu Tyr Glu Gly Arg Asn Lys Ala Ala Glu Val Thr Leu Phe Ala Tyr
465                 470                 475                 480

Ser Asp Leu Leu Leu Phe Thr Lys Glu Asp Glu Pro Gly Arg Cys Asp
                485                 490                 495

Val Leu Arg Asn Pro Leu Tyr Leu Gln Ser Val Lys Leu Gln Glu Gly
                500                 505                 510

Ser Ser Glu Asp Leu Lys Phe Cys Val Leu Tyr Leu Ala Glu Lys Ala
        515                 520                 525

Glu Cys Leu Phe Thr Leu Glu Ala His Ser Gln Glu Gln Lys Lys Arg
        530                 535                 540

Val Cys Trp Cys Leu Ser Glu Asn Ile Ala Lys Gln Gln Gln Leu Ala
545                 550                 555                 560
```

```
Ala Ser Pro Pro Asp Ser Lys Lys Leu His Pro Phe Gly Ser Leu Gln
            565                 570                 575

Gln Glu Met Gly Pro Val Asn Ser Thr Asn Ala Thr Gln Asp Arg Ser
        580                 585                 590

Phe Thr Ser Pro Gly Gln Thr Leu Ile Gly
        595                 600
```

<210> SEQ ID NO 13
<211> LENGTH: 507
<212> TYPE: DNA
<213> ORGANISM: Homo Sapiens

<400> SEQUENCE: 13

```
atgaagaaca agctggggat cttcagacgg cggaatgagt ccccctggagc ccctcccgcg    60
ggcaaggcag acaaaatgat gaagtcattc aagcccacct cagaggaagc cctcaagtgg   120
ggcgagtcct tggagaagct gctggttcac aaatacgggt tagcagtgtt ccaagccttc   180
cttcgcactg agttcagtga ggagaatctg gagttctggt tggcttgtga ggacttcaag   240
aaggtcaagt cacagtccaa gatggcatcc aaggccaaga agatctttgc tgaatacatc   300
gcgatccagg catgcaagga ggtcaacctg gactcctaca cgcgggagca caccaaggac   360
aacctgcaga gcgtcacgcg gggctgcttc gacctggcac agaagcgcat cttcgggctc   420
atggaaaagg actcgtaccc tcgctttctc cgttctgacc tctacctgga ccttattaac   480
cagaagaaga tgagtccccc gctttag                                        507
```

<210> SEQ ID NO 14
<211> LENGTH: 168
<212> TYPE: PRT
<213> ORGANISM: Homo Sapiens

<400> SEQUENCE: 14

```
Met Lys Asn Lys Leu Gly Ile Phe Arg Arg Arg Asn Glu Ser Pro Gly
1               5                   10                  15

Ala Pro Pro Ala Gly Lys Ala Asp Lys Met Met Lys Ser Phe Lys Pro
            20                  25                  30

Thr Ser Glu Glu Ala Leu Lys Trp Gly Glu Ser Leu Glu Lys Leu Leu
        35                  40                  45

Val His Lys Tyr Gly Leu Ala Val Phe Gln Ala Phe Leu Arg Thr Glu
    50                  55                  60

Phe Ser Glu Glu Asn Leu Glu Phe Trp Leu Ala Cys Glu Asp Phe Lys
65                  70                  75                  80

Lys Val Lys Ser Gln Ser Lys Met Ala Ser Lys Ala Lys Lys Ile Phe
                85                  90                  95

Ala Glu Tyr Ile Ala Ile Gln Ala Cys Lys Glu Val Asn Leu Asp Ser
            100                 105                 110

Tyr Thr Arg Glu His Thr Lys Asp Asn Leu Gln Ser Val Thr Arg Gly
        115                 120                 125

Cys Phe Asp Leu Ala Gln Lys Arg Ile Phe Gly Leu Met Glu Lys Asp
    130                 135                 140

Ser Tyr Pro Arg Phe Leu Arg Ser Asp Leu Tyr Leu Asp Leu Ile Asn
145                 150                 155                 160

Gln Lys Lys Met Ser Pro Pro Leu
                165
```

<210> SEQ ID NO 15

<211> LENGTH: 936
<212> TYPE: DNA
<213> ORGANISM: Homo Sapiens

<400> SEQUENCE: 15

```
atggtaacga ggaggccagt cacaaatagc tgggactggc ttcctgccgg ggcggcccca    60
gaggctgtcc cttgcagaca catgccccctt tcacggctcc ctctcagggt tggccagaag   120
gaattttttt ttccgctccc cctcctggtc cctcccattt cctggctcct cctgtctgag   180
tcccagcccc ggcttgtgcc tgggagtcca gtcatcaggc caggattcca gagagcgtgt   240
gtggctgcag cctgcaccgt tgctgcccgc tgcccaggac gcggggtggg ggacaggagc   300
cagagtggtg cctcctacag accaatctgc ggccccaagg tgggggggccc tacagagatg   360
ctccgaggca tgtacctcac tcgcaacggg aacctgcaga ggcgacacac gatgaaggaa   420
gccaaggaca tgaagaacaa gctggggatc ttcagacggc ggaatgagtc ccctggagcc   480
cctcccgcgg gcaaggcaga caaaatgatg aagtcattca gcccacctc agaggaagcc    540
ctcaagtggg gcgagtcctt ggagaagctg ctggttcaca atacgggtt agcagtgttc    600
caagccttcc ttcgcactga gttcagtgag gagaatctgg agttctggtt ggcttgtgag   660
gacttcaaga aggtcaagtc acagtccaag atggcatcca aggccaagaa gatctttgct   720
gaatacatcg cgatccaggc atgcaaggag gtcaacctgg actcctacac gcgggagcac   780
accaaggaca acctgcagag cgtcacgcgg ggctgcttcg acctggcaca gaagcgcatc   840
ttcgggctca tggaaaagga ctcgtaccct cgctttctcc gttctgacct ctacctggac   900
cttattaacc agaagaagat gagtcccccg ctttag                             936
```

<210> SEQ ID NO 16
<211> LENGTH: 311
<212> TYPE: PRT
<213> ORGANISM: Homo Sapiens

<400> SEQUENCE: 16

```
Met Val Thr Arg Arg Pro Val Thr Asn Ser Trp Asp Trp Leu Pro Ala
1               5                   10                  15

Gly Ala Ala Pro Glu Ala Val Pro Cys Arg His Met Pro Leu Ser Arg
            20                  25                  30

Leu Pro Leu Arg Val Gly Gln Lys Glu Phe Phe Pro Leu Pro Leu
        35                  40                  45

Leu Val Pro Pro Ile Ser Trp Leu Leu Leu Ser Glu Ser Gln Pro Arg
    50                  55                  60

Leu Val Pro Gly Ser Pro Val Ile Arg Pro Gly Phe Gln Arg Ala Cys
65                  70                  75                  80

Val Ala Ala Ala Cys Thr Val Ala Arg Cys Pro Gly Arg Gly Val
                85                  90                  95

Gly Asp Arg Ser Gln Ser Gly Ala Ser Tyr Arg Pro Ile Cys Gly Pro
            100                 105                 110

Lys Val Gly Gly Pro Thr Glu Met Leu Arg Gly Met Tyr Leu Thr Arg
        115                 120                 125

Asn Gly Asn Leu Gln Arg Arg His Thr Met Lys Glu Ala Lys Asp Met
    130                 135                 140

Lys Asn Lys Leu Gly Ile Phe Arg Arg Arg Asn Glu Ser Pro Gly Ala
145                 150                 155                 160

Pro Pro Ala Gly Lys Ala Asp Lys Met Met Lys Ser Phe Lys Pro Thr
                165                 170                 175
```

```
Ser Glu Glu Ala Leu Lys Trp Gly Glu Ser Leu Glu Lys Leu Leu Val
            180                 185                 190

His Lys Tyr Gly Leu Ala Val Phe Gln Ala Phe Leu Arg Thr Glu Phe
        195                 200                 205

Ser Glu Glu Asn Leu Glu Phe Trp Leu Ala Cys Glu Asp Phe Lys Lys
    210                 215                 220

Val Lys Ser Gln Ser Lys Met Ala Ser Lys Ala Lys Lys Ile Phe Ala
225                 230                 235                 240

Glu Tyr Ile Ala Ile Gln Ala Cys Lys Glu Val Asn Leu Asp Ser Tyr
                245                 250                 255

Thr Arg Glu His Thr Lys Asp Asn Leu Gln Ser Val Thr Arg Gly Cys
            260                 265                 270

Phe Asp Leu Ala Gln Lys Arg Ile Phe Gly Leu Met Glu Lys Asp Ser
        275                 280                 285

Tyr Pro Arg Phe Leu Arg Ser Asp Leu Tyr Leu Asp Leu Ile Asn Gln
    290                 295                 300

Lys Lys Met Ser Pro Pro Leu
305                 310

<210> SEQ ID NO 17
<211> LENGTH: 3597
<212> TYPE: DNA
<213> ORGANISM: Homo Sapiens

<400> SEQUENCE: 17
atgcctgtaa tcccagcact tgggaggtt gagatgggca gatcgcaagg tcaggagatc      60
gagaccatcc tggctaacag gtcacattca gacagcacac ctttgcccaa ttttctttct    120
ggatctcacc gtcctgagtg ttgtacctgc aggttgctca cagcctctgg agcccaagat    180
agtctcccct ttgggaggag gctctacagt ggtccctggc gaagttgtga agaggtctgc    240
cacgtctctg tgctcagtgt cctctctaca tcctgtggct tgagcctgag cttgcccata    300
ttccctggct ggatggagtg gctaagccct gatatcgctc tgcccagaag agatgagtgg    360
actcaaactt ctccagccag gaagaggatc acgcatgcca agtccagggt gcaggtcag    420 ctgaggctgt ccattgatgc ccaggaccgg ttctgctgc ttcacattat agaaggtaaa    480
ggcctgatca gcaaacagcc tggcacctgt gatccgtatg tgaagatttc tttgatccct    540
gaagatagta gactacgcca ccagaagacg cagaccgttc cagactgcag agacccggct    600
ttccacgagc acttcttctt tcctgtccaa gaggaggatg atcagaagcg tctcttggtt    660
actgtgtgga cagggccag ccagtccaga cagagtggac tcattggctg catgagcttt    720
ggggtgaagt ctctcctgac tccagacaag gagatcagtg ttggtacta cctcctaggg    780 gagcacctgg gccggaccaa gcacttgaag gtggccaggc ggcgactgcg gccgctgaga    840
gacccgctgc tgagaatgcc aggaggtggg gacactgaga atgggaagaa actaaagatc    900
accatcccga ggggaaagga cggctttggc ttcaccatct gctgcgactc tccagttcga    960
gtccaggccg tggattccgg gggtccggcg gaacgggcag ggctgcagca gctggacacg   1020
gtgctgcagc tgaatgagag gcctgtggag cactggaaat gtgtggagct ggcccacgag   1080
atccggagct gccccagtga gatcatccta tcgtgtggc gcatggtccc ccaggtcaag   1140
ccaggaccag atggcggggt cctgcggcgg gcctcctgca agtcgacaca tgacctccag   1200 tcaccccca acaaacggga gaagaactgc acccatgggg tccaggcacg gcctgagcag   1260
cgccacagct gccacctggt atgtgacagc tctgatgggc tgctgtcgg cggctgggag   1320
```

```
cgctacaccg aggtggccaa gcgcggggggc cagcacaccc tgcctgcact gtcccgtgcc   1380
actgccccca ccgaccccaa ctacatcatc ctggccccgc tgaatcctgg gagccagctg   1440
ctccggcctg tgtaccagga ggataccatc cccgaagaat cagggagtcc cagtaaaggg   1500
aagtcctaca caggcctggg gaagaagtcc cggctgatga agacagtgca gaccatgaag   1560
ggccacggga actaccaaaa ctgcccggtt gtgaggccgc atgccacgca ctcaagctat   1620
ggcacctacg tcaccctggc ccccaaagtc ctggtgttcc ctgtctttgt tcagcctcta   1680
gatctctgta atcctgcccg accctcctg ctgtcagagg agctgctgct gtatgaaggg   1740
aggaacaagg ctgccgaggt gacactgttt gcctattcgg acctgctgct cttcaccaag   1800
gaggacgagc ctggccgctg cgacgtcctg aggaaccccc tctacctcca gagtgtgaag   1860
ctgcaggaag gttcttcaga agacctgaaa ttctgcgtgc tctatctagc agagaaggca   1920
gagtgcttat tcactttgga agcgcactcg caggagcaga agaagagagt gtgctggtgc   1980
ctgtcggaga acatcgccaa gcagcaacag ctggcagcat caccccggca cagcaagatg   2040
tttgagacgg aggcagatga aagagggag atggccttgg aggaagggaa ggggcctggt   2100
gccgaggatt ccccacccag caaggagccc tctcctggcc aggagcttcc tccaggacaa   2160
gaccttccac ccaacaagga ctccccttct gggcaggaac ccgctcccag ccaagaacca   2220
ctgtccagca aagactcagc tacctctgaa ggatcccctc caggcccaga tgctccgccc   2280
agcaaggatg tgccaccatg ccaggaaccc cctccagccc aagacctctc accctgccag   2340
gacctacctg ctggtcaaga acccctgcct caccaggacc ctctactcac caaagacctc   2400
cctgccatcc aggaatcccc cacccgggac cttccaccct gtcaagatct gcctcctagc   2460
caggtctccc tgccagccaa ggcccttact gaggacacca tgagctccgg ggacctacta   2520
gcagctactg ggaccccacc tgcggccccc aggccagcct tcgtgatccc tgaggtccgg   2580
ctggatagca cctacagcca gaaggcaggg gcagagcagg gctgctcggg agatgaggag   2640
gatgcagaaq aggccgagga ggtggaggag ggggaggaag gggaggagga cgaggatgag   2700
gacaccagcg atgacaacta cggagagcgc agtgaggcca agcgcagcag catgatcgag   2760
acgggccagg gggctgaggg tggcctctca ctgcgtgtgc agaactcgct gcggcgccgg   2820
acgcacagcg agggcagcct gctgcaggag ccccgagggc cctgctttgc ctccgacacc   2880
accttgcact gctcagacgg tgagggcgcc gcctccacct ggggcatgcc ttcgcccagc   2940
accctcaaga aagagctggg ccgcaatggt ggctccatgc accacctttc cctcttcttc   3000
acaggacaca ggaagatgag cggggctgac accgttgggg atgatgacga agcctcccgg   3060
aagagaaaga gcaaaaacct agccaaggac atgaagaaca agctggggat cttcagacgg   3120
cggaatgagt cccctggagc ccctcccgcg ggcaaggcag acaaaatgat gaagtcattc   3180
aagcccacct cagaggaagc cctcaagtgg ggcgagtcct tggagaagct gctggttcac   3240
aaatacgggt tagcagtgtt ccaagccttc cttcgcactg agttcagtga ggagaatctg   3300
gagttctggt tggcttgtga ggacttcaag aaggtcaagt cacagtccaa gatggcatcc   3360
aaggccaaga gatctttgc tgaatacatc gcgatccagg catgcaagga ggtcaacctg   3420
gactcctaca cgcggggagca caccaaggac aaccctcaga gcgtcacgcg gggctgcttc   3480
gacctggcac agaagcgcat cttcgggctc atggaaaagg actcgtaccc tcgctttctc   3540
cgttctgacc tctacctgga ccttattaac cagaagaaga tgagtccccc gctttag    3597
```

<210> SEQ ID NO 18
<211> LENGTH: 1198

-continued

```
<212> TYPE: PRT
<213> ORGANISM: Homo Sapiens

<400> SEQUENCE: 18

Met Pro Val Ile Pro Ala Leu Trp Glu Val Glu Met Gly Arg Ser Gln
1               5                   10                  15

Gly Gln Glu Ile Glu Thr Ile Leu Ala Asn Arg Ser His Ser Asp Ser
                20                  25                  30

Thr Pro Leu Pro Asn Phe Leu Ser Gly Ser His Arg Pro Glu Cys Cys
        35                  40                  45

Thr Cys Arg Leu Leu Thr Ala Ser Gly Ala Gln Asp Ser Leu Pro Phe
50                  55                  60

Gly Arg Arg Leu Tyr Ser Gly Pro Trp Arg Ser Cys Glu Glu Val Cys
65                  70                  75                  80

His Val Ser Val Leu Ser Val Leu Ser Thr Ser Cys Gly Leu Ser Leu
                85                  90                  95

Ser Leu Pro Ile Phe Pro Gly Trp Met Glu Trp Leu Ser Pro Asp Ile
                100                 105                 110

Ala Leu Pro Arg Arg Asp Glu Trp Thr Gln Thr Ser Pro Ala Arg Lys
            115                 120                 125

Arg Ile Thr His Ala Lys Val Gln Gly Ala Gly Gln Leu Arg Leu Ser
        130                 135                 140

Ile Asp Ala Gln Asp Arg Val Leu Leu Leu His Ile Ile Glu Gly Lys
145                 150                 155                 160

Gly Leu Ile Ser Lys Gln Pro Gly Thr Cys Asp Pro Tyr Val Lys Ile
                165                 170                 175

Ser Leu Ile Pro Glu Asp Ser Arg Leu Arg His Gln Lys Thr Gln Thr
                180                 185                 190

Val Pro Asp Cys Arg Asp Pro Ala Phe His Glu His Phe Phe Phe Pro
            195                 200                 205

Val Gln Glu Glu Asp Asp Gln Lys Arg Leu Leu Val Thr Val Trp Asn
        210                 215                 220

Arg Ala Ser Gln Ser Arg Gln Ser Gly Leu Ile Gly Cys Met Ser Phe
225                 230                 235                 240

Gly Val Lys Ser Leu Leu Thr Pro Asp Lys Glu Ile Ser Gly Trp Tyr
                245                 250                 255

Tyr Leu Leu Gly Glu His Leu Gly Arg Thr Lys His Leu Lys Val Ala
                260                 265                 270

Arg Arg Arg Leu Arg Pro Leu Arg Asp Pro Leu Leu Arg Met Pro Gly
            275                 280                 285

Gly Gly Asp Thr Glu Asn Gly Lys Lys Leu Lys Ile Thr Ile Pro Arg
        290                 295                 300

Gly Lys Asp Gly Phe Gly Phe Thr Ile Cys Cys Asp Ser Pro Val Arg
305                 310                 315                 320

Val Gln Ala Val Asp Ser Gly Gly Pro Ala Glu Arg Ala Gly Leu Gln
                325                 330                 335

Gln Leu Asp Thr Val Leu Gln Leu Asn Glu Arg Pro Val Glu His Trp
                340                 345                 350

Lys Cys Val Glu Leu Ala His Glu Ile Arg Ser Cys Pro Ser Glu Ile
            355                 360                 365

Ile Leu Leu Val Trp Arg Met Val Pro Gln Val Lys Pro Gly Pro Asp
        370                 375                 380

Gly Gly Val Leu Arg Arg Ala Ser Cys Lys Ser Thr His Asp Leu Gln
385                 390                 395                 400
```

```
Ser Pro Pro Asn Lys Arg Glu Lys Asn Cys Thr His Gly Val Gln Ala
            405                 410                 415

Arg Pro Glu Gln Arg His Ser Cys His Leu Val Cys Asp Ser Ser Asp
        420                 425                 430

Gly Leu Leu Leu Gly Gly Trp Glu Arg Tyr Thr Glu Val Ala Lys Arg
            435                 440                 445

Gly Gly Gln His Thr Leu Pro Ala Leu Ser Arg Ala Thr Ala Pro Thr
450                 455                 460

Asp Pro Asn Tyr Ile Ile Leu Ala Pro Leu Asn Pro Gly Ser Gln Leu
465                 470                 475                 480

Leu Arg Pro Val Tyr Gln Glu Asp Thr Ile Pro Glu Glu Ser Gly Ser
                485                 490                 495

Pro Ser Lys Gly Lys Ser Tyr Thr Gly Leu Gly Lys Lys Ser Arg Leu
                500                 505                 510

Met Lys Thr Val Gln Thr Met Lys Gly His Gly Asn Tyr Gln Asn Cys
            515                 520                 525

Pro Val Val Arg Pro His Ala Thr His Ser Ser Tyr Gly Thr Tyr Val
            530                 535                 540

Thr Leu Ala Pro Lys Val Leu Val Phe Pro Val Phe Val Gln Pro Leu
545                 550                 555                 560

Asp Leu Cys Asn Pro Ala Arg Thr Leu Leu Leu Ser Glu Glu Leu Leu
                565                 570                 575

Leu Tyr Glu Gly Arg Asn Lys Ala Ala Glu Val Thr Leu Phe Ala Tyr
                580                 585                 590

Ser Asp Leu Leu Leu Phe Thr Lys Glu Asp Glu Pro Gly Arg Cys Asp
            595                 600                 605

Val Leu Arg Asn Pro Leu Tyr Leu Gln Ser Val Lys Leu Gln Glu Gly
            610                 615                 620

Ser Ser Glu Asp Leu Lys Phe Cys Val Leu Tyr Leu Ala Glu Lys Ala
625                 630                 635                 640

Glu Cys Leu Phe Thr Leu Glu Ala His Ser Gln Gln Lys Lys Arg
                645                 650                 655

Val Cys Trp Cys Leu Ser Glu Asn Ile Ala Lys Gln Gln Leu Ala
            660                 665                 670

Ala Ser Pro Pro Asp Ser Lys Met Phe Glu Thr Glu Ala Asp Glu Lys
                675                 680                 685

Arg Glu Met Ala Leu Glu Glu Gly Lys Gly Pro Gly Ala Glu Asp Ser
        690                 695                 700

Pro Pro Ser Lys Glu Pro Ser Pro Gly Gln Glu Leu Pro Pro Gly Gln
705                 710                 715                 720

Asp Leu Pro Pro Asn Lys Asp Ser Pro Ser Gly Gln Glu Pro Ala Pro
                725                 730                 735

Ser Gln Glu Pro Leu Ser Ser Lys Asp Ser Ala Thr Ser Glu Gly Ser
            740                 745                 750

Pro Pro Gly Pro Asp Ala Pro Pro Ser Lys Asp Val Pro Pro Cys Gln
            755                 760                 765

Glu Pro Pro Pro Ala Gln Asp Leu Ser Pro Cys Gln Asp Leu Pro Ala
        770                 775                 780

Gly Gln Glu Pro Leu Pro His Gln Asp Pro Leu Leu Thr Lys Asp Leu
785                 790                 795                 800

Pro Ala Ile Gln Glu Ser Pro Thr Arg Asp Leu Pro Pro Cys Gln Asp
                805                 810                 815
```

-continued

Leu Pro Pro Ser Gln Val Ser Leu Pro Ala Lys Ala Leu Thr Glu Asp
    820                 825                 830

Thr Met Ser Ser Gly Asp Leu Leu Ala Ala Thr Gly Asp Pro Pro Ala
835                 840                 845

Ala Pro Arg Pro Ala Phe Val Ile Pro Glu Val Arg Leu Asp Ser Thr
850                 855                 860

Tyr Ser Gln Lys Ala Gly Ala Glu Gln Gly Cys Ser Gly Asp Glu Glu
865                 870                 875                 880

Asp Ala Glu Glu Ala Glu Val Glu Gly Glu Gly Glu
            885                 890                 895

Asp Glu Asp Glu Asp Thr Ser Asp Asp Asn Tyr Gly Arg Ser Glu
                900                 905                 910

Ala Lys Arg Ser Ser Met Ile Glu Thr Gly Gln Gly Ala Glu Gly Gly
    915                 920                 925

Leu Ser Leu Arg Val Gln Asn Ser Leu Arg Arg Thr His Ser Glu
930                 935                 940

Gly Ser Leu Leu Gln Glu Pro Arg Gly Pro Cys Phe Ala Ser Asp Thr
945                 950                 955                 960

Thr Leu His Cys Ser Asp Gly Glu Gly Ala Ala Ser Thr Trp Gly Met
            965                 970                 975

Pro Ser Pro Ser Thr Leu Lys Lys Glu Leu Gly Arg Asn Gly Gly Ser
                980                 985                 990

Met His His Leu Ser Leu Phe Phe Thr Gly His Arg Lys Met Ser Gly
    995                 1000                1005

Ala Asp Thr Val Gly Asp Asp Glu Ala Ser Arg Lys Arg Lys
    1010                1015                1020

Ser Lys Asn Leu Ala Lys Asp Met Lys Asn Lys Leu Gly Ile Phe
    1025                1030                1035

Arg Arg Arg Asn Glu Ser Pro Gly Ala Pro Pro Ala Gly Lys Ala
    1040                1045                1050

Asp Lys Met Met Lys Ser Phe Lys Pro Thr Ser Glu Glu Ala Leu
    1055                1060                1065

Lys Trp Gly Glu Ser Leu Glu Lys Leu Leu Val His Lys Tyr Gly
    1070                1075                1080

Leu Ala Val Phe Gln Ala Phe Leu Arg Thr Glu Phe Ser Glu Glu
    1085                1090                1095

Asn Leu Glu Phe Trp Leu Ala Cys Glu Asp Phe Lys Lys Val Lys
    1100                1105                1110

Ser Gln Ser Lys Met Ala Ser Lys Ala Lys Lys Ile Phe Ala Glu
    1115                1120                1125

Tyr Ile Ala Ile Gln Ala Cys Lys Glu Val Asn Leu Asp Ser Tyr
    1130                1135                1140

Thr Arg Glu His Thr Lys Asp Asn Leu Gln Ser Val Thr Arg Gly
    1145                1150                1155

Cys Phe Asp Leu Ala Gln Lys Arg Ile Phe Gly Leu Met Glu Lys
    1160                1165                1170

Asp Ser Tyr Pro Arg Phe Leu Arg Ser Asp Leu Tyr Leu Asp Leu
    1175                1180                1185

Ile Asn Gln Lys Lys Met Ser Pro Pro Leu
    1190                1195

<210> SEQ ID NO 19
<211> LENGTH: 1833
<212> TYPE: DNA

<213> ORGANISM: Mus Musculus

<400> SEQUENCE: 19

```
atggagaggc cacatcagga tgcttccttg tccaaaaaag atgcctgcac ccagacttac      60
ccacctagga ggaggatcag gcatgcccaa gtgcaggatg caggtcaact gaagctgtcc     120
attgatgccc aggatcgggt tctgctgctg cacatcatag aaggcaaagg cctgatgagc     180
agggagcctg gcatctgcga tccctatgtg aaggtttctt tgatcccaga agacagccag     240
ctcccctgcc agaccacaca gatcattcca gactgccgag acccagcttt ccacgagcac     300
ttcttctttc ctgtcccaga ggagggtgat cagaagcgtc ttctggtgac agtgtggaac     360
cgggccagtg agaccaggca gcatacgctt attggctgca tgagctttgg ggtgaggtct     420
ctcttgactc cggacaagga gatcagtggc tggtactatc tgctagggga ggacctgggt     480
cggaccaagc acctcaaggt ggctaggcgg cggctccagc ccctgagaga catgctgttg     540
agaatgccag agaggggga ccctgagaac ggggagaaac tccagatcac catccggagg     600
ggcaaagacg gctttggctt caccatctgc tgtgactctc cggtccgagt ccaggctgtg     660
gattctgggg gcccggcaga gagggcggga ctgcagcagc tggacacagt gctacaactg     720
aatgagagac ccgtggagca ctggaaatgt gtggagctgg cacatgagat ccggagctgt     780
cctagcgaga tcatcctgct cgtgtggcgt gtggtccccc agatcaagcc ggggccagat     840
ggcggagtct tgcggcgggc ctcctgcaag tccacacatg acctcctgtc accccctaac     900
aagagggaga agaactgtac tcatggggcc ccagttcgtc ctgagcagcg ccacagctgc     960
cacctggtgt gtgacagctc tgatggtcta ctgcttggtg gctgggagcg ctacactgag    1020
gtgggcaagc gcagtggcca gcacaccctg cctgcactgt cccggaccac caccccctact   1080
gaccccaact acatcatcct ggccccactg aatcctggaa gccagttgct gcggcctgtg    1140
taccaggagg atacaatccc tgaagaaccg ggactacta ctaaagggaa atcgtacacc     1200
ggcctgggca gaagtctccg gctcatgaag acagtgcaga ccatgaaggg ccacagtaac    1260
taccaagact gctcagccct gagaccgcac atcccgcatt ccagttacgg cacctatgtc    1320
accctggccc ctaaagtcct ggtgttccct gtctttgtgc agccccctaga tctctgtaac    1380
cctgcccgga ctctcctgct gtcggaggag ctgctgctgt atgagggggag gaacaagact    1440
tcccaggtga cactgtttgc ctactcggac ctgctgctgt tcactaagga ggaggagcca    1500
ggccgctgcg acgtcctgag aaatccctc tacctccaga gcgtgaagct acaggagggc     1560
tcttcagaag acttgaaatt ctgtgtgctg tacctggcag agaaggcaga gtgcttattc    1620
actttggagg cacactcgca ggagcagaag aagagagtgt gctggtgcct gtcggagaac    1680
atcgccaagc agcaacagct ggccgcacca cctacagaga ggaagaaact tcacccttac    1740
ggctctctcc agcaggagat ggggccagtc acctccatca gtgccaccca ggatagaagc    1800
tttacctcat caggacagac cctgattggc tga                                 1833
```

<210> SEQ ID NO 20
<211> LENGTH: 610
<212> TYPE: PRT
<213> ORGANISM: Mus Musculus

<400> SEQUENCE: 20

```
Met Glu Arg Pro His Gln Asp Ala Ser Leu Ser Lys Lys Asp Ala Cys
 1               5                  10                  15

Thr Gln Thr Tyr Pro Pro Arg Arg Arg Ile Arg His Ala Gln Val Gln
            20                  25                  30
```

```
Asp Ala Gly Gln Leu Lys Leu Ser Ile Asp Ala Gln Asp Arg Val Leu
            35                  40                  45
Leu Leu His Ile Ile Glu Gly Lys Gly Leu Met Ser Arg Glu Pro Gly
 50                  55                  60
Ile Cys Asp Pro Tyr Val Lys Val Ser Leu Ile Pro Glu Asp Ser Gln
 65                  70                  75                  80
Leu Pro Cys Gln Thr Thr Gln Ile Ile Pro Asp Cys Arg Asp Pro Ala
                    85                  90                  95
Phe His Glu His Phe Phe Pro Val Pro Glu Glu Gly Asp Gln Lys
                100                 105                 110
Arg Leu Leu Val Thr Val Trp Asn Arg Ala Ser Glu Thr Arg Gln His
            115                 120                 125
Thr Leu Ile Gly Cys Met Ser Phe Gly Val Arg Ser Leu Leu Thr Pro
130                 135                 140
Asp Lys Glu Ile Ser Gly Trp Tyr Tyr Leu Leu Gly Glu Asp Leu Gly
145                 150                 155                 160
Arg Thr Lys His Leu Lys Val Ala Arg Arg Leu Gln Pro Leu Arg
                165                 170                 175
Asp Met Leu Leu Arg Met Pro Gly Glu Gly Asp Pro Gly Asn Gly Glu
            180                 185                 190
Lys Leu Gln Ile Thr Ile Arg Arg Gly Lys Asp Gly Phe Gly Phe Thr
            195                 200                 205
Ile Cys Cys Asp Ser Pro Val Arg Val Gln Ala Val Asp Ser Gly Gly
210                 215                 220
Pro Ala Glu Arg Ala Gly Leu Gln Gln Leu Asp Thr Val Leu Gln Leu
225                 230                 235                 240
Asn Glu Arg Pro Val Glu His Trp Lys Cys Val Glu Leu Ala His Glu
                245                 250                 255
Ile Arg Ser Cys Pro Ser Glu Ile Ile Leu Leu Val Trp Arg Val Val
            260                 265                 270
Pro Gln Ile Lys Pro Gly Pro Asp Gly Gly Val Leu Arg Arg Ala Ser
            275                 280                 285
Cys Lys Ser Thr His Asp Leu Leu Ser Pro Pro Asn Lys Arg Glu Lys
290                 295                 300
Asn Cys Thr His Gly Ala Pro Val Arg Pro Glu Gln Arg His Ser Cys
305                 310                 315                 320
His Leu Val Cys Asp Ser Ser Asp Gly Leu Leu Leu Gly Gly Trp Glu
                325                 330                 335
Arg Tyr Thr Glu Val Gly Lys Arg Ser Gly Gln His Thr Leu Pro Ala
            340                 345                 350
Leu Ser Arg Thr Thr Thr Pro Thr Asp Pro Asn Tyr Ile Ile Leu Ala
            355                 360                 365
Pro Leu Asn Pro Gly Ser Gln Leu Leu Arg Pro Val Tyr Gln Glu Asp
370                 375                 380
Thr Ile Pro Glu Glu Pro Gly Thr Thr Thr Lys Gly Lys Ser Tyr Thr
385                 390                 395                 400
Gly Leu Gly Lys Lys Ser Arg Leu Met Lys Thr Val Gln Thr Met Lys
                405                 410                 415
Gly His Ser Asn Tyr Gln Asp Cys Ser Ala Leu Arg Pro His Ile Pro
            420                 425                 430
His Ser Ser Tyr Gly Thr Tyr Val Thr Leu Ala Pro Lys Val Leu Val
            435                 440                 445
```

```
Phe Pro Val Phe Val Gln Pro Leu Asp Leu Cys Asn Pro Ala Arg Thr
450                 455                 460
Leu Leu Leu Ser Glu Glu Leu Leu Leu Tyr Glu Gly Arg Asn Lys Thr
465                 470                 475                 480
Ser Gln Val Thr Leu Phe Ala Tyr Ser Asp Leu Leu Leu Phe Thr Lys
                485                 490                 495
Glu Glu Glu Pro Gly Arg Cys Asp Val Leu Arg Asn Pro Leu Tyr Leu
            500                 505                 510
Gln Ser Val Lys Leu Gln Glu Gly Ser Ser Glu Asp Leu Lys Phe Cys
        515                 520                 525
Val Leu Tyr Leu Ala Glu Lys Ala Glu Cys Leu Phe Thr Leu Glu Ala
530                 535                 540
His Ser Gln Glu Gln Lys Lys Arg Val Cys Trp Cys Leu Ser Glu Asn
545                 550                 555                 560
Ile Ala Lys Gln Gln Gln Leu Ala Ala Pro Thr Glu Arg Lys Lys
                565                 570                 575
Leu His Pro Tyr Gly Ser Leu Gln Gln Glu Met Gly Pro Val Thr Ser
            580                 585                 590
Ile Ser Ala Thr Gln Asp Arg Ser Phe Thr Ser Ser Gly Gln Thr Leu
        595                 600                 605
Ile Gly
610
```

<210> SEQ ID NO 21
<211> LENGTH: 2901
<212> TYPE: DNA
<213> ORGANISM: Mus Musculus

<400> SEQUENCE: 21

```
atgaaccgct tcaatgggct ctgcaaagtg tgttcagaac gccgctaccg gcagatcacc      60
atccggaggg gcaaagacgg cttttggcttc accatctgct gtgactctcc ggtccgagtc     120
caggctgtgg attctggggg cccggcagag agggcgggac tgcagcagct ggacacagtg     180
ctacaactga atgagagacc cgtggagcac tggaaatgtg tggagctggc acatgagatc     240
cggagctgtc ctagcgagat catcctgctc gtgtggcgtg tggtccccca gatcaagccg     300
gggccagatg gcggagtctt gcggcgggcc tcctgcaagt ccacacatga cctcctgtca     360
ccccctaaca agagggagaa gaactgtact catgggccc cagttcgtcc tgagcagcgc      420
cacagctgcc acctggtgtg tgacagctct gatggtctac tgcttggtgg ctgggagcgc     480
tacactgagg tgggcaagcg cagtggccag cacaccctgc ctgcactgtc ccggaccacc     540
accctactg accccaacta catcatcctg gccccactga atcctggaag ccagttgctg     600
cggcctgtgt accaggagga tacaatccct gaagaaccgg ggactactac taaagggaaa     660
tcgtacaccg gctgggcaa gaagtctcgg ctcatgaaga cagtgcagac catgaagggc     720
cacagtaact accaagactg ctcagccctg agaccgcaca tcccgcattc cagttacggc     780
acctatgtca ccctggcccc taaagtcctg gtgttccctg tctttgtgca gcccctagat     840
ctctgtaacc ctgcccggac tctcctgctg tcggaggagc tgctgctgta tgaggggagg     900
aacaagactt cccaggtgac actgtttgcc tactcggacc tgctgctgtt cactaaggag     960
gaggagccag ccgctgcga cgtcctgaga aatcccctct acctccagag cgtgaagcta    1020
caggagggct cttcagaaga cttgaaattc tgtgtgctgt acctggcaga aaaggcagag    1080
tgcttattca ctttggaggc acactcgcag gagcagaaga agagagtgtg ctggtgcctg    1140
```

```
tcggagaaca tcgccaagca gcaacagctg gccgcaccac ctacagagag gaagatgttt    1200
gagacagagg cagatgagaa ggagatgccc ctggtcgagg ggaagggggcc aggtgctgag    1260 gaacccgcac ccagcaaaaa tccctctcct ggccaggagc ttcctccagg acaagacctc    1320
cctcccagca agaccccctc tcccagccag gagcttcctg caggacaaga tctccctccc    1380
agcaaagacc cctctcccag ccaggagctt cctgcaggac aagatctccc tcccagcaaa    1440 gaccctctc ccagccagga gcttcctgta ggacaagacc tcccacccag gaaggactcc     1500
tcaggccaag aagctgctcc tggcccagaa tcaccatcca gtgaagacat agcaacctgc    1560
cctaagcccc ctcaaagccc agaaacctca acaagcaagg actccccacc aggccaggga    1620
tcctccccga ccacagaact cccatcttgc cagggccttc ctgctggtca agaatctact    1680
agccaggacc ctctgctcag tcaagagccc ctgttatcc cagaatcctc tgcctccgtc     1740
cagaaacgcc taccctctca ggagtcaccc tccagcctgg gctccctgcc agagaaggac    1800
cttgctgagc agaccatcag ctccggggag ccaccagtcg ccactggtgc tgtactgcca    1860
gcctctagac ctaactttgt gatccccgag gtgcgtctgg ataatgccta cagccaactg    1920 gatgggccc acggaggcag ctctggcgag gacgaggatg cagaagaggg agaggagggg     1980
ggagaagggg aggaagatga ggaggacgac accagcgacg acaactacgg ggatcgtagt    2040
gaggccaagc gcagcagcct gattgagact ggccaaggcg ccgagggcgg cttctcgttg    2100
cgtgtgcaga actcgctgcg gcgccggacg cacagcgagg gcagcctgct gcaggagtcc    2160 cggggggccct gctttgcctc tgacaccacc ttacactgct ctgatggcga gggcgccaca    2220
tccacctggg ctatcccttc accccgcacc ctcaaaaaag aactgggtcg taatggaggc    2280
tccatgcacc acctttccct gttcttcacg ggacacagga agatgagtgg gactgacctc    2340
acagaatgtg atgaagcttc ccggaagaga aagagcaaaa acatagccaa ggacatgaag    2400
aataagctgg ccatcttcag gcggcggaac gaatctcccg gggctcagcc agccagcaag    2460
acagacaaga caaccaagtc cttcaagcct acctcggagg aagccctcaa gtggagcgag    2520
tccctggaaa agttgctgct tcataaatat ggcttagaag tgttccaggc cttccttcgc    2580
accgagttca gtgaggagaa cctggagttt tggctcgctt gcgaggactt caagaaggtc    2640
aaatcacagt ccaagatggc agccaaagcc aagaagatct ttgctgaatt catcgcaatc    2700
caggcttgca aagaggtaaa cctggactcc tacacacgag aacacaccaa ggagaatctg    2760
cagagcatca cccgaggctg ctttgacttg gcacagaaac gtatctttgg gctcatggag    2820
aaggactctt accctcgctt cctccgctct gacctctacc tggacctcat taaccagaag    2880
aagatgagtc ccccgctcta g                                                2901
```

<210> SEQ ID NO 22
<211> LENGTH: 966
<212> TYPE: PRT
<213> ORGANISM: Mus Musculus

<400> SEQUENCE: 22

```
Met Asn Arg Phe Asn Gly Leu Cys Lys Val Cys Ser Glu Arg Arg Tyr
1               5                   10                  15

Arg Gln Ile Thr Ile Arg Arg Gly Lys Asp Gly Phe Gly Phe Thr Ile
            20                  25                  30

Cys Cys Asp Ser Pro Val Arg Val Gln Ala Val Asp Ser Gly Gly Pro
        35                  40                  45

Ala Glu Arg Ala Gly Leu Gln Gln Leu Asp Thr Val Leu Gln Leu Asn
    50                  55                  60
```

-continued

```
Glu Arg Pro Val Glu His Trp Lys Cys Val Glu Leu Ala His Glu Ile
 65                  70                  75                  80

Arg Ser Cys Pro Ser Glu Ile Ile Leu Leu Val Trp Arg Val Val Pro
                 85                  90                  95

Gln Ile Lys Pro Gly Pro Asp Gly Gly Val Leu Arg Arg Ala Ser Cys
            100                 105                 110

Lys Ser Thr His Asp Leu Leu Ser Pro Pro Asn Lys Arg Glu Lys Asn
            115                 120                 125

Cys Thr His Gly Ala Pro Val Arg Pro Glu Gln Arg His Ser Cys His
        130                 135                 140

Leu Val Cys Asp Ser Ser Asp Gly Leu Leu Gly Gly Trp Glu Arg
145                 150                 155                 160

Tyr Thr Glu Val Gly Lys Arg Ser Gly Gln His Thr Leu Pro Ala Leu
                165                 170                 175

Ser Arg Thr Thr Thr Pro Thr Asp Pro Asn Tyr Ile Ile Leu Ala Pro
                180                 185                 190

Leu Asn Pro Gly Ser Gln Leu Leu Arg Pro Val Tyr Gln Glu Asp Thr
            195                 200                 205

Ile Pro Glu Glu Pro Gly Thr Thr Thr Lys Gly Lys Ser Tyr Thr Gly
210                 215                 220

Leu Gly Lys Lys Ser Arg Leu Met Lys Thr Val Gln Thr Met Lys Gly
225                 230                 235                 240

His Ser Asn Tyr Gln Asp Cys Ser Ala Leu Arg Pro His Ile Pro His
                245                 250                 255

Ser Ser Tyr Gly Thr Tyr Val Thr Leu Ala Pro Lys Val Leu Val Phe
            260                 265                 270

Pro Val Phe Val Gln Pro Leu Asp Leu Cys Asn Pro Ala Arg Thr Leu
            275                 280                 285

Leu Leu Ser Glu Glu Leu Leu Leu Tyr Glu Gly Arg Asn Lys Thr Ser
290                 295                 300

Gln Val Thr Leu Phe Ala Tyr Ser Asp Leu Leu Leu Phe Thr Lys Glu
305                 310                 315                 320

Glu Glu Pro Gly Arg Cys Asp Val Leu Arg Asn Pro Leu Tyr Leu Gln
                325                 330                 335

Ser Val Lys Leu Gln Glu Gly Ser Ser Glu Asp Leu Lys Phe Cys Val
            340                 345                 350

Leu Tyr Leu Ala Glu Lys Ala Glu Cys Leu Phe Thr Leu Glu Ala His
            355                 360                 365

Ser Gln Glu Gln Lys Lys Arg Val Cys Trp Cys Leu Ser Glu Asn Ile
            370                 375                 380

Ala Lys Gln Gln Gln Leu Ala Ala Pro Pro Thr Glu Arg Lys Met Phe
385                 390                 395                 400

Glu Thr Glu Ala Asp Glu Lys Glu Met Pro Leu Val Glu Gly Lys Gly
                405                 410                 415

Pro Gly Ala Glu Glu Pro Ala Pro Ser Lys Asn Pro Ser Pro Gly Gln
            420                 425                 430

Glu Leu Pro Pro Gly Gln Asp Leu Pro Pro Ser Lys Asp Pro Ser Pro
            435                 440                 445

Ser Gln Glu Leu Pro Ala Gly Gln Asp Leu Pro Pro Ser Lys Asp Pro
        450                 455                 460

Ser Pro Ser Gln Glu Leu Pro Ala Gly Gln Asp Leu Pro Pro Ser Lys
465                 470                 475                 480
```

-continued

```
Asp Pro Ser Pro Ser Gln Glu Leu Pro Val Gly Gln Asp Leu Pro Pro
                485                 490                 495
Arg Lys Asp Ser Ser Gly Gln Glu Ala Ala Pro Gly Pro Glu Ser Pro
            500                 505                 510
Ser Ser Glu Asp Ile Ala Thr Cys Pro Lys Pro Pro Gln Ser Pro Glu
        515                 520                 525
Thr Ser Thr Ser Lys Asp Ser Pro Pro Gly Gln Gly Ser Ser Pro Thr
    530                 535                 540
Thr Glu Leu Pro Ser Cys Gln Gly Leu Pro Ala Gly Gln Glu Ser Thr
545                 550                 555                 560
Ser Gln Asp Pro Leu Leu Ser Gln Glu Pro Pro Val Ile Pro Glu Ser
                565                 570                 575
Ser Ala Ser Val Gln Lys Arg Leu Pro Ser Gln Glu Ser Pro Ser Ser
            580                 585                 590
Leu Gly Ser Leu Pro Glu Lys Asp Leu Ala Glu Gln Thr Ile Ser Ser
        595                 600                 605
Gly Glu Pro Pro Val Ala Thr Gly Ala Val Leu Pro Ala Ser Arg Pro
    610                 615                 620
Asn Phe Val Ile Pro Glu Val Arg Leu Asp Asn Ala Tyr Ser Gln Leu
625                 630                 635                 640
Asp Gly Ala His Gly Gly Ser Ser Gly Glu Asp Glu Ala Glu Glu
                645                 650                 655
Gly Glu Glu Gly Gly Glu Gly Glu Asp Glu Glu Asp Asp Thr Ser
            660                 665                 670
Asp Asp Asn Tyr Gly Asp Arg Ser Glu Ala Lys Arg Ser Ser Leu Ile
        675                 680                 685
Glu Thr Gly Gln Gly Ala Glu Gly Gly Phe Ser Leu Arg Val Gln Asn
    690                 695                 700
Ser Leu Arg Arg Arg Thr His Ser Glu Gly Ser Leu Leu Gln Glu Ser
705                 710                 715                 720
Arg Gly Pro Cys Phe Ala Ser Asp Thr Thr Leu His Cys Ser Asp Gly
                725                 730                 735
Glu Gly Ala Thr Ser Thr Trp Ala Ile Pro Ser Pro Arg Thr Leu Lys
            740                 745                 750
Lys Glu Leu Gly Arg Asn Gly Gly Ser Met His His Leu Ser Leu Phe
        755                 760                 765
Phe Thr Gly His Arg Lys Met Ser Gly Thr Asp Leu Thr Glu Cys Asp
    770                 775                 780
Glu Ala Ser Arg Lys Arg Lys Ser Lys Asn Ile Ala Lys Asp Met Lys
785                 790                 795                 800
Asn Lys Leu Ala Ile Phe Arg Arg Asn Glu Ser Pro Gly Ala Gln
                805                 810                 815
Pro Ala Ser Lys Thr Asp Lys Thr Thr Lys Ser Phe Lys Pro Thr Ser
            820                 825                 830
Glu Glu Ala Leu Lys Trp Ser Glu Ser Leu Glu Lys Leu Leu Leu His
        835                 840                 845
Lys Tyr Gly Leu Glu Val Phe Gln Ala Phe Leu Arg Thr Glu Phe Ser
    850                 855                 860
Glu Glu Asn Leu Glu Phe Trp Leu Ala Cys Glu Asp Phe Lys Lys Val
865                 870                 875                 880
Lys Ser Gln Ser Lys Met Ala Ala Lys Ala Lys Lys Ile Phe Ala Glu
                885                 890                 895
Phe Ile Ala Ile Gln Ala Cys Lys Glu Val Asn Leu Asp Ser Tyr Thr
```

```
                        900                 905                 910
Arg Glu His Thr Lys Glu Asn Leu Gln Ser Ile Thr Arg Gly Cys Phe
            915                 920                 925

Asp Leu Ala Gln Lys Arg Ile Phe Gly Leu Met Glu Lys Asp Ser Tyr
        930                 935                 940

Pro Arg Phe Leu Arg Ser Asp Leu Tyr Leu Asp Leu Ile Asn Gln Lys
945                 950                 955                 960

Lys Met Ser Pro Pro Leu
                965

<210> SEQ ID NO 23
<211> LENGTH: 1302
<212> TYPE: DNA
<213> ORGANISM: Mus Musculus

<400> SEQUENCE: 23
```

| | | | | | |
|---|---|---|---|---|---|
| atgaaccgct | tcaatgggct | ctgcaaagtg | tgttcagaac | gccgctaccg | gcagatcacc | 60 |
| atccggaggg | gcaaagacgg | ctttggcttc | accatctgct | gtgactctcc | ggtccgagtc | 120 |
| caggctgtgg | attctggggg | cccggcagag | agggcgggac | tgcagcagct | ggacacagtg | 180 |
| ctacaactga | atgagagacc | cgtggagcac | tggaaatgtg | tggagctggc | acatgagatc | 240 |
| cggagctgtc | ctagcgagat | catcctgctc | gtgtggcgtg | tggtccccca | gatcaagccg | 300 |
| gggccagatg | gcggagtctt | gcggcgggcc | tcctgcaagt | ccacacatga | cctcctgtca | 360 |
| cccctaaca | agagggagaa | gaactgtact | catggggccc | cagttcgtcc | tgagcagcgc | 420 |
| cacagctgcc | acctggtgtg | tgacagctct | gatggtctac | tgcttggtgg | ctgggagcgc | 480 |
| tacactgagg | tgggcaagcg | cagtggccag | cacaccctgc | ctgcactgtc | ccggaccacc | 540 |
| accctactg | accccaacta | catcatcctg | ccccactga | atcctggaag | ccagttgctg | 600 |
| cggcctgtgt | accaggagga | tacaatccct | gaagaaccgg | ggactactac | taaagggaaa | 660 |
| tcgtacaccg | gcctgggcaa | gaagtctcgg | ctcatgaaga | cagtgcagac | catgaagggc | 720 |
| cacagtaact | accaagactg | ctcagccctg | agaccgcaca | tcccgcattc | cagttacggc | 780 |
| acctatgtca | ccctggcccc | taaagtcctg | gtgttccctg | tctttgtgca | gcccctagat | 840 |
| ctctgtaacc | ctgcccggac | tctcctgctg | tcggaggagc | tgctgctgta | tgaggggagg | 900 |
| aacaagactt | cccaggtgac | actgtttgcc | tactcggacc | tgctgctgtt | cactaaggag | 960 |
| gaggagccag | gccgctgcga | cgtcctgaga | aatcccctct | acctccagag | cgtgaagcta | 1020 |
| caggagggct | cttcagaaga | cttgaaattc | tgtgtgctgt | acctggcaga | gaaggcagag | 1080 |
| tgcttattca | ctttggaggc | acactcgcag | gagcagaaga | agagagtgtg | ctggtgcctg | 1140 |
| tcggagaaca | tcgccaagca | gcaacagctg | gccgcaccac | ctacagagag | gaagaaactt | 1200 |
| caccccttacg | gctctctcca | gcaggagatg | gggccagtca | cctccatcag | tgccacccag | 1260 |
| gatagaagct | ttacctcatc | aggacagacc | ctgattggct | ga | | 1302 |

```
<210> SEQ ID NO 24
<211> LENGTH: 433
<212> TYPE: PRT
<213> ORGANISM: Mus Musculus

<400> SEQUENCE: 24

Met Asn Arg Phe Asn Gly Leu Cys Lys Val Cys Ser Glu Arg Arg Tyr
1               5                   10                  15

Arg Gln Ile Thr Ile Arg Arg Gly Lys Asp Gly Phe Gly Phe Thr Ile
            20                  25                  30
```

```
Cys Cys Asp Ser Pro Val Arg Val Gln Ala Val Asp Ser Gly Gly Pro
        35                  40                  45

Ala Glu Arg Ala Gly Leu Gln Gln Leu Asp Thr Val Leu Gln Leu Asn
    50                  55                  60

Glu Arg Pro Val Glu His Trp Lys Cys Val Glu Leu Ala His Glu Ile
65                  70                  75                  80

Arg Ser Cys Pro Ser Glu Ile Ile Leu Leu Val Trp Arg Val Val Pro
                85                  90                  95

Gln Ile Lys Pro Gly Pro Asp Gly Gly Val Leu Arg Arg Ala Ser Cys
                100                 105                 110

Lys Ser Thr His Asp Leu Leu Ser Pro Pro Asn Lys Arg Glu Lys Asn
            115                 120                 125

Cys Thr His Gly Ala Pro Val Arg Pro Glu Gln Arg His Ser Cys His
        130                 135                 140

Leu Val Cys Asp Ser Ser Asp Gly Leu Leu Leu Gly Gly Trp Glu Arg
145                 150                 155                 160

Tyr Thr Glu Val Gly Lys Arg Ser Gly Gln His Thr Leu Pro Ala Leu
                165                 170                 175

Ser Arg Thr Thr Thr Pro Thr Asp Pro Asn Tyr Ile Ile Leu Ala Pro
                180                 185                 190

Leu Asn Pro Gly Ser Gln Leu Leu Arg Pro Val Tyr Gln Glu Asp Thr
            195                 200                 205

Ile Pro Glu Glu Pro Gly Thr Thr Lys Gly Lys Ser Tyr Thr Gly
        210                 215                 220

Leu Gly Lys Lys Ser Arg Leu Met Lys Thr Val Gln Thr Met Lys Gly
225                 230                 235                 240

His Ser Asn Tyr Gln Asp Cys Ser Ala Leu Arg Pro His Ile Pro His
                245                 250                 255

Ser Ser Tyr Gly Thr Tyr Val Thr Leu Ala Pro Lys Val Leu Val Phe
            260                 265                 270

Pro Val Phe Val Gln Pro Leu Asp Leu Cys Asn Pro Ala Arg Thr Leu
        275                 280                 285

Leu Leu Ser Glu Glu Leu Leu Leu Tyr Glu Gly Arg Asn Lys Thr Ser
        290                 295                 300

Gln Val Thr Leu Phe Ala Tyr Ser Asp Leu Leu Leu Phe Thr Lys Glu
305                 310                 315                 320

Glu Glu Pro Gly Arg Cys Asp Val Leu Arg Asn Pro Leu Tyr Leu Gln
                325                 330                 335

Ser Val Lys Leu Gln Glu Gly Ser Ser Glu Asp Leu Lys Phe Cys Val
            340                 345                 350

Leu Tyr Leu Ala Glu Lys Ala Glu Cys Leu Phe Thr Leu Glu Ala His
            355                 360                 365

Ser Gln Glu Gln Lys Lys Arg Val Cys Trp Cys Leu Ser Glu Asn Ile
    370                 375                 380

Ala Lys Gln Gln Gln Leu Ala Ala Pro Pro Thr Glu Arg Lys Lys Leu
385                 390                 395                 400

His Pro Tyr Gly Ser Leu Gln Gln Glu Met Gly Pro Val Thr Ser Ile
                405                 410                 415

Ser Ala Thr Gln Asp Arg Ser Phe Thr Ser Ser Gly Gln Thr Leu Ile
            420                 425                 430

Gly
```

<210> SEQ ID NO 25
<211> LENGTH: 1809
<212> TYPE: DNA
<213> ORGANISM: Canis familiaris

<400> SEQUENCE: 25

| | | | | | |
|---|---|---|---|---|---|
| atgcagcgct | ccctgcaccg | cgtggccctc | gggagccggc | gcgcccgccc | cggcctgtcc | 60 |
| ttctacctcg | ccaccttcgg | tcagctgaag | ctgtcgatcg | atgcccggga | ccgggttctg | 120 |
| ctgctccaca | tcatagaagg | caaaggcctg | atgagcagag | agcctggcat | ctgtgatccc | 180 |
| tacgtgaaga | tttctttgat | cccagaagat | aatcgactac | gtcgccagaa | gacgcagacg | 240 |
| gtcccagact | gcagagagcc | agtcttccac | gagcacttct | tttttcctgt | ccaagaggaa | 300 |
| gatgaacaga | agcgccttct | ggtcactgtg | tggaataggg | caggtgactc | caggcagagt | 360 |
| ggactcattg | gctgcatgag | ctttggggtg | aagtccctcc | tgactccgga | caaggaaatc | 420 |
| agtggctggt | actaccttct | ggggaagac | ctgggccgga | ctaaacacct | gaaggtggcc | 480 |
| aggcggcggc | tgcggcccct | gagagacccg | ctgctgagaa | caccaggatg | tggggatgct | 540 |
| gagaacgggg | agaaactcaa | gatcaccatc | ccgaggggga | aggacggctt | tggcttcacc | 600 |
| atctgctgtg | actctccggt | tcgagtccag | gcagtggatt | ctggaggtcc | agcggagcgg | 660 |
| gcagggctgc | agcagctgga | caccgtgctg | cagctgaacg | agaggcccgt | ggagcactgg | 720 |
| aaatgcgtgg | agctggccca | tgagatccgg | agctgcccca | gtgagatcat | cctgcttgtg | 780 |
| tggcgcatgg | tcccccaggt | caagccaggg | ccggacggcg | gggtcctgcg | gcgggcctcc | 840 |
| tgcaagtcga | cacatgacct | ccagtcaccc | cccaataagc | gggagaagaa | ttgcacccac | 900 |
| ggggcccagg | cacggcccga | gcagcgccac | agctgccacc | tggtgtgtga | cagctcagat | 960 |
| gggctgctgc | tcggcggctg | ggaacgctac | accgaggtgg | ccaagcgtgg | gggccagcat | 1020 |
| accctgcctg | cgctgtcccg | ggccacggcc | tccacggacc | ccaactacat | catcttggcc | 1080 |
| ccattgaacc | ccgggagcca | gctgctgcga | cctgtgtacc | aagaggatgc | catccccgaa | 1140 |
| gaatcaggta | gtcccagtaa | agggaagtcc | tacacgggcc | tggggaagaa | gtcccggctg | 1200 |
| atgaaaacag | tgcagaccat | gaagggccac | gggaactacc | agaactgccc | ggtcatgagg | 1260 |
| ccgcatgccc | cacactcaag | ctatggcacc | tacgtcaccc | tggcccccaa | agtcctcgtg | 1320 |
| tttccagtct | tgttcagcc | tttagatctc | tgtaaccctg | cccggacact | cctgttgtct | 1380 |
| gaggagctgc | tgctgtacga | ggggaggaac | aaggctgtgg | aggtgacgct | gtttgcctac | 1440 |
| tcggacctgc | tgctcttcac | caaggaagat | gagccgggac | gctgcaacgt | cctgaggaac | 1500 |
| cccctctacc | tccagagcgt | gaagctgcag | gaaggttctt | cagaagacct | gaaattctgt | 1560 |
| gtgctgtacc | tagcagagaa | ggcagagtgc | ttattcactt | tggaagcgca | ctcgcaggag | 1620 |
| cagaagaaga | gagtgtgctg | gtgcctgtcg | gagaacatcg | ccaagcagca | acagctggcc | 1680 |
| gcttcgcccc | tggagagcaa | gaaactccac | ccttatggct | ctctccagca | ggagatgggg | 1740 |
| ccggccaact | caaccaatgc | tacccaggat | agaagcttta | cctcatcagg | acagactctg | 1800 |
| attggctga | | | | | | 1809 |

<210> SEQ ID NO 26
<211> LENGTH: 602
<212> TYPE: PRT
<213> ORGANISM: Canis familiaris

<400> SEQUENCE: 26

Met Gln Arg Ser Leu His Arg Val Ala Leu Gly Ser Arg Arg Ala Arg
1               5                   10                  15

```
Pro Gly Leu Ser Phe Tyr Leu Ala Thr Phe Gly Gln Leu Lys Leu Ser
            20                  25                  30

Ile Asp Ala Arg Asp Arg Val Leu Leu His Ile Ile Glu Gly Lys
        35                  40                  45

Gly Leu Met Ser Arg Glu Pro Gly Ile Cys Asp Pro Tyr Val Lys Ile
    50                  55                  60

Ser Leu Ile Pro Glu Asp Asn Arg Leu Arg Gln Lys Thr Gln Thr
65                  70                  75                  80

Val Pro Asp Cys Arg Glu Pro Val Phe His Glu His Phe Phe Pro
                85                  90                  95

Val Gln Glu Glu Asp Glu Gln Lys Arg Leu Leu Val Thr Val Trp Asn
            100                 105                 110

Arg Ala Gly Asp Ser Arg Gln Ser Gly Leu Ile Gly Cys Met Ser Phe
            115                 120                 125

Gly Val Lys Ser Leu Leu Thr Pro Asp Lys Glu Ile Ser Gly Trp Tyr
    130                 135                 140

Tyr Leu Leu Gly Glu Asp Leu Gly Arg Thr Lys His Leu Lys Val Ala
145                 150                 155                 160

Arg Arg Arg Leu Arg Pro Leu Arg Asp Pro Leu Leu Arg Thr Pro Gly
                165                 170                 175

Cys Gly Asp Ala Glu Asn Gly Glu Lys Leu Lys Ile Thr Ile Pro Arg
            180                 185                 190

Gly Lys Asp Gly Phe Gly Phe Thr Ile Cys Cys Asp Ser Pro Val Arg
            195                 200                 205

Val Gln Ala Val Asp Ser Gly Gly Pro Ala Glu Arg Ala Gly Leu Gln
            210                 215                 220

Gln Leu Asp Thr Val Leu Gln Leu Asn Glu Arg Pro Val Glu His Trp
225                 230                 235                 240

Lys Cys Val Glu Leu Ala His Glu Ile Arg Ser Cys Pro Ser Glu Ile
                245                 250                 255

Ile Leu Leu Val Trp Arg Met Val Pro Gln Val Lys Pro Gly Pro Asp
            260                 265                 270

Gly Gly Val Leu Arg Arg Ala Ser Cys Lys Ser Thr His Asp Leu Gln
        275                 280                 285

Ser Pro Pro Asn Lys Arg Glu Lys Asn Cys Thr His Gly Ala Gln Ala
290                 295                 300

Arg Pro Glu Gln Arg His Ser Cys His Leu Val Cys Asp Ser Ser Asp
305                 310                 315                 320

Gly Leu Leu Leu Gly Gly Trp Glu Arg Tyr Thr Glu Val Ala Lys Arg
                325                 330                 335

Gly Gly Gln His Thr Leu Pro Ala Leu Ser Arg Ala Thr Ala Ser Thr
            340                 345                 350

Asp Pro Asn Tyr Ile Ile Leu Ala Pro Leu Asn Pro Gly Ser Gln Leu
            355                 360                 365

Leu Arg Pro Val Tyr Gln Glu Asp Ala Ile Pro Glu Glu Ser Gly Ser
        370                 375                 380

Pro Ser Lys Gly Lys Ser Tyr Thr Gly Leu Gly Lys Lys Ser Arg Leu
385                 390                 395                 400

Met Lys Thr Val Gln Thr Met Lys Gly His Gly Asn Tyr Gln Asn Cys
            405                 410                 415

Pro Val Met Arg Pro His Ala Pro His Ser Ser Tyr Gly Thr Tyr Val
            420                 425                 430
```

```
Thr Leu Ala Pro Lys Val Leu Val Phe Pro Val Phe Val Gln Pro Leu
            435                 440                 445

Asp Leu Cys Asn Pro Ala Arg Thr Leu Leu Ser Glu Glu Leu Leu
    450                 455                 460

Leu Tyr Glu Gly Arg Asn Lys Ala Val Glu Val Thr Leu Phe Ala Tyr
465                 470                 475                 480

Ser Asp Leu Leu Phe Thr Lys Glu Asp Glu Pro Gly Arg Cys Asn
                485                 490                 495

Val Leu Arg Asn Pro Leu Tyr Leu Gln Ser Val Lys Leu Gln Glu Gly
            500                 505                 510

Ser Ser Glu Asp Leu Lys Phe Cys Val Leu Tyr Leu Ala Glu Lys Ala
            515                 520                 525

Glu Cys Leu Phe Thr Leu Glu Ala His Ser Gln Glu Gln Lys Lys Arg
            530                 535                 540

Val Cys Trp Cys Leu Ser Glu Asn Ile Ala Lys Gln Gln Gln Leu Ala
545                 550                 555                 560

Ala Ser Pro Leu Glu Ser Lys Lys Leu His Pro Tyr Gly Ser Leu Gln
                565                 570                 575

Gln Glu Met Gly Pro Ala Asn Ser Thr Asn Ala Thr Gln Asp Arg Ser
            580                 585                 590

Phe Thr Ser Ser Gly Gln Thr Leu Ile Gly
                595                 600

<210> SEQ ID NO 27
<211> LENGTH: 12
<212> TYPE: PRT
<213> ORGANISM: Artificial Sequence
<220> FEATURE:
<223> OTHER INFORMATION: synthetic sequence

<400> SEQUENCE: 27

Gly Cys Ile Lys Ser Lys Arg Lys Asp Lys Asp Pro
1               5                   10

<210> SEQ ID NO 28
<211> LENGTH: 8
<212> TYPE: PRT
<213> ORGANISM: Artificial Sequence
<220> FEATURE:
<223> OTHER INFORMATION: synthetic sequence

<400> SEQUENCE: 28

Leu Arg Arg Ala Thr Leu Val Asp
1               5

<210> SEQ ID NO 29
<211> LENGTH: 32
<212> TYPE: PRT
<213> ORGANISM: Artificial Sequence
<220> FEATURE:
<223> OTHER INFORMATION: synthetic sequence

<400> SEQUENCE: 29

Pro Gln Gln Ala Arg Gln Lys Leu Gln Asn Leu Phe Ile Asn Phe Cys
1               5                   10                  15

Leu Ile Leu Ile Cys Leu Leu Leu Ile Cys Ile Ile Val Met Leu Leu
                20                  25                  30
```

METHODS FOR IMPROVING HEART FUNCTION

CROSS-REFERENCE TO RELATED APPLICATIONS

This application is a divisional of U.S. patent application Ser. No. 13/884,144 filed Jul. 29, 2013 and entitled "METHODS FOR IMPROVING HEART FUNCTION," now allowed, which is the national phase under 35 U.S.C. § 371 of International Patent Application No. PCT/US2011/059787, filed Nov. 8, 2011, which claims the benefit of U.S. Provisional Application No. 61/411,218, filed Nov. 8, 2010, all of which are herein incorporated by reference in their entirety. The PCT application was published as International Publication No. WO 2012/064743 on May 18, 2012.

STATEMENT OF RIGHTS

"This invention was made with government support under Grants PO1-HL077180, RO1-HL-089297, T32-HL0072, RO1-DK073368, DP1 OD006419, F31-GM087079, RO1-GM085058, RO1-HL-053432AI93256, AI67854, and AI24755 awarded by the National Institutes of Health. The U.S. government has certain rights in the invention." This statement is included solely to comply with 37 C.F.R. § 401.14(a)(f)(4) and should not be taken as an assertion or admission that the application discloses and/or claims only one invention.

SEQUENCE LISTING

The instant application contains a Sequence Listing, which has been submitted electronically in ASCII format and is hereby incorporated by reference in its entirety. Said ASCII copy, created on Mar. 1, 2017, is named 2017-03-01-01840035-DIV-ST25 and is 89,000 bytes in size.

BACKGROUND OF THE INVENTION

Despite major developments in both diagnosis and treatment, cardiac-related disorders, such as heart failure (HF), continue to be a leading cause of death and disability in older adults worldwide and affect more than 12 million patients in the United States and Europe alone (Lloyd-Jones et al. (2010) *Circulation* 121:948-954). Until recently, HF therapy usually consisted of pharmacological approaches to counter maladaptive neurohormonal stimulation and restore favorable hemodynamics. Over the past decade, however, the major advance has come from a device therapy termed cardiac resynchronization therapy (CRT) that uses electrical pacing of both right and left ventricles to restore contraction timing. It is designed to counter the dyssynchronous contraction within the left ventricle stemming from electrical conduction delay that is found in nearly a third of patients with HF. Electromechanical dyssynchrony confers independent risks for worsened morbidity and mortality, and CRT improves both in affected patients (Cleland et al. (2005) *N. Engl. J. Med.* 352:1539-1549; Cleland et al. (2006) *Eur. Heart J.* 27:1928-1932; Bristow et al. (2004) *N. Engl. J. Med.* 350:2140-2150; and Abraham et al. (2002) *N. Engl. J. Med.* 346:1845-1853). CRT is unique among HF treatments because it both acutely (Kasser et al. (1999) *Circulation* 99:1567-1573) and chronically (St. John Sutton et al. (2009) *Circulation* 120:1858-1865) enhances systolic function of the heart, yet confers long-term survival benefits (Cleland et al. (2005) *N. Engl. J. Med.* 352:1539-1549 and Cleland et al. (2006) *Eur. Heart J.* 27:1928-1932). None of the commonly used drugs designed to stimulate ventricular pump function has yet achieved this. To date, however, knowledge of the molecular and cellular effects of CRT remains limited. Accordingly, there exists a need in the art to identify specific molecular modifications from CRT that can be used to target and treat HF more broadly, for example, in patients without dyssynchrony.

SUMMARY OF THE INVENTION

The present invention is based, at least in part, on the discovery that transient exposure to dyssynchrony followed by restored cardiac synchronization/resynchronization or upregulation of myocardial RGS2 and/or RGS3 can significantly improve cardiac-related disorders, such as HF.

In one aspect, a device for treating heart failure may include a power source, an atrial stimulation electrode, a ventricular stimulation electrode, and a controller. The controller may be operably connected to the power source and to the stimulation electrode. The controller may be configured to receive a signal indicative of atrial electrical activity. The controller may be programmed to monitor the signal to detect an atrial heart rate. The controller may be programmed to operate the device in a normal pacing mode, for which the controller is programmed to cause the atrial stimulation electrode to depolarize atrial tissue if the atrial heart rate is below a predetermined limit. The controller may be programmed to periodically transiently operate the device in a dyssynchrony-inducing mode, for which the controller is programmed to cause the ventricular stimulation electrode to depolarize ventricular tissue at a single site with a delay relative to atrial electrical activity shorter than a normal atrioventricular conduction delay.

In another aspect, a method of treating heart failure may include inducing dyssynchronous contraction of a left ventricle in a subject suffering from heart failure, the subject not previously having had dyssynchronous contraction of the left ventricle; maintaining the dyssynchronous contraction for a period of time; and restoring synchronous contraction of the subject's left ventricle.

In one aspect, a method of assessing the efficacy of a test agent for inhibiting a cardiac-related disorder in a subject is provided, wherein the method comprises comparing: a) the amount and/or activity of a marker in a first sample obtained from the subject and maintained in the presence of the test agent, wherein the marker is RGS2 and/or RGS3; and b) the amount and/or activity of the marker in a control or second sample obtained from the subject and maintained in the absence of the test agent, wherein a significantly lower amount and/or activity of the marker in the first sample relative to the second sample is an indication that the test agent is efficacious for inhibiting the cardiac-related disorder. In one embodiment, the subject is selected from the group consisting of an animal model of the cardiac-related disorder or a human. In another embodiment, the first and/or at least one subsequent sample is selected from the group consisting of in vitro, ex vivo and in vivo samples. In still another embodiment, the first and second samples are portions of a single sample or pooled samples obtained from the subject. In yet another embodiment, the subject sample is obtained from heart muscle. In another embodiment, the amount of the marker is determined by determining the level of expression of the marker or by determining copy number of the marker. In still another embodiment, the level of expression of the marker in the sample is assessed by detecting the presence in the sample of a protein corresponding to the marker. In yet another embodiment, the presence of the protein is detected using a reagent which specifically binds with the protein (e.g., an antibody, an antibody derivative, and an antibody fragment). In another embodiment, the level of expression of the marker in the sample is assessed by detecting the presence in the sample of a transcribed polynucleotide (e.g., an mRNA or a cDNA) or portion thereof, wherein the transcribed polynucleotide comprises the marker. In still another embodiment, the step of detecting further comprises amplifying the transcribed polynucleotide. In yet another embodiment, the activity of the marker is determined by assessing one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In another embodiment, the cardiac-related disorder is heart failure.

In another aspect, a method of assessing the efficacy of a therapy for inhibiting a cardiac-related disorder in a subject is provided, wherein the method comprises comparing: a) the amount and/or activity of a marker in a first sample obtained from the subject and maintained in the presence of the test agent, wherein the marker is RGS2 and/or RGS3; and b) the amount and/or activity of the marker in a second sample obtained from the subject following provision of the portion of the therapy, wherein a significantly lower amount and/or activity of the marker in the first sample relative to the second sample is an indication that the test agent is efficacious for inhibiting the cardiac-related disorder. In one embodiment, the subject sample is obtained from heart muscle. In another embodiment, the amount of the marker is determined by determining the level of expression of the marker or by determining copy number of the marker. In still another embodiment, the level of expression of the marker in the sample is assessed by detecting the presence in the sample of a protein corresponding to the marker. In yet another embodiment, the presence of the protein is detected using a reagent which specifically binds with the protein (e.g., an antibody, an antibody derivative, and an antibody fragment). In another embodiment, the level of expression of the marker in the sample is assessed by detecting the presence in the sample of a transcribed polynucleotide (e.g., an mRNA or a cDNA) or portion thereof, wherein the transcribed polynucleotide comprises the marker. In still another embodiment, the step of detecting further comprises amplifying the transcribed polynucleotide. In yet another embodiment, the activity of the marker is determined by assessing one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In another embodiment, the cardiac-related disorder is heart failure.

In still another aspect, a method of treating a subject afflicted with a cardiac-related disorder is provided comprising administering to the subject an agent that modulates the amount and/or activity of a gene or protein corresponding to RGS2 and/or RGS3, thereby treating the subject afflicted with the cardiac-related disorder. In one embodiment, said agent is administered in a pharmaceutically acceptable formulation. In another embodiment, said agent is a nucleic acid encoding RGS2 and/or RGS3. In still another embodiment, said agent is a nucleic acid vector comprising a nucleic acid encoding RGS2 and/or RGS3 operably linked to a promoter. In yet another embodiment, the promoter is a cardiac muscle-specific promoter. In another embodiment, said agent is a peptide or peptidomimetic. In still another embodiment, said agent is a small molecule which promotes the amount and/or activity of said marker. In yet another embodiment, the method further comprises administering one or more agents that inhibit the cardiac-related disorder. In another embodiment, the activity of the marker is determined by assessing one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In still another embodiment, the cardiac-related disorder is heart failure.

In yet another aspect, a method of assessing whether a subject is afflicted with a cardiac-related disorder or at risk for developing a cardiac-related disorder is provided, wherein the method comprises comparing: a) the amount, structure, and/or activity of a marker in a subject sample, wherein the marker is RGS2 and/or RGS3; and b) the normal amount, structure, and/or activity of the marker, wherein a significant difference between the amount, structure, and/or activity of the marker in the sample and the normal amount, structure, and/or activity is an indication that the subject is afflicted with the cardiac-related disorder or at risk for developing the cardiac-related disorder. In one embodiment, the normal amount/structure, and/or activity is obtained from a control sample. In another embodiment, the subject is selected from the group consisting of an animal model of the cardiac-related disorder or a human. In still another embodiment, the subject sample is selected from the group consisting of in vitro, ex vivo and in vivo samples. In yet another embodiment, the subject sample is a single sample or pooled samples obtained from the subject. In another embodiment, the subject ample is obtained from heart muscle. In still another embodiment, the amount of the marker is determined by determining the level of expression of the marker or by determining copy number of the marker. In yet another embodiment, the level of expression of the marker in the sample is assessed by detecting the presence in the sample of a protein corresponding to the marker. In another embodiment, the presence of the protein is detected using a reagent which specifically binds with the protein (e.g., an antibody, an antibody derivative, and an antibody fragment). In still another embodiment, the level of expression of the marker in the sample is assessed by detecting the presence in the sample of a transcribed polynucleotide (e.g., an mRNA or a cDNA) or portion thereof, wherein the transcribed polynucleotide comprises the marker. In yet another embodiment, the step of detecting further comprises amplifying the transcribed polynucleotide. In another embodiment, the activity of the marker is determined by assessing one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In still another embodiment, the cardiac-related disorder is heart failure.

In another aspect, a method for monitoring the progression of a cardiac-related disorder in a subject is provided, wherein the method comprises: a) detecting in a subject sample at a first point in time, the amount and/or activity of a marker, wherein the marker is RGS2 or RG3; b) repeating step a) at a subsequent point in time; and c) comparing the amount and/or activity detected in steps a) and b), and therefrom monitoring the progression of the cardiac-related disorder in the subject. In one embodiment, the normal amount/structure, and/or activity is obtained from a control sample. In another embodiment, the subject is selected from the group consisting of an animal model of the cardiac-related disorder or a human. In still another embodiment, the subject sample is selected from the group consisting of in vitro, ex vivo and in vivo samples. In yet another embodiment, the subject sample is a single sample or pooled samples obtained from the subject. In another embodiment, the subject sample is obtained from heart muscle. In still another embodiment, the subject has undergone at least one treatment for the cardiac-related disorder or has completed treatment for the cardiac-related disorder between the first point in time and the subsequent point in time. In yet another embodiment, the amount of the marker is determined by determining the level of expression of the marker or by determining copy number of the marker. In another embodiment, the level of expression of the marker in the sample is assessed by detecting the presence in the sample of a protein corresponding to the marker. In still another embodiment, the presence of the protein is detected using a reagent which specifically binds with the protein (e.g., an antibody, an antibody derivative, and an antibody fragment). In yet another embodiment, the level of expression of the marker in the sample is assessed by detecting the presence in the sample of a transcribed polynucleotide (e.g., an mRNA or a cDNA) or portion thereof, wherein the transcribed polynucleotide comprises the marker. In another embodiment, the step of detecting further comprises amplifying the transcribed polynucleotide. In still another embodiment, the activity of the marker is determined by assessing one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In yet another embodiment, the cardiac-related disorder is heart failure.

In still another aspect, the use of an agent that modulates RGS2 and/or RGS3 expression and/or activity in a subject for the preparation of a medicament for inhibiting a cardiac-related disorder is provided. In one embodiment RGS2 and/or RGS3 expression and/or activity is upregulated (e.g., using an agent selected from the group consisting of a nucleic acid molecule encoding an RGS2 and/or RGS3 polypeptide or fragment thereof; an RGS2 and/or RGS3 polypeptide or fragment thereof; and a small molecule that binds to RGS2 and/or RGS3). In still another embodiment, the use further comprises the use of one or more agents that inhibit the cardiac-related disorder. In yet another embodiment, the inhibition of the cardiac-related disorder is determined by assessing one or more of (a) increased heart chamber mechanical efficiency; b) increased β-adrenergic receptor numbers and/or density; c) inhibited $G\alpha_i$ signaling; d) increased $G\alpha_s$-biased B2-adrenergic signaling; c) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In another embodiment, the cardiac-related disorder is heart failure.

BRIEF DESCRIPTION OF FIGURES

FIGS. 1A-1C show the impact of synchronous, dyssynchronous, and resynchronized HF on regional left ventricular wall motion, and myocyte β-adrenergic responsiveness. FIG. 1A shows regional longitudinal strain (derived from speckle tracking) for septal/anterior wall (solid line) and lateral wall (dotted line) of left ventricles in control and HF models. Normal controls have similar, simultaneous strains in both regions. In $HF_{dys}$, septal shortening precedes the lateral wall, with reciprocal septal stretch when the latter wall contracts. Restoration of synchrony is observed in the CRT model. Synchronous HF ($HF_{syn}$) displays concurrent strain in both regions. For V3A3, dyssynchrony is observed during the initial 3-week RV pacing period (RVP) and this is reverted to synchronous in the latter atrial pacing period (AP:V3A3). FIG. 1B shows sarcomere shortening and whole-cell calcium transients from isolated myocytes in each model. Data are from cells isolated from the lateral wall, although, as reported, $HF_{dys}$ and CRT models show similar behavior in both anterior and lateral walls (Chakir et al. (2009) *Circulation*. 119:1231-1240). Basal function (baseline) and peak calcium transient, as well as their stimulation by isoproterenol (ISO), were equally depressed in $HF_{dys}$ and $HF_{dys}$ models, but enhanced in both resynchronized models (V3A3 and CRT) back to near-control levels.

FIG. 1C shows a summary for results of peak rest and isoproterenol-stimulated shortening, cell relengthening velocity, peak calcium, and rate of calcium decline (n=12 to 20 cells per heart, n=4 to 5 hearts per group). All of the properties were depressed only in $HF_{dys}$ and $HF_{syn}$ models. * represents p<0.01 versus all other groups and † represents p<0.001 versus baseline.

FIG. 3A shows β-receptor maximal affinity binding ($B_{max}$) reflecting surface membrane receptor abundance for combined and individual $\beta_1$-AR and $\beta_2$-AR subtypes. n=4 for each group. * represents p<0.05 versus other HF groups and control (within respective receptor group) and † represents p<0.01 versus $\beta_2$-AR response. FIG. 3B shows sarcomere shortening (% SS) and whole-cell calcium transient in cells from different models when stimulated with isoproterenol without or with pretreatment by pertussis toxin (PTX). PTX treatment greatly enhanced both behaviors in $HF_{dys}$ and $HF_{syn}$, but had no impact in resynchronized models. FIG. 3C shows % SS and peak $Ca^{2+}$ transient in cells exposed to $\beta_2$-AR-selective agonist zinterol (ZIN), zinterol+PTX, or the $G_s$-biased $\beta_2$ agonist fenoterol. n=12 to 20 cells per heart and 3 to 4 hearts per group. * represents p<0.01 versus other groups; † represents p<0.001 versus zinterol; and ‡ represents p<0.001 versus fenoterol.

FIG. 4A shows that β-receptor binding affinity ($K_d$) was unaltered among the five different models. FIG. 4B shows the results of both high and low affinity binding.

FIG. 5A shows the effect of $\beta_1$-AR stimulation on myocyte sarcomere shortening and peak calcium transient in the experimental models. Maximal sarcomere shortening and calcium transient response to selective $\beta_1$ stimulation (combined norepinephrine, NE, and prazosin PRZ). Both responses were reduced in $HF_{dys}$ with less sarcomere shortening decline in $HF_{syn}$. Responses in resynchronization models were similar to that of the control. FIG. 5B shows gene expression results of $\beta_1$-AR and $\beta_2$-AR as assessed by quantitative PCR. A reduction was observed only in $HF_{dys}$. * represents p<0.05 versus other groups and † represents p<0.5 versus the control (Con).

FIG. 6A shows the domain structure of the ICUE3 FRET probe for analysis of membrane-localized cAMP generation. "GCIKSKRKDKDP" in FIG. 6D correspondence to SEQ ID NO: 27. Cells were studied in the presence of IBMX to inhibit PDEs and stimulated with either zinterol or fenoterol. FIG. 6B shows example of cell fluorescence ratio-encoded images from myocytes in each group showing enhanced cAMP generated in CRT models stimulated by zinterol. FIG. 6C shows time tracings for FRET ratio in cells stimulated with zinterol or fenoterol (upper panels), as well as a summary of data from all experiments (n=8 to 15 per group; lower panels). Zinterol induced a greater response in CRT models, whereas fenoterol led to a similarly elevated response in all groups. FIG. 6D shows the domain structure of the SR-AKAR3 FRET probe used for sarcoplasmic reticulum (SR)-localized PKA activity. "LRRATLVD" corresponds to SEQ ID NO: 28. "PQQARQKLQNLFINFCLILICLLLICIIVMLL" corresponds to SEQ ID NO: 29. FIG. 6E shows that myocyte expressing SR-AKAR3 exhibits fluorescence in tubular SR throughout the cell. FIG. 6F shows exemplary time tracings of SR-AKAR3 FRET in cells treated with zinterol. Only myocytes from CRT models showed PKA activation in the SR. Forskolin (Fsk) was used as a positive control to show functionality of the probe after direct AC stimulation (n=4 to 5 per group).

FIGS. 10A-10C show the up-regulation of RGS2 and RGS3 in canine models of resynchronization and human responders to chronic CRT. Western blots (FIG. 10A) and summary densitometry (FIG. 10B) for protein expression of RGS2, RGS3, and RGS4 (n=4 to 5 per group) are shown. The analyses were normalized to GAPDH as a loading control. * represents p<0.001 versus control (CON) and p<0.01 versus $HF_{dys}$ and $HF_{syn}$; † represents p<0.01 versus control and p<0.001 versus $HF_{dys}$ and $HF_{syn}$; and # represents p<0.001 versus all other groups. FIG. 10C shows that enhanced RGS2 and RGS3 mRNA expression is present in human LV biopsy samples from responder (R) patients, whereas it is absent in nonresponders (NR). Responders also demonstrated a significant decline in myocardial B-type natriuretic peptide (BNP). Differential response in EF is also displayed for the two groups.

FIG. 13A shows the results of isolated myocytes from HF$_{dys}$ hearts exposed to adenovirus with either GFP (control) or RGS2 and/or RGS3 vectors. Up-regulation of protein was confirmed in the myocytes and was in the range of 50 to 60% over controls. Adenovirus-GFP controls were similar to noninfected HF$_{dys}$ cells. * represents p<0.05 versus control (CON) and HF$_{dys}$ and † represents p<0.05 versus other groups. FIG. 13B shows summary data showing sarcomere shortening response to zinterol in myocytes from HF$_{dys}$, HF$_{syn}$, or CRT hearts after 24-hour infection with adenovirus containing GFP or full-length RGS2 and/or RGS3. Data are also shown with or without concomitant PTX treatment. n=12 to 18 cells per heart and n=2 to 3 hearts per group were used. * represents p<0.01 versus CRT and † represents p<0.001 versus CRT.

FIG. 14A shows that the % SS and peak Ca$^{2+}$ transients are similar at baseline and after isoproterenol stimulation in myocytes from an AVA heart to those observed after CRT. * represents p<0.001 versus baseline (nonstimulated). FIG. 14B shows minimal augmentation of functional or Ca$^{2+}$ response to zinterol in AVA myocytes by addition of PTX. Data are compared with the HF$_{syn}$ model, which displayed marked augmentation. * represents p<0.05 versus zinterol alone. n=12 to 20 cells per heart and n=4 hearts for each group was used. FIG. 14C shows protein expression for RGS3 and RGS2 in the AVA model, as shown in comparison with the HF$_{syn}$ model. There was no up-regulation in this model, unlike CRT (n=4 to 5 per model). FIG. 14D shows protein expression (left) and summary densitometry (right) for β-arrestin2, which is shown in comparison to the HF$_{syn}$ data. Unlike HF$_{syn}$, which had no change in expression over control or the other models (see FIG. 7), AVA myocytes had very low levels. * represents p<0.001.

FIGS. 19A-19D show mycocyte results. FIG. 19A shows an example of a single skinned myocyte attached to the force transducer and motor arm at 40× magnification. FIG. 19B shows data points and a fitted curve for control, HF$_{dys}$, CRT, and HF$_{sync}$ from skinned myocytes isolated from the LV lateral wall. FIGS. 19C and 19D show F$_{max}$ and EC$_{50}$ for the four groups. * represents p<0.05 versus control and † represents p<0.05 versus HF$_{dys}$.

FIGS. 20A-20C show force-calcium relationships. FIG. 20A shows representative force-calcium relationships for control, CRT, and HF$_{dys}$ before (closed circles) and after (open circles) PP1 treatment. FIG. 20B shows the change in F$_{max}$ with PP1 treatment. No significant changes were observed. FIG. 20C shows the change in EC$_{50}$ after PP1 treatment. * represents p<0.05 versus control and † represents p<0.05 versus HF$_{dys}$.

FIG. 21A shows a Western blot for cTnI run on a phos-Tag gel with the phosphorylation bands arbitrarily labeled as unphosphorylated (0P) through 2P for control, HF$_{dys}$, CRT, and HF$_{sync}$ samples. FIG. 21B shows a quantification of each band, which has been normalized to the total intensity of all TnI bands in that lane (% of total TnI).

BRIEF DESCRIPTION OF THE TABLES

Figure 1B:
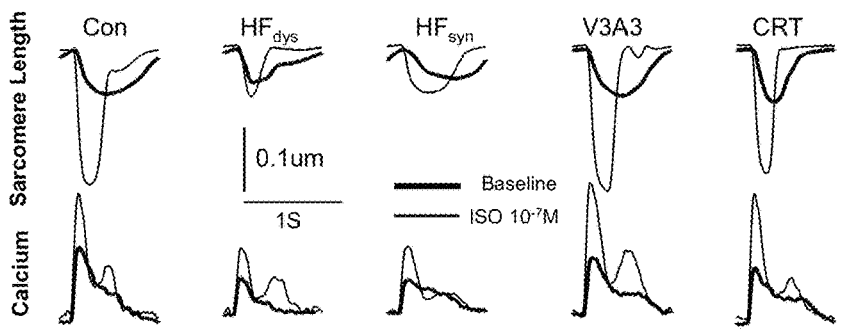

Table 1 shows a list of nucleic acid and amino acid sequences of representative RGS2 and RGS3 genes.

Table 2 shows a list of phosphorylation sites of myofilament phosphorylated proteins in canine pacing models. Myofilament phospho-peptide enriched samples were run on an Orbitrap mass spectrometer and phosphorylation sites were identified in each group (n=4 dogs). The table shows phosphorylation sites which were present in one or two groups, but not all three. MyBPC refers to myosin binding protein C and Tm refers to tropomyosin.

DETAILED DESCRIPTION OF THE INVENTION

The present invention is based in part on the elucidation of methods and mechanisms useful for diagnosing, prognosing, and treating cardiac-related disorders, such as heart failure.

Some embodiments of the present invention are directed to methods using RGS2 and/or RGS3 compositions. Nucleic acid sequences described and/or claimed herein can be altered or designed to encode the same or a substantially similar amino acid sequence or protein having the desired biological activities. In addition, the amino acid sequences or proteins of the present invention can be altered or modified according to methods known in the art to have different sequences yet still be capable of exhibiting the desired biological activities. It is to be understood that the specific amino acid sequences and proteins described herein include sequences and proteins that are substantially similar or homologous thereto or those that can be modified in a manner contemplated by those skilled in the art without departing from the spirit and operation of the present invention.

In order that the present invention can be more readily understood, certain terms are first defined. Additional definitions are set forth throughout the detailed description.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives can comprise a protein or chemical moiety conjugated to an antibody. The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., RGS2 and/or RGS3 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Still further, an antibody or antigen-binding portion thereof can be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein. Antibodies can be polyclonal or monoclonal; xenogeneic, allogeneic, or syngeneic; or modified forms thereof (e.g., humanized, chimeric, etc.). Antibodies can also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "binding" or "interacting" refers to an association, which can be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" is intended to include tissues, cells and biological fluids isolated from a subject, as well as tissues, cells and fluids present within a subject.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit). In some embodiments, media described herein can contain or comprise body fluids.

The term "cardiac contractility" or "myocardial contractility" refer to measures of cardiac function, which may include but are not limited to cardiac output, ejection fraction, fractional shortening, cardiac work, cardiac index, chronotropy, lusitropy, velocity of circumferential fiber shortening, velocity of circumferential fiber shortening corrected for heart rate, stroke volume, rates of cardiac contraction or relaxation, the first derivatives of interventricular pressure (maximum dP/dt and minimum dP/dt), ventricular volumes, clinical evaluations of cardiac function (for example, stress echocardiography and treadmill walking) and variations or normalizations of these parameters. These parameters may be measured in humans or animals alike to assess myocardial function and assist in diagnosis and prognosis of cardiac-related disorders.

The term "cardiac-related disorder" refers to any disorder or condition involving cardiac muscle tissue or cardiac dysfunction. Disorders involving cardiac muscle tissue include, but are not limited to, myocardial disease, including but not limited to dilated cardiomyopathy, hypertrophic cardiomyopathy, restrictive cardiomyopathy, myocardial stunning, and myocarditis; heart failure; acute heart failure; rheumatic fever; rhabdomyoma; sarcoma; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia; disorders involving cardiac transplantation; arterial hypertension; peripartum cardiomyopathy; alcoholic cardiomyopathy; tachycardias; supraventricular tachycardia; bradycardia; atrial flutter; hydrops fetalis; arrhythmias; extrasystolic arrhythmia; fetal cardiac arrhythmia; endocarditis; atrial fibrillation; idiopathic dilated cardiomyopathy; Chagas' heart disease; long QT syndrome; Brugada syndrome; ischemia; hypoxia; ventricular fibrillation; ventricular tachycardia; restenosis; congestive heart failure; syncope; arrythmias; pericardial disease; myocardial infarction; unstable angina; stable angina; and angina pectoris, viral myocarditis, and non-proliferating cell disorders involving cardiac muscle tissue.

The term "complex" refers to an association between at least two moieties (e.g. chemical or biochemical) that have an affinity for one another. "Protein complex" or "polypeptide complex" refers to a complex comprising at least one or more polypeptides.

The term "effective amount" refers to an amount sufficient to achieve a desired result. For example, a "prophylactically effective amount" refers to an amount sufficient to reduce the likelihood of a disorder from occurring. In addition, a "therapeutically effective amount" refers to an amount effective to slow, stop or reverse the progression of a disorder.

The term "heart cell" refers to a cell which can be: (a) part of a heart present in a subject, (b) part of a heart which is maintained ex vivo, (c) part of a heart tissue, or (d) a cell which is isolated from the heart of a subject. For example, the cell can be a muscle cell, such as a cardiac myocyte (cardiomyocyte) or smooth muscle cell. Heart cells of the invention can also include endothelial cells within the heart, for example, cells of a capillary, artery, or other vessel.

The term "heart failure" generally refers to any disorder in which the heart has a defect in its ability to pump adequately to meet the body's needs. In many cases, heart failure is the result of one or more abnormalities at the cellular level in the various steps of excitation-contraction coupling of the cardiac cells. It is most frequently due to a defect in myocardial contraction, which can occur for many reasons, the most common of which include: ischemic damage to the myocardium, excessive mechanical resistance to the outflow of blood from the heart, overloading of the cardiac chambers due to defective valve function, infection or inflammation of the myocardium, or congenitally poor myocardial contractile function (Braunwald (2001) Harrison's Principles of Internal Medicine, 15th ed., pp 1318-29).

The term "inhibit" includes the decrease, limitation, or blockage, of, for example a particular action, function, or interaction. For example, a cardiac-related disorder is "inhibited" if at least one symptom of the disease, such as reduced mechanical efficiency, is alleviated, terminated, slowed, or prevented. As used herein, a cardiac-related disorder is also "inhibited" if recurrence of a disease symptom is reduced, slowed, delayed, or prevented. Such an inhibition can affect a cardiac-mediated activity (e.g., blood pressure, blood flow rates, and the like). For example, a cardiac-mediated activity can be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more or any range in between. The terms "increase," "enhance," "promote," and the like can be used in the exact opposite manner as "inhibit."

The term "isolated polypeptide" refers to a polypeptide that (1) is not associated with proteins that it is normally found within nature, (2) is isolated from the cell in which it normally occurs, (3) is substantially free of other proteins from the same cellular source, (4) is expressed by a cell from a different species, or (5) does not occur in nature. The term "substantially free of cellular material" includes preparations of protein in which the protein is separated from cellular components of the cells in which it is naturally or recombinantly produced. In one embodiment, the language "substantially free of cellular material" includes preparations of RGS2 and/or RGS3 protein having less than about 30% (by dry weight) of non-RGS2 and/or RGS3 protein (also referred to herein as a "contaminating protein"), more preferably less than about 20% of non-RGS2 and/or RGS3 protein, still more preferably less than about 10% of non-RGS2 and/or RGS3 protein, and most preferably less than about 5% non-RGS2 and/or RGS3 protein. When the protein is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of RGS2 and/or RGS3 protein in which the protein is separated from chemical precursors or other chemicals which are involved in the synthesis of the protein. In one embodiment, the language "substantially free of chemical precursors or other chemicals" includes preparations of RGS2 and/or RGS3 protein having less than about 30% (by dry weight) of chemical precursors of non-RGS2 and/or RGS3 chemicals, more preferably less than about 20% chemical precursors of non-RGS2 and/or RGS3 chemicals, still more preferably less than about 10% chemical precursors of non-RGS2 and/or RGS3 chemicals, and most preferably less than about 5% chemical precursors of non-RGS2 and/or RGS3 chemicals. In preferred embodiments, isolated proteins or biologically active portions thereof lack contaminating proteins from the same animal from which the RGS2 and/or RGS3 protein is derived. Typically, such proteins are produced by recombinant expression of, for example, a human RGS2 and/or RGS3 protein in a nonhuman cell. Similar considerations apply for "isolated nucleic acids."

The term "substantially altered," "substantially modulated," and the like, unless otherwise defined, refers to a deviation of a measured attribute in comparison to a reference control. The deviation can be measured according to quantitative or qualitative means. In one embodiment, the attribute's alteration is greater than 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200% or more or any range in between different relative to the control.

The terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

An "overexpression" or "significantly higher level of expression or copy number" of a marker refers to an expression level or copy number in a test sample that is greater than the standard error of the assay employed to assess expression or copy number, and is preferably at least twice, and more preferably three, four, five or ten or more times the expression level or copy number of the marker in a control sample (e.g., sample from a healthy subject not afflicted with a cardiac-related disorder) and preferably, the average expression level or copy number of the marker in several control samples.

The term "response to therapy" relates to any response of the cardiac-related disorder to a therapy. Responses can be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of cardiac-related disorder response can be done early after the onset of therapy, e.g., after a few hours, days, weeks or preferably after a few months. Additional criteria for evaluating the response to therapies are related to "survival," which includes all of the following: survival until mortality, also known as overall survival (wherein said mortality can be either irrespective of cause or tumor related); "recurrence-free survival" (e.g., viral load below a detectable threshold); metastasis free survival; disease free survival. The length of said survival can be calculated by reference to a defined start point (e.g., time of diagnosis or start of treatment) and end point (e.g., death, recurrence or metastasis). In addition, criteria for efficacy of treatment can be expanded to include response to therapy, probability of survival, probability of disease manifestation recurrence within a given time period. For example, in order to determine appropriate threshold values, a particular therapeutic regimen can be administered to a population of subjects and the outcome can be correlated to viral load or other measurements that were determined prior to administration of any therapy. Alternatively, outcome measures, such as overall survival and disease-free survival can be monitored over a period of time for subjects following therapy for whom measurement values are known.

The term "RGS" refers to a family of regulators of G-protein signaling which affect the intensity and duration of the G-protein signal cascade by binding to the active $G\alpha$-GTP-$Mg^{2+}$ complex to increase the rate of GTP hydrolysis. RGS proteins act as attenuators of the induced G-protein signal by increasing the rate of inactivation of the G-protein and termination of the signal. RGS proteins have been identified in a wide range of eukaryotes, including humans. RGS proteins are highly diverse, multifunctional proteins characterized by the presence of a core region of approximately 130 amino acid residues (sometimes identified as having 120 amino acids), which may be separated by linker regions of varying lengths, that is conserved in all RGS proteins that have so far been identified. All RGS proteins that have been identified bind to members of the $G\alpha_i$ class of G protein subunits. The family of RGS proteins include RGS2, RGS3, RGS4, GAIP (human $G\alpha$-interacting protein), RGS 1, RGS 10, RGS 11, RGS12, RGS13, RGS14, and RGS16 (also called RGSr), Axin, Conductin, p115-RhoGEF, PD2-RhoGEF and LSC, among others, and contains more than 20 known members where specificity for $G\alpha$ subtypes has been demonstrated and appears to be associated with subtle sequence differences. The conserved region of RGS provides for binding to $G\alpha$ and can thus be used to identify species that affect (as agonists or antagonists) RGS binding to $G\alpha$ and the activity of RGS as an attenuator of G-protein signaling. The term "RGS protein," including its use for specific RGS proteins and RGS protein subfamilies, includes native RGS proteins (and native RGS core proteins) isolated from or otherwise obtained from (e.g., by expression of cloned genes) from any natural sources, recombinant RGS proteins which may contain portions of RGS sequence and non-RGS sequence (e.g., RGS-core sequence with the hexahis pro-tag), variant RGS proteins which contain conservative amino acid sequence differences from a native RGS protein or in which sequences non-functional in RGS activity are deleted, mutant RGS proteins in which one or more amino acids have been modified by expression from a mutant RGS coding sequence. Mutants include, among others, those having one or more site specific mutations, those having one or more deletions and those having one or more insertions compared to a native RGS protein (or RGS-core) or variant RGS (or variant RGS-core). The term "mutant RGS" refers in particular to those proteins having the described mutations, insertions or deletions in the RGS core region. Variant RGS proteins are expected to have biological function for G-protein regulation substantially the same as that of the native RGS protein from which they are derived. Mutant RGS proteins include those which have biological function substantially the same as or modified from that of a native or variant RGS protein from which they are derived. Variant, derivative, recombinant and mutant RGS proteins do not necessarily represent mutually exclusive subsets of proteins.

The term "RGS2" refers to a specific RGS family member. The sequence of the human RGS2 transcript is available to the public at the GenBank database under NM_002923.3 and NP_002914.1. Nucleic acid and polypeptide sequences of RGS2 orthologs in organisms other than humans are well known and include, for example, mouse RGS2 (NM_009061.4 and NP_033087.2), chimpanzee RGS2 (XM_001166601.2 and XP_001166601.1), rat RGS2 (NM_053453.2 and NP_445905.1), cow RGS2 (NM_001075596.1 and NP_001069064.1), dog RGS2 (XM_545701.3 and XP_545701.2), and chicken RGS2 (NM_204395.1 and NP_989726.1).

The term "RGS3" refers to another specific RGS family member. At least six transcript variants encoding two different human RGS3 proteins exist. The sequence of human RGS3 transcript variant 6, also known as C2PA-RGS3, encodes the longest protein isoform and is available to the public at the GenBank database under NM_144488.4 and NP_652759.3. The sequence of human RGS3 transcript variant 1, also known as PDZ-RGS3 and publicly available under NM_130795.2 and NP_570613.2, differs in the 5' coding region relative to variant 6 and therefore encodes a shorter and distinct N-terminus compared to isoform 6. The sequence of human RGS3 transcript variant 2, which is publicly available under NM_021106.3 and NP_066929.1, lacks multiple 5' exons and contains an alternate 5' end relative to variant 6 and therefore encodes a much shorter N-terminus compared to isoform 6. The sequence of human RGS3 transcript variant 3, which is publicly available under NM_017790.3 and NP_060260.3, lacks several 3' exons and contains alternate 5' and 3' coding regions relative to variant 6 and therefore encodes shorter and distinct N- and C-termini compared to isoform 6. The sequence of human RGS3 transcript variant 4, which is publicly available under NM_134427.1 and NP_602299.1, lacks multiple 5' exons and contains an alternate 5' untranslated region (UTR) relative to variant 6 and therefore encodes a much shorter N-terminus compared to isoform 6. The sequence of human RGS3 transcript variant 5, also known as RGS3S and publicly available under NM_144489.2 and NP_652760.2, lacks multiple 5' exons and contains an alternate 5' coding exon relative to variant 6 and therefore encodes a shorter and distinct N-terminus compared to isoform 6. Nucleic acid and polypeptide sequences of RGS3 orthologs in organisms other than humans are well known and include, for example, mouse RGS3 (NM_001081650.1 and NP_001075119.1; NM_019492.2 and NP_062365.2; and NM_134257.3 and NP_599018.3), chimpanzee RGS3 (XM_001154862.2 and XP_001154862.1; XM_0011545695.2 and XP_001154695.1; XM_001154042.2 and XP_001154042.1; XM_001154922.2 and XP_001154922.1; XM_003312245.1 and XP_003312293.1; XM_003312246.1 and XP_003312294.1; XM_003312243.1 and XP_003312291.1; XM_003339180.1 and XP_003339228.1; and XM_003312242.1 and XP_003312290.1), rat RGS3 (NM_019340.1 and NP_062213.1), cow RGS3 (NM_001077973.1 and NP_001071441.1), dog RGS3 (XM_848562.1 and XP_853655.1), and chicken RGS3 (NM_204459.1 and NP_989790.1).

The term "subject" refers to any healthy animal, mammal or human, or any animal, mammal or human afflicted with a cardiac-related disorder.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality can be either irrespective of cause or tumor related); "recurrence-free survival" (wherein the term recurrence shall include both localized and distant recurrence); disease free survival (wherein the term disease shall include antiviral infection and diseases associated therewith). The length of said survival can be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of disease recurrence. In some embodiments, mortality is measured in terms of survival rates.

A "tissue-specific" promoter is a nucleotide sequence which, when operably linked with a polynucleotide which encodes or specifics a gene product, causes the gene product to be produced in a living human cell substantially only if the cell is a cell of the tissue type corresponding to the promoter. For example, quantitative or tissue specificity upstream elements from cardiac-specific promoters may be used to express a gene product in cardiac tissue or cells thereof. Many such elements have been characterized and include, without limitation, the murine TIMP-4 promoter, A and B-type natriuretic peptide promoters, human cardiac troponin I promoter, murine S100A1 promoter, salmon cardiac peptide promoter, GATA response element, rabbit β-myosin promoter, and mouse α-myosin heavy chain promoter (Rahkonen, et al. (2002) Biochem Biophys Acta 1577:45-52; Thuerauf and Glembotski (1997) J. Biol. Chem. 272:7464-7472; LaPointe et al (1996) Hypertension 27:715-722; Grepin et al. (1994) Mol. Cell Biol. 14:3115-29; Dellow, et al. (2001) Cardiovasc. Res. 50:3-6; Kiewitz, et al. (2000) Biochem Biophys Acta 1498:207-19; Majalahti-Palviainen, et al (2000) Endocrinology 141:731-740; Charron et al. (1999) Molecular & Cellular Biology 19:4355-4365; Genbank 071441; U.S. Provisional Patent Application Nos. 60/393,525 and 60/454,947; and U.S. patent application Ser. No. 10/613,728). In addition, cardiac tissue preferred promoter elements from the following genes can be used: myosin light chain-2, .alpha.-myosin heavy chain, AE3, cardiac troponin C, and cardiac .alpha.-actin. See, e.g. Franz et al (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol Cell Biol. 14:1870-1885; Hunter et al. (1993) Hypertension 22:608-617; and Sartorelli et al. (1992) Proc. Natl. Acad. Sci. USA 89:4047-4051. In some embodiments, the coding region is operably linked to an inducible regulatory element or elements. A variety of inducible promoter systems has been described in the literature and can be used in the present invention. A known and useful conditional system is the binary, tetracycline-based system, which has been used in both cells and animals to reversibly induce expression by the addition or removal of tetracycline or its analogues. Another example of such a binary system is the cre/loxP recombinase system of bacteriophage P1. For a description of the cre/loxP recombinase system, see, e.g., Lakso et al. (1992) PNAS 89:6232-6236. Another class of promoter elements are those which activate transcription of an operably linked nucleotide sequence of interest in response to hypoxic conditions. These include promoter elements regulated at least in part by hypoxia inducible factor-1. Hypoxia response elements include, but are not limited to, the erythropoietin hypoxia response enhancer element (HREE1), the muscle pyruvate kinase HRE; the .beta.-enolase HRE; and endothelin-1 HRE element, and chimeric nucleotide sequence comprising these sequences. See Bunn and Poynton (1996) Physiol. Rev. 76:839-885; Dachs and Stratford (1996) Br. J. Cancer 74:S126-S132; Guillemon and Krasnow (1997) Cell 89:9-12; Firth et al. (1994) Proc. Natl. Acad. Sci. 91:6496-6500; Jiang et al. (1997) Cancer Res. 57:5328-5335; U.S. Pat. No. 5,834,306). It is further recognized that to increase transcription levels or to alter tissue specificity, enhancers and/or tissue-preference elements may be utilized in combination with a given promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cardiac-related disorder) and preferably, the average expression level or copy number of the marker in several control samples.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet can be employed (illustrated above). Therefore, a number of different nucleotide sequences can code for a given amino acid sequence. Such nucleotide sequences are considered functionally equivalent since they result in the production of the same amino acid sequence in all organisms (although certain organisms can translate some sequences more efficiently than they do others). Moreover, occasionally, a methylated variant of a purine or pyrimidine can be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Before the present invention is further described, it will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein are well known in the art and can be used in the embodiments of the invention.

It is further to be understood that this invention is not limited to particular embodiments described, as such can, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an RGS2 complex" includes a plurality of such complexes and reference to "the active agent" includes reference to one or more active agents and equivalents thereof known to those skilled in the art, and so forth. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

I. Isolated Nucleic Acids

One aspect of the invention pertains to isolated nucleic acid molecules that encode RGS2 and/or RGS3 polypeptides useful for diagnosing, prognosing, and treating cardiac-related disorders. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated RGS2 and/or RGS3 nucleic acid molecule can contain less than about 5 kb, 4 kb, 3 kb, 2 kb, 1 kb, 0.5 kb or 0.1 kb of nucleotide sequences which naturally flank the nucleic acid molecule in viral DNA. Moreover, an "isolated" nucleic acid molecule, such as a cDNA molecule, can be substantially free of other cellular material, or culture medium when produced by recombinant techniques, or chemical precursors or other chemicals when chemically synthesized.

A RGS2 and/or RGS3 nucleic acid molecule of the present invention, e.g., a nucleic acid molecule having the nucleotide sequence of a RGS2 and/or RGS3 polypeptide-encoding nucleic acid sequence shown in Table 1, or a nucleotide sequence which is at least about 50%, preferably at least about 60%, more preferably at least about 70%, yet more preferably at least about 80%, still more preferably at least about 90%, and most preferably at least about 95%, 96%, 97%, 98%, 99% or more identical to such nucleotide sequences, can be engineered and isolated using standard molecular biology techniques and the sequence information provided herein (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, such nucleic acids can be isolated by the polymerase chain reaction using oligonucleotide primers designed based upon RGS2 and/or RGS3 sequences. For example, RNA or DNA can be isolated from RGS2 and/or RGS3 nucleic acid (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an RGS2 and/or RGS3 nucleotide sequence of the present invention can be prepared by standard synthetic techniques, i.e., using an automated DNA synthesizer.

Probes based on RGS2 and/or RGS3 nucleotide sequences of the present invention can be used to detect homologs in related organisms. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an RGS2 and/or RGS3 protein, such as by measuring a level of an RGS2 and/or RGS3-encoding nucleic acid in a sample of cells from a subject, i.e., detecting RGS2 and/or RGS3 RNA levels.

Nucleic acid molecules encoding other RGS2 and/or RGS3 members and thus which have a nucleotide sequence which differs from the RGS2 and/or RGS3 sequences shown in Table 1, or fragment thereof, are contemplated. In one embodiment, the nucleic acid molecule(s) of the present invention encodes a protein or portion thereof which includes an amino acid sequence which is sufficiently homologous to a RGS2 and/or RGS3 amino acid sequence shown in Table 1, or fragment thereof, such that the protein or portion thereof maintains or enhances one or more of the following biological activities: a) increased heart chamber mechanical efficiency; b) increased β-adrenergic receptor numbers and/or density; c) inhibited $G\alpha_i$ signaling; d) increased Gas-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality.

In another embodiment, the nucleic acid encodes an RGS2 and/or RGS3 protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an RGS2 and/or RGS3 polypeptide amino acid sequence (e.g., a sequence shown in Table 1), or a fragment thereof.

The invention further encompasses RGS2 and/or RGS3 nucleic acid molecules that differ from the nucleotide sequences shown in an RGS2 and/or RGS3 polypeptide-encoding nucleic acid sequence shown in Table 1. In one embodiment, an isolated nucleic acid molecule of the invention has a nucleotide sequence encoding a protein having an RGS2 and/or RGS3 polypeptide amino acid sequence shown in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to an RGS2 and/or RGS3 polypeptide amino acid sequence shown in Table 1.

It will be appreciated by those skilled in the art that DNA sequence polymorphisms that lead to changes in the amino acid sequences of RGS2 and/or RGS3 can exist within a population (e.g., a mammalian and/or human population). Such genetic polymorphism in the RGS2 and/or RGS3 gene can exist among individuals within a population due to natural allelic variation. As used herein, the terms "gene" and "recombinant gene" refer to nucleic acid molecules comprising an open reading frame encoding an RGS2 and/or RGS3 protein, preferably a mammalian, e.g., human, RGS2 and/or RGS3 protein. Such natural allelic variations can typically result in 1-5% variance in the nucleotide sequence of the RGS2 and/or RGS3 gene. Any and all such nucleotide variations and resulting amino acid polymorphisms in RGS2 and/or RGS3 that are the result of natural allelic variation and that do not alter the functional activity of RGS2 and/or RGS3 are intended to be within the scope of the invention.

In addition to naturally-occurring allelic variants of the RGS2 and/or RGS3 sequence that can exist in the population, the skilled artisan will further appreciate that changes can be introduced by mutation into the nucleotide sequence of an RGS2 and/or RGS3 polypeptide-encoding nucleic acid sequence shown in Table 1, or fragment thereof, thereby leading to changes in the amino acid sequence of the encoded RGS2 and/or RGS3 protein, without altering the functional ability of the RGS2 and/or RGS3 protein. For example, nucleotide substitutions leading to amino acid substitutions at "non-essential" amino acid residues can be made in the sequences. A "non-essential" amino acid residue is a residue that can be altered from the wild-type sequence of an RGS2 and/or RGS3 polypeptide (e.g., an RGS2 and/or RGS3 polypeptide amino acid sequence shown in Table 1, or fragment thereof) without substantially altering one or more biological activities of the polypeptide, whereas an "essential" amino acid residue does substantially alter such biological activities. Other amino acid residues, however, (e.g., those that are not conserved or only semi-conserved between mouse and human) cannot be essential for activity and thus are likely to be amenable to alteration without altering RGS2 and/or RGS3 activity.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna. CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding an RGS2 and/or RGS3 protein homologous to an RGS2 and/or RGS3 polypeptide amino acid sequence (e.g., a sequence shown in Table 1), or fragment thereof, can be created by introducing one or more nucleotide substitutions, additions or deletions into the nucleotide sequence of an RGS2 and/or RGS3 polypeptide-encoding nucleic acid sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in RGS2 and/or RGS3 is preferably replaced with another amino acid residue from the same side chain family. Alternatively, in another embodiment, mutations can be introduced randomly along all or part of an RGS2 and/or RGS3 coding sequence, such as by saturation mutagenesis, and the resultant mutants can be screened for an RGS2 and/or RGS3 activity described herein to identify mutants that retain RGS2 and/or RGS3 activity. Following mutagenesis, the encoded protein can be expressed recombinantly (as described herein) and the activity of the protein can be determined using, for example, assays described herein.

RGS2 and/or RGS3 protein levels can be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In some embodiments, RGS2 and/or RGS3 expression levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In other embodiments, the RGS2 and/or RGS3 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays.

As an alternative to making determinations based on the absolute RGS2 and/or RGS3 expression level, determinations can be based on the normalized RGS2 and/or RGS3 expression level. Expression levels are normalized by correcting the absolute RGS2 and/or RGS3 expression level by comparing its expression to the expression of a non-RGS2 and/or RGS3 gene, e.g., a housekeeping or other reference gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of an RGS2 and/or RGS3 protein can also be detected and/or quantified by detecting or quantifying the expressed polypeptide. The RGS2 and/or RGS3 polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express RGS2 and/or RGS3.

II. Recombinant Expression Vectors and Host Cells

Another aspect of the invention pertains to the use of vectors, preferably expression vectors, containing a nucleic acid encoding RGS2 and/or RGS3 (or a portion or complex thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising an RGS2 and/or RGS3 nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of RGS2 and/or RGS3 in prokaryotic or eukaryotic cells. For example, RGS2 and/or RGS3 can be expressed in bacterial cells such as *E. coli*, insect cells (using baculovirus expression vectors) yeast cells or mammalian cells. Suitable host cells are discussed further in Goeddel, *Gene Expression Technology: Methods*

*in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence is cloned into a pGEX expression vector to create a vector encoding a fusion protein comprising, from the N-terminus to the C-terminus, and/or GST-thrombin cleavage site. The fusion protein can be purified by affinity chromatography using glutathione-agarose resin. Recombinant RGS2 and/or RGS3 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the RGS2 and/or RGS3 expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, RGS2 and/or RGS3 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications can occur in succeeding generations due to either mutation or environmental influences, such progeny cannot, in fact, be identical to the parent cell, but are still included within the scope of the term as used herein.

A host cell can be any prokaryotic or eukaryotic cell. For example, RGS2 and/or RGS3 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art. In some embodiments, the host cell choice is determined according to the desire for glycosylation and, if so, the desired pattern of glycosylation. For example, polypeptides of the present invention can be produced using mammalian cell lines to produce polypeptides having mammalian patterns of glycosylation. Mammalian cell lines include, for example, monkey kidney CV1 line transformed by SV40 (COS-7); human embryonic kidney line 293; baby hamster kidney cells (BHK); Chinese hamster ovary-cells-DHFR$^+$ (CHO); Chinese hamster ovary-cells DHFR-(DXB11); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127); and myeloma cell lines.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. An RGS2 and/or RGS3 polypeptide or fragment thereof, can be secreted and isolated from a mixture of cells and medium containing the polypeptide. Alternatively, an RGS2 and/or RGS3 polypeptide or fragment thereof, can be retained cytoplasmically and the cells harvested, lysed and the protein or protein complex isolated. An RGS2 and/or RGS3 polypeptide or fragment thereof, can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of RGS2 and/or RGS3 or a fragment thereof. In other embodiments, heterologous tags can be used for purification purposes (e.g., epitope tags and FC fusion tags), according to standards methods known in the art.

Thus, a nucleotide sequence encoding all or a selected portion of an RGS2 and/or RGS3 polypeptide can be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, can be employed to prepare recombinant RGS2 and/or RGS3 polypeptides, or fragments thereof, by microbial means or tissue-culture technology in accord with the subject invention.

In another variation, protein production can be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system can be used. Such systems typically comprise at least an RNA polymerase holoenzyme, ribonucleotides and any necessary transcription initiation, elongation and termination factors. In vitro transcription and translation can be coupled in a one-pot reaction to produce proteins from one or more isolated DNAs.

In certain embodiments, the RGS2 and/or RGS3 polypeptide, or fragment thereof, can be synthesized chemically, ribosomally in a cell free system, or ribosomally within a cell. Chemical synthesis can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full-length ligation products are chemically identical to proteins produced by cell free synthesis. Full length ligation products can be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding RGS2 and/or RGS3 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) RGS2 and/or RGS3 protein. Accordingly, the invention further provides methods for producing RGS2 and/or RGS3 protein using the host cells of the invention. In one embodiment, the method comprises culturing the host cell of invention (into which a recombinant expression vector encoding RGS2 and/or RGS3 has been introduced) in a suitable medium until RGS2 and/or RGS3 is produced. In another embodiment, the method further comprises isolating RGS2 and/or RGS3 from the medium or the host cell.

III. Isolated RGS2 and/or RGS3 Polypeptides and Anti-RGS2 and/or Anti-RGS3 Antibodies The present invention further provides isolated RGS2 and/or RGS3 polypeptides, or fragments thereof. In one aspect, an RGS2 and/or RGS3 polypeptide can comprise a full-length RGS2 and/or RGS3 amino acid sequence or a full-length RGS2 and/or RGS3 amino acid sequence with 1, 2, 3, 4, 5, 6, 7, 8, 9, 10, 11, 12, 13, 14, 15, 16, 17, 18, 19, or 20 or more 20 conservative amino acid substitutions. In one embodiment, the RGS2 and/or RGS3 polypeptides have an RGS2 and/or RGS3 polypeptide amino acid sequence shown in Table 1, or a fragment thereof. In another embodiment, the RGS2 and/or RGS3 polypeptides have an amino acid sequence that is at least 50, 55, 60, 65, 70, 75, 80, 85, 90, 91, 92, 93, 94, 95, 96, 97, 98, 99, or 99.5% identical to the entire amino acid sequence of an RGS2 and/or RGS3 polypeptide amino acid sequence shown in Table 1, or a fragment thereof. In addition, any RGS2 and/or RGS3 polypeptide of the present invention, or fragment thereof, maintains or enhances one or more of the following biological activities: maintains or enhances one or more of the following biological activities: a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. In another aspect, the present invention contemplates a composition comprising an isolated RGS2 and/or RGS3 polypeptide and less than about 25%, or alternatively 15%, or alternatively 5%, contaminating biological macromolecules or polypeptides.

In certain embodiments, an RGS2 and/or RGS3 polypeptide of the invention can be a fusion protein containing a domain which increases its solubility and bioavailability and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, an RGS2 and/or RGS3 polypeptide of the invention can comprise one or more heterologous fusions. Polypeptides can contain multiple copies of the same fusion domain or can contain fusions to two or more different domains. The fusions can occur in within the polypeptide as an in-frame insertion, at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide can be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, RGS2 and/or RGS3 polypeptides, or fragments thereof, are fused to an antibody fragment (e.g., Fc polypeptides). Techniques for preparing these fusion proteins are known, and are described, for example, in WO 99/31241 and in Cosman et. al., 2001 Immunity 14:123 133. Fusion to an Fc polypeptide offers the additional advantage of facilitating purification by affinity chromatography over Protein A or Protein G columns.

In still another embodiment, an RGS2 and/or RGS3 polypeptide can be labeled with a fluorescent label to facilitate their detection, purification, or structural characterization. In an exemplary embodiment, an RGS2 and/or RGS3 polypeptide of the invention can be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFP-mut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Fragments or biologically active portions of the RGS2 and/or RGS3 proteins can include polypeptides comprising amino acid sequences derived from the amino acid sequence of the RGS2 and/or RGS3 protein, e.g., an RGS2 and/or RGS3 polypeptide amino acid sequence shown in Table 1, or fragment thereof, which include fewer amino acids than the full-length RGS2 and/or RGS3 protein, and exhibit at least one activity of the RGS2 and/or RGS3 protein, or complex thereof. In one embodiment, an RGS2 and/or RGS3 protein can have 1, 2, 3, 4, 5, 6, 7, 8, 9, 10, 11, 12, 13, 14, 15, 16, 17, 18, 19, 20 or more fewer amino acids, whether contiguous or not contiguous. For example, deletion or replacement of certain sequences (e.g., the proteolytic cleavage site, signal sequence, and the like) that do not substantially affect desired biological activities of RGS2 and/or RGS3 polypeptides are contemplated.

RGS2 and/or RGS3 proteins described herein can be produced by recombinant DNA techniques. For example, a nucleic acid molecule encoding the protein is cloned into an expression vector (as described above), the expression vector is introduced into a host cell (as described above) and the RGS2 and/or RGS3 protein is expressed in the host cell. The RGS2 and/or RGS3 protein can then be isolated from the cells by an appropriate purification scheme using standard protein purification techniques. Alternative to recombinant expression, an RGS2 and/or RGS3 protein, polypeptide, or peptide can be synthesized chemically using standard peptide synthesis techniques. Moreover, native RGS2 and/or RGS3 protein can be isolated from cells (e.g., cardiac muscle cells), for example, using an anti-RGS2 and/or RGS3 antibody (described further below).

The full-length RGS2 and/or RGS3 protein can be used or, alternatively, antigenic peptide fragments of RGS2 and/or RGS3, or peptides in complex, can be used as immunogens. An RGS2 and/or RGS3 polypeptide of the present invention can be used to prepare antibodies by immunizing a suitable subject, (e.g., human, monkey, rabbit, goat, mouse or other mammal) with the immunogen as further described herein. An appropriate immunogenic preparation can contain, for example, recombinantly expressed RGS2 and/or RGS3 protein or a chemically synthesized RGS2 and/or RGS3 polypeptide. The preparation can further include an adjuvant, such as Freund's complete or incomplete adjuvant, or similar immunostimulatory agent. Immunization of a suitable subject with an immunogenic RGS2 and/or RGS3 polypeptide that induces a polyclonal anti-RGS2 and/or RGS3 antibody response.

Accordingly, another aspect of the invention pertains to the use of anti-RGS2 and/or RGS3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as RGS2 and/or RGS3. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind RGS2 and/or RGS3. The term "monoclonal antibody" or "monoclonal antibody composition", as used herein, refers to a population of antibody molecules that contain only one species of an antigen binding site capable of immunoreacting with a particular epitope of RGS2 and/or RGS3. A monoclonal antibody composition thus typically displays a single binding affinity for a particular RGS2 and/or RGS3 protein with which it immunoreacts.

Polyclonal anti-RGS2 and/or RGS3 antibodies can be prepared as described above by immunizing a suitable subject with an RGS2 and/or RGS3 immunogen, or fragment thereof. The anti-RGS2 and/or RGS3 antibody titer in the immunized subject can be monitored over time by standard techniques, such as with an enzyme linked immunosorbent assay (ELISA) using immobilized RGS2 and/or RGS3. If desired, the antibody molecules directed against RGS2 and/or RGS3 can be isolated from the mammal (e.g., from the blood) and further purified by well-known techniques, such as protein A chromatography to obtain the IgG fraction. At an appropriate time after immunization, i.e., when the anti-RGS2 and/or RGS3 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an RGS2 and/or RGS3 immunogen as described above, and the culture supernatants of the resulting hybridoma cells are screened to identify a hybridoma producing a monoclonal antibody that binds RGS2 and/or RGS3.

Any of the many well-known protocols used for fusing lymphocytes and immortalized cell lines can be applied for the purpose of generating an anti-RGS2 and/or RGS3 monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind RGS2 and/or RGS3, i.e., using a standard ELISA assay.

Additionally, recombinant anti-RGS2 and/or RGS3 polypeptide and/or anti-RGS2 and/or anti-RGS3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988)*J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-RGS2 and/or RGS3 polypeptide and/or anti-RGS2 and/or anti-RGS3 antibody (e.g., monoclonal antibody) can be used to isolate and/or detect (e.g., in diagnostic assays) RGS2 and/or RGS3 polypeptides by standard techniques, such as affinity chromatography or immunoprecipitation. An anti-RGS2 and/or RGS3 polypeptide and/or anti-RGS2 and/or -anti-RGS3 antibody can facilitate the purification of natural RGS2 and/or RGS3 polypeptides from cells and of recombinantly produced RGS2 and/or RGS3 expressed in host cells. Moreover, an anti-RGS2 and/or RGS3 polypeptide antibody can be used to detect RGS2 and/or RGS3 proteins (e.g., in a cellular lysate or cell supernatant) in order to evaluate the abundance and pattern of expression of the RGS2 and/or RGS3 protein. In some embodiments, for example, such antibodies can be used in quantitative immunohistochemical assays to determine RGS2 and/or RGS3 protein levels. Thus, anti-RGS2 and/or RGS3 antibodies can be used to monitor protein levels in a cell or tissue, e.g., cells or tissues having a cardiac-related disorder, as part of a clinical testing procedure, e.g., in order to monitor the efficacy of a therapy. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In vivo techniques for detection of RGS2 and/or RGS3 protein include introducing into a subject a labeled antibody directed against the protein. For example, the antibody can be labeled with a radioactive marker whose presence and location in a subject can be detected by standard imaging techniques.

IV. Identification of Agents that Modulate RGS2 and/or RGS3 Polypeptides

The RGS2 and/or RGS3 nucleic acid and polypeptide molecules described herein can be used to design modulators of one or more of biological activities of the complex or complex polypeptides. In particular, information useful for the design of therapeutic and diagnostic molecules, including, for example, the protein domain, structural information, and the like for polypeptides of the present invention is described herein.

In one aspect, modulators, inhibitors, or antagonists directed against the RGS2 and/or RGS3 polypeptides of the present invention and biological complexes containing them (e.g., cardiac cells expressing RGS2 and/or RGS3 polypeptides) can be used for therapeutic, prognostic, and diagnostic purposes. In certain exemplary embodiments, screening assays for identifying modulators, i.e., candidate or test compounds or agents (e.g., antibodies, peptides, cyclic peptides, peptidomimetics, small molecules, small organic molecules, or other drugs) which have an enhancing effect on RGS2 and/or RGS3 polypeptide expression and/or activity described herein are provided.

Modulators of RGS2 and/or RGS3 polypeptides can be identified and developed as described herein using techniques and methods known to those of skill in the art. The modulators of the invention can be employed, for instance, to inhibit and treat cardiac-related disorders. The modulators of the invention can elicit a change in one or more of the following activities: a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality. A number of methods for identifying a molecule which modulates an RGS2 and/or RGS3 nucleic acid and/or polypeptide are known in the art. For example, in one such method, an RGS2 and/or RGS3 nucleic acid or polypeptide is contacted with a test compound and the activity of the RGS2 and/or RGS3 nucleic acid or polypeptide is determined in the presence of the test compound, wherein a change in the activity of the RGS2 and/or RGS3 nucleic acid and/or polypeptide in the presence of the compound as compared to the activity in the absence of the compound (or in the presence of a control compound) indicates that the test compound modulates the activity of the RGS2 and/or RGS3 nucleic acid and/or polypeptide.

Compounds to be tested for their ability to act as modulators of RGS2 and/or RGS3 nucleic acids or polypeptide, can be produced, for example, by bacteria, yeast or other organisms (e.g. natural products), produced chemically (e.g. small molecules, including peptidomimetics), or produced recombinantly. Compounds for use with the above-described methods can be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In certain embodiments, the compound comprises a biologically active fragment of an RGS2 and/or RGS3 polypeptide (e.g., a dominant negative form that binds to, but does not activate, RGS2 and/or RGS3).

A variety of assay formats will suffice and, in light of the present disclosure, those not expressly described herein can nevertheless be comprehended by one of ordinary skill in the art based on the teachings herein. Assay formats for analyzing the expression and/or activity of an RGS2 and/or RGS3 nucleic acid and/or polypeptide can be generated in many different forms and include assays based on cell-free systems, e.g. purified proteins or cell lysates, as well as cell-based assays which utilize intact cells. Simple binding assays can also be used to detect agents which modulate an RGS2 and/or RGS3 nucleic acid or polypeptide, for example, by enhancing RGS2 and/or RGS3 effects on downstream molecules in a signaling cascade or by enhancing the binding of an RGS2 and/or RGS3 polypeptide to a substrate. Another example of an assay useful for identifying a modulator of an RGS2 and/or RGS3 is a competitive assay that combines one or more RGS2 and/or RGS3 polypeptides with a potential modulator, such as, for example, polypeptides, nucleic acids, natural substrates or ligands, antibodies, or substrate or ligand mimetics, under appropriate conditions for a competitive inhibition assay. RGS2 and/or RGS3 polypeptides can be labeled, such as by radioactivity or a colorimetric compound, such that RGS2 and/or RGS3 complex formation and/or activity can be determined accurately to assess the effectiveness of the potential modulator.

Assays can employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

Assays can also employ any of the methods for isolating, preparing and detecting RGS2 and/or RGS3s polypeptides or complexes, as described above.

Complex formation between an RGS2 and/or RGS3 polypeptide, or fragment thereof, and a binding partner (e.g., G alpha subunits or heterotrimers) can be detected by a variety of methods. Modulation of the complex's formation can be quantified using, for example, detectably labeled proteins such as radiolabeled, fluorescently labeled, or enzymatically labeled polypeptides or binding partners, by immunoassay, or by chromatographic detection.

In certain embodiments, it can be desirable to immobilize an RGS2 and/or RGS3 polypeptide to facilitate separation of RGS2 and/or RGS3 complexes from uncomplexed RGS2 and/or RGS3d polypeptides, as well as to accommodate automation of the assay. In any case, binding of an RGS2 and/or RGS3 polypeptide to a binding partner can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/polypeptide (GST/polypeptide) fusion proteins can be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions can be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of RGS2 and/or RGS3 polypeptides found in the bead fraction quantified from the gel using standard electrophoretic techniques such as described in the appended examples.

Other techniques for immobilizing proteins on matrices are also available for use in the subject assay. For instance, an RGS2 and/or RGS3 polypeptide can be immobilized utilizing conjugation of biotin and streptavidin. For instance, biotinylated polypeptide molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide can be derivatized to the wells of the plate, and polypeptide trapped in the wells by antibody conjugation. As above, preparations of a binding partner and a test compound are incubated in the polypeptide presenting wells of the plate, and the amount of complex trapped in the well can be quantified. Exemplary methods for detecting such complexes, in addition to those described above for the GST-immobilized complexes, include immunodetection of complexes using antibodies reactive with the binding partner, or which are reactive with the RGS2 and/or RGS3 polypeptide and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the binding partner.

Antibodies against the RGS2 and/or RGS3 polypeptide can be used for immunodetection purposes. Alternatively, the RGS2 and/or RGS3 polypeptide to be detected can be "epitope-tagged" in the form of a fusion protein that includes, in addition to the polypeptide sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system can be derived to favor discovery of modulators of particular intermediate states of the protein-protein interaction. For instance, a reconstituted protein assay can be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, can be accomplished in any vessel suitable for containing the reactants. Examples include microtitre plates, test tubes, and micro-centrifuge tubes.

In still further embodiments, the RGS2 and/or RGS3 polypeptide can be generated in whole cells, taking advantage of cell culture techniques to support the subject assay. For example, the RGS2 and/or RGS3 polypeptide, can be constituted in a prokaryotic or eukaryotic cell culture system. This allows for an environment more closely approximating that which therapeutic use of the modulator would require, including the ability of the agent to gain entry into the cell. Furthermore, certain of the in vivo embodiments of the assay are amenable to high through-put analysis of candidate agents.

Some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high throughput analysis in that proliferation of the cell can provide a simple measure of the protein-protein interaction.

The amount of transcription from the reporter gene can be measured using any method known to those of skill in the art to be suitable. For example, specific mRNA expression can be detected using Northern blots or specific protein product can be identified by a characteristic stain, western blots or an intrinsic activity. In certain embodiments, the product of the reporter gene is detected by an intrinsic activity associated with that product. For instance, the reporter gene can encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as can be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as can be manifest in an alteration of binding affinity with other proteins or changes in enzymatic properties of the molecular target. Accordingly, potential modulators of RGS2 and/or RGS3 can be detected in a cell-free assay generated by constitution of a functional RGS2 and/or RGS3 polypeptide in a cell lysate. In an alternate format, the assay can be derived as a reconstituted protein mixture which, as described below, offers a number of benefits over lysate-based assays.

The activity of an RGS2 and/or RGS3 polypeptide can be identified and/or assayed using a variety of methods well known to the skilled artisan. For example, the activity of an RGS2 and/or RGS3 nucleic acid and/or polypeptide can be determined by assaying for the level of expression of RNA and/or protein molecules. Transcription levels can be determined, for example, using Northern blots, hybridization to an oligonucleotide array or by assaying for the level of a resulting protein product. Translation levels can be determined, for example, using Western blotting or by identifying a detectable signal produced by a protein product (e.g., fluorescence, luminescence, enzymatic activity, etc.). Depending on the particular situation, it can be desirable to detect the level of transcription and/or translation of a single gene or of multiple genes. Similarly, it can be desirable to determine the status of stability-enhancing modifications made to the RGS2 and/or RGS3 polypeptides of the present invention (e.g., analyzing the production of disulfide bonds in Cys-Cys modifications and the like).

In other embodiments, the biological activity of an RGS2 and/or RGS3 nucleic acid and/or polypeptide can be assessed by monitoring changes in the phenotype of a targeted cell. For example, the detection means can include a reporter gene construct which includes a transcriptional regulatory element that is dependent in some form on the level and/or activity of an RGS2 and/or RGS3 nucleic acid and/or polypeptide. The RGS2 and/or RGS3 nucleic acid and/or polypeptide can be provided as a fusion protein with a domain that binds to a DNA element of a reporter gene construct. The added domain of the fusion protein can be one which, through its DNA binding ability, increases or decreases transcription of the reporter gene. Whichever the case can be, its presence in the fusion protein renders it responsive to an RGS2 and/or RGS3 nucleic acid and/or polypeptide. Accordingly, the level of expression of the reporter gene will vary with the level of expression of an RGS2 and/or RGS3 nucleic acid and/or polypeptide.

Moreover, in the whole cell embodiments of the subject assay, the reporter gene construct can provide, upon expression, a selectable marker. A reporter gene includes any gene that expresses a detectable gene product, which can be RNA or protein. Preferred reporter genes are those that are readily detectable. The reporter gene can also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of an RGS2 and/or RGS3 nucleic acid and/or polypeptide present in the cell. Such embodiments of the subject assay are particularly amenable to high through-put analysis in that proliferation of the cell can provide a simple measure of inhibition of the RGS2 and/or RGS3 nucleic acid and/or polypeptide.

Identification of agents that modulate RGS2 and/or RGS3 expression and/or activity (e.g., increase activity) that would have therapeutic benefits for subjects having a cardiac-related disorder may be accomplished using isolated cells or isolated tissues. For instance, test agents can be administered to isolated cells, preferably cardiomyocytes, from mammals or other organisms and the effects can be determined by measuring criteria described herein, such as the percent shortening of the cell (% FS); the rates of shortening or re-lengthening (+/−dL/dt), by standard techniques (Chaudhri et al. (2002) *Am. J. Physiol. Heart Circ. Physiol.* 283:H2450-H2457). Alternatively, muscle(s), preferably of cardiac origin, can be isolated and measurements of contractile function assess in the presence and absence of the test agents, by standard techniques (Slack et al. (1997) *J. Biol. Chem.* 272:18862-18868). The desired agents can also be identified by measuring such indicators as acute hemodynamics, including heart rate, blood pressure, rates of contraction and relaxation (+dP/dt, and −dP/dt), left ventricular pressure and derivations of these parameters. Suitable, normal animals including, but not limited to, various genetic strains of mice, rats, guinea pigs, hamsters, humans, rabbits, dogs, pigs, goats, cows, monkeys, chimpanzees, sheep, hamsters and zebrafish can be used. In addition, desired agents can be identified by the methods described herein in suitable, animal models of heart failure or other cardiac-related disorders including, but not limited to, various genetic strains of transgenic or knockout mice, such as the MLP$^{(-/-)}$ KO mice, type-1 serine/threonine phosphatase overexpressing mice (PP1c), and RGS2 and/or RGS3 overexpressing transgenic mice. In addition, desired agents can be identified in spontaneous or natural models of heart failure and cardiac dysfunction due to a genetic or multiple genetic defects, including but not limited to the spontaneous hypertensive heart failure rat or the Dahl salt sensitive rat. In addition, desired agents can be identified in surgically induced models of cardiac dysfunction including, but not limited to, synchrony/asynchrony pacing models, myocardial infarction models, coronary microembolism model, aortic constriction model, arteriovenous fistula model or other pressure or volume overload models in rats, guinea pigs, rabbits, dogs, pigs, goats, cows, monkeys, chimpanzees, sheep, hamsters and zebrafish.

V. Methods of the Invention a. Methods of Administration

In one aspect, the present invention provides compositions useful in administrable forms to subjects (e.g., polypeptides, nucleic acids, vectors, host cells, and the like described herein). Such immunogens can be administered in any of a number of routes known in the art (e.g., to be compatible with eliciting strong antibody responses). Administration can be by injection, infusion, aerosol, oral, transdermal, transmucosal, intrapleural, intrathecal, or other suitable routes. Preferably, the composition is administered by intravenous, subcutaneous, intradermal, or intramuscular routes, or any combination thereof.

Representative forms of administrable nucleic acids include a "naked" DNA plasmid, a "naked" RNA molecule, a DNA molecule packaged into a replicating or nonreplicating viral vector, an RNA molecule packaged into a replicating or nonreplicating viral vector, a DNA molecule packaged into a bacterial vector, or combinations thereof.

In one embodiment, recombinant RGS2 and/or RGS3 polypeptides can be administered to subjects. In some embodiments, fusion proteins can be constructed and administered which have enhanced biological properties. In addition, the polypeptides can be modified according to well-known pharmacological methods in the art (e.g., pegylation, glycosylation, oligomerization, etc.) in order to further enhance desirable biological activities, such as increased immunogenicity, bioavailability, and/or decreased proteolytic degradation.

For embodiments using instant nucleic acid delivery, any means for the introduction of a polynucleotide into a subject, such as a human or non-human mammal, or cells thereof can be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs can first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, can then be effected using known methods and materials and delivered to the recipient mammal. See, e.g., Canonico et al., Am J Respir Cell Mol Biol 10:24-29, 1994; Tsan et al., Am J Physiol 268; Alton et al., Nat Genet. 5:135-142, 1993; and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest can be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter can be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences, such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos.

4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777, 127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued Can 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth, Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxvirus, an arena virus, a vaccinia virus, a polio virus, and the like. They offer several attractive features for various mammalian cells (Friedmann (1989) Science, 244:1275-1281; Ridgeway, 1988, supra; Baichwal and Sugdcn, 1986, supra; Coupar et al., 1988; Horwich et al. (1990) J. Virol., 64:642-650).

For some methods, local administration into cardiac tissue may be desired and methods are known in the art for achieving such local administration. For example, a composition can be injected into an affected vessel (e.g., an artery) or an organ (e.g., the heart). In one method of treatment embodiment, flow of blood through coronary vessels of a heart is restricted and a viral delivery system is introduced into the lumen of a coronary artery. In one embodiment, the heart is permitted to pump while coronary vein outflow is restricted. In another embodiment, a viral delivery system is used and injected into the heart while restricting aortic flow of blood out of the heart, thereby allowing the viral delivery system to flow in to and be delivered to the heart. In other embodiments, the flow of blood through the coronary vessels is completely restricted, and in specific such embodiments, the restricted coronary vessels comprise: the left anterior descending artery (LAD, the distal circumflex artery (LCX), the great coronary vein (GCV), the middle cardiac vein (MCV), or the anterior interventricular vein (AIV). In certain embodiments, the introduction of the viral delivery system occurs after ischemic preconditioning of the coronary vessels. In another embodiment, the composition is injected into the heart by a method comprising the steps of restricting aortic flow of blood out of the heart, such that blood flow is re-directed to coronary arteries; injecting the vector into lumen of the heart, aorta or coronary ostia such that the vector flows into the coronary arteries; permitting the heart to pump while the aortic flow of blood out of the heart is restricted; and reestablishing the aortic flow of blood. In still another embodiment, a composition is injected into the heart with a catheter. In yet another embodiment, a composition is directly injected into a muscle of the heart.

b. Methods of Evaluating Cardiac-Related Responses

In some aspects, the present invention requires the analysis of cardiac-related responses. Without limitation, a representative list of cardiac-related responses to be analyzed include one or more of a) increased heart chamber mechanical efficiency; b) increased β-adrenergic receptor numbers and/or density; c) inhibited $G\alpha_i$ signaling; d) increased $G\alpha_s$-biased B2-adrenergic signaling; e) increased adenosine cyclic adenosine monophosphate amounts and/or responsiveness; f) increased sarcoplasmic reticulum-localized protein kinase A; g) increased sarcomeric shortening; h) decreased sarcomeric relengthening velocity; i) increased peak calcium transients; j) increased calcium decline rate; k) increased maximal calcium activated myofilament force; l) decreased $EC_{50}$ for calcium-mediated myofilament force activation; m) increased Hill coefficient; n) increased phosphorylation of myofilament proteins; and b) lowered mortality.

Other cardiac-related responses are described herein and are also contemplated as being related to RGS2 and/or RGS3 activity. For example, one or more of the following cardiac-related phenotypes can be analyzed: hypertrophy; morphology, such as interventricular septal hypertrophy; left ventricular-end systolic maximum dP/dt or end-diastolic dimension( ); papillary muscle dimension; left-ventricular outflow tract obstruction; midventricular hypertrophy; apical hypertrophy; asymmetrical hypertrophy; concentric enlarged ventricular mass; eccentric enlarged ventricular mass; sarcomere structure; myofibril function; receptor expression; heart rate; ventricular systolic pressure; ventricular diastolic pressure; aortic systolic pressure; aortic diastolic pressure; contractility; interstitial fibrosis; cardiomyocyte disarray; $Ca^{2+}$ sensitivity; $Ca^{2+}$ release; $Ca^{2+}$ uptake; catecholine sensitivity; α-adrenergic sensitivity; β-adrenergic sensitivity; dobutamine sensitivity; thyroxine sensitivity; angiotensin-converting enzyme inhibitor sensitivity; amiodarone sensitivity; lidocaine sensitivity; glycoprotein receptor antagonist sensitivity; anabolic steroid sensitivity; carnitine transport irregularities; left ventricular dilation, reduced left ventricular ejection fraction; left atrial dilatation; diuretic sensitivity; volemia; ischemia; leukocyte flow properties; the polymorphonuclear leukocyte (PMN) membrane fluidity; PMN cytosolic $Ca^{2+}$ content; high interventricular septal defects, rosette inhibition effect; contractile force transmission; myocardial fiber disarray; increased chamber stiffness; impaired relaxation; small-vessel disease; dyspnea; angina; presyncope; tachycardia; syncope; lethargy; respiratory distress; ruffled fur; hunched posture; peripheral edema; ascites; hepatomegaly; edematous lung; cardiomegaly; organized thrombi formation; heart weight/body weight ratio; rate of pressure development, rate of pressure fail, cell twitch measurement and the like. See, for example, Braunwald et al. (2002) Circ. 106:1312-1316; Wigle et al. (1995) Circ. 92:1680-1692; and Pi and Walker (2000) Am. J. Physiol. Heart Circ. Physiol. 279:H26-H34; hereby incorporated by reference in their entirety.

Methods for measuring such cardiomyopathic phenotypes are described herein and are well-known in the art. Exemplary methods include, but are not limited to, trans-thoracic echocardiography, transesophageal echocardiography, exercise tests, urine/catecholamine analysis, EIAs, light microscopy, heart catheterization, dynamic electrocardiography, Langendorff hanging heart preparation, working heart preparation, MRI, multiplex RT-PCR, positron emission tomography, angiography, magnetic resonance spin echo, short-axis MRI scanning, Doppler velocity recordings, Doppler color flow imaging, stress thallium studies, cardiac ultrasound, chest X-ray, oxygen consumption test, electrophysiological studies, auscultation, scanning EM, gravimetric analysis, hematoxylin and eosin staining, skinned fiber analysis, transmission electron microscopy, immunofluorescent analysis, trichrome staining, Masson's trichrome staining, Von Kossa staining, 2-D echocardiography, cardiotocography, baseline M-mode echocardiography, and myocardial lactate production assays. See, for example, Braz et al. (2002) *J. Cell. Biol.* 156:905-919; Braunwald et al. (2002) *Circ.* 106:1312-1316; Sohal et al. (2001) *Circ. Res.* 89:20-25; Nagueh et al. (2000) *Circ.* 102:1346-1350; Sanbe et al. (2001) *J. Biol. Chem.* 276:32682-32686; Sanbe et al. (1999) *J. Biol. Chem.* 274:21085-21094; Wigle et al. (1995) *Circ.* 92:1680-1692; Pi and Walker (2000) *Am. J. Physiol. Heart Circ. Physiol.* 279:H26-H34; and Wang et al. (2001) *Am. J. Physiol. Heart Circ. Physiol.* 269:H90-H98 hereby incorporated by reference in their entirety.

For example, cardiac contractility can be analyzed. Assays to determine cardiac contractility are known in the art and include, but are not limited to, shortening assays, peak shortening, time to peak, time to ½ maximal relaxation, contracting and relaxing rate assays, changes in cardiac chronotropy, changes in cardiac lusitropy, and gross heart contraction assays. Altered cardiac-preferred expression of RGS2 and/or RGS3, for example, can result in altered (e.g., acutely increased) cardiac contractility. An acute modulation or alteration can begin within 1 second; 10 seconds; 30 seconds; 1, 2, 3, 4, 5, 6, 7, 8, 9, 10, 11, 12, 13, 14, 15, 20, 25, 30, 35, 40, 45, 50, 55, 60 minutes; 2, 3, 4, 5, 6, 7, 8, 9, 10, 11, 12, 13, 14, 15, 16, 17, 18, 19, 20, 21, 22, 23, 24 hours; 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days after administration of the RGS2 and/or RGS3 modulating agent. The duration of the modulation ranges from short durations such as, but not limited to, nanosecond, second, and minute increments; intermediate durations such as, but not limited to, hour, day, and week increments; to long durations such as, but not limited to, month and year increments, up to and including the recipient's lifespan.

In methods examining progression of cardiac-related disorders, additional criteria for evaluation can include, but are not limited to, β-receptor number, β-receptor coupling, adenylyl cyclase activity, cAMP levels at rest, cAMP levels after forskolin administration, PKA activity, PKA protein levels, L-type calcium channel current density, SERCA2a protein levels, and phospholamban mRNA levels, or phospholamban phosphorylation of proteins.

c. Diagnostic, Prognostic and Therapeutic Methods

In one aspect, the present invention provides a method of assessing whether a subject is afflicted with a cardiac-related disorder or at risk for developing a cardiac-related disorder, the method comprising comparing a) the amount, structure, and/or activity of a marker in a subject sample, wherein the marker is RGS2 and/or RGS3; and b) the normal amount, structure, and/or activity of the marker, wherein a significant difference between the amount, structure, and/or activity of the marker in the sample and the normal amount, structure, and/or activity is an indication that the subject is afflicted with the cardiac-related disorder or at risk for developing the cardiac-related disorder.

In another aspect, the present invention provides a method for monitoring the progression of a cardiac-related disorder in a subject, the method comprising a) detecting in a subject sample at a first point in time, the amount and/or activity of a marker, wherein the marker is RGS2 or RG3; b) repeating step a) at a subsequent point in time; and c) comparing the amount and/or activity detected in steps a) and b), and therefrom monitoring the progression of the cardiac-related disorder in the subject.

In still another aspect, the present invention provides a method of treating a subject afflicted with a cardiac-related disorder comprising administering to the subject an agent that modulates the amount and/or activity of a gene or protein corresponding to RGS2 and/or RGS3, thereby treating the subject afflicted with the cardiac-related disorder.

It will be appreciated that individual dosages can be varied depending upon the requirements of the subject in the judgment of the attending clinician, the severity of the condition being treated and the particular compound being employed. In determining the therapeutically effective amount or dose, a number of additional factors can be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage can be divided and administered in portions during the day if desired.

The duration and/or dose of treatment with therapies can vary according to the particular agent or combination thereof. An appropriate treatment time for a particular therapeutic agent will be appreciated by the skilled artisan. The invention contemplates the continued assessment of optimal treatment schedules for each therapeutic agent, where the phenotype of the cardiac-related disorder of the subject as determined by the methods of the invention is a factor in determining optimal treatment doses and schedules.

In general, it is preferable to obtain a first sample from the subject prior to beginning therapy and one or more samples during treatment. In such a use, a baseline of expression of cells from subjects with a cardiac-related disorder prior to therapy is determined and then changes in the baseline state of expression of cells from subjects with a cardiac-related disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with a cardiac-related disorder is increasing or decreasing.

It may further be advantageous to administer the regimens described herein with other agents, such as proteins, peptides, antibodies, and the like to treat the cardiac-related disorder and/or ameliorate its symptoms. For example, inhibitors of the rennin-angiotensin system and/or β-adrenergic blocking agents can be used. Therapeutic agents to treat pathologic hypertrophy in the setting of heart failure include angiotensin II converting enzyme (ACE) inhibitors and β-adrenergic receptor blocking agents. Other pharmaceutical agents that have been disclosed for treatment of cardiac hypertrophy include angiotensin II receptor antagonists (U.S. Pat. No. 5,604,251) and neuropeptide Y antagonists (WO 98/33791). Non-pharmacological treatment is primarily used as an adjunct to pharmacological treatment. One means of non-pharmacological treatment involves reducing the sodium in the diet. In addition, non-pharmacological treatment can include the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

Non-limiting examples of a pharmacological therapeutic agent that may be used in the present invention include an antihyperlipoproteinemic agent (e.g., an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof), an antiarteriosclerotic agent (e.g., pyridinol carbamate), an antithrombotic/fibrinolytic agent (e.g., anticoagulants, anticoagulant antagonists, antiplatelet agents, thrombolytic agents, thrombolytic agent antagonists or combinations thereof), a blood coagulant (e.g., thrombolytic agent antagonists and anticoagulant antagonists), an antiarrhythmic agent (e.g., Class I antiarrhythmic agents (sodium channel blockers), Class II antiarrhythmic agents (β-adrenergic blockers), Class II antiarrhythmic agents (repolarization prolonging drugs), Class TV antiarrhythmic agents (calcium channel blockers) and miscellaneous antiarrythmic agents), an antihypertensive agent (e.g., sympatholytic, alpha/beta blockers, alpha blockers, anti-angiotensin II agents, beta blockers, calcium channel blockers, vasodilators and miscellaneous antihypertensives), a vasopressor (e.g., amezinium methyl sulfate, angiotensin amide, dimetofrine, dopamine, etifelmin, etilefrin, gepefrine, metaraminol, midodrine, norepinephrine, pholedrine and synephrine), a treatment agent for congestive heart failure (e.g., anti-angiotensin II agents, afterload-preload reduction treatment, diuretics and inotropic agents, an antianginal agent, an antibacterial agent or a combination thereof.

Non-limiting examples of a surgical therapeutic agent that may be used in the present invention include preventive, diagnostic or staging, curative, and palliative surgery. Surgery, and in particular, a curative surgery, may be used in conjunction with other therapies, such as the present invention and one or more other agents. Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

VI. Pharmaceutical Compositions

In another aspect, the present invention provides pharmaceutically acceptable compositions which comprise a therapeutically-effective amount of a composition described herein, formulated together with one or more pharmaceutically acceptable carriers (additives) and/or diluents and with or without additional antiviral agents and/or immunogens. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) RGS2 and/or RGS3 expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valcrate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) RGS2 and/or RGS3 expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) RGS2 and/or RGS3 expression and/or activity, with the carrier and, optionally, one or more accessory ingredients. In general, the formulations are prepared by uniformly and intimately bringing into association an agent with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. A compound can also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered peptide or peptidomimetic moistened with an inert liquid diluent.

Tablets, and other solid dosage forms, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration can be presented as a suppository, which can be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) RGS2 and/or RGS3 expression and/or activity include powders, sprays, ointments, pastes, creams, lotions, gels, solutions, patches and inhalants. The active component can be mixed under sterile conditions with a pharmaceutically-acceptable carrier, and with any preservatives, buffers, or propellants which can be required.

The ointments, pastes, creams and gels can contain, in addition to an agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) RGS2 and/or RGS3 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) RGS2 and/or RGS3 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) RGS2 and/or RGS3 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Actual dosage levels of the active ingredients in the pharmaceutical compositions of this invention can be determined by the methods of the present invention so as to obtain an amount of the active ingredient, which is effective to achieve the desired therapeutic response for a particular subject, composition, and mode of administration, without being toxic to the subject.

Nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1: Materials and Methods for Examples 2-8

A. HF Models

Five rapid-pacing models of HF were studied. Dyssynchronous HF ($HF_{dys}$, n=16) dogs were first subjected to left bundle radio-frequency ablation followed by 6 weeks of atrial tachypacing (200 $min^{-1}$). Always synchronous HF ($HF_{syn}$, n=13) also underwent atrial tachypacing, but without previous LBB ablation. Two models of CRT were studied. One started as $HF_{dys}$ for 3 weeks, then switched to 3-week biventricular tachypacing (LV lateral and RV anteroapical epicardium) (CRT, n=14). The other started with RV tachypacing for 3 weeks to induce dyssynchronous HF, then switched to atrial pacing (V3A3, n=11) for 3 weeks. A fifth group was exposed to atrial, RV, then atrial tachypacing (each 2 weeks, AVA, n=5). Last, healthy normal controls were studied (n=17). Controls±sham surgery behave identically (Chakir et al. (2009) Circulation. 119:1231-1240). Echocardiography and tissue Doppler (longitudinal strain speckle tracking with four-chamber views) were performed at 3 and 6 weeks to assess dyssynchrony (variance of peak systolic strain timing) as described in Chakir et al. (2009) Circulation. 119:1231-1240. At terminal study, dogs were anesthetized with pentobarbital, pacing was suspended, and a micromanometer (Millar Instruments Inc.) was advanced to record LV pressure. The chest was opened and hearts were rapidly harvested under cold cardioplegia, with the myocardiumfrozen for tissue analysis or prepared for myocyte isolation (Chakir et al. (2009) Circulation. 119:1231-1240).

B. Myocyte Function Studies

Myocyte sarcomere shortening and whole-cell calcium transients were assessed with an inverted microscope (Ellipse TE2001, Nikon) equipped with an image-fluorescence system (MyoCam, IonOptix). Myocyte function studies were performed at 37° C. and paced by field stimulation at 1 Hz, as described in Chakir et al. (2009) Circulation. 119:1231-1240.

C. Protein and Gene Expression

Myocardium was homogenized in lysis buffer (Cell Signaling Technology) and 50 to 100 mg were loaded for gel electrophoresis with standard methods. $G_i(1,2,3)$, $G_s$, RGS2, RGS3, RGS4, GRK2, and β-ARrestin1/2 (Santa Cruz Biotechnology; each at 1:400) and glyceraldehyde-3-phosphate dehydrogenase (GAPDH) (Imgenex; 1:10,000) were probed. Gene expression was assessed by real-time polymerase chain reaction (PCR) with the SYBR Green PCR master mix (Applied Biosystems) and ABI Prism 7900.

D. Radioligand Binding Assay

β-AR radioligand binding studies were performed using myocardial membrane fractions with the nonselective β-AR antagonist [$^{125}$I]-labeled cyanopindolol, as described in Zhou et al. (2000) Mol. Pharmacol. 58:887-894.

E. Myocyte Culture and Adenoviral Infection

Isolated myocytes were washed three times with minimum essential medium (MEM) containing 1.2 mM $Ca^{2+}$, 2.5% fetal bovine serum (FBS), and 1% penicillin-streptomycin, and then plated with the same medium in culture dishes precoated with mouse laminin (10 mg/ml) (Sigma). Adenovirus-mediated gene transfer of GFP, RGS2, or RGS3 was implemented by adding a minimal volume of the FBS-free MEM containing the gene-carrying adenovirus (100 multiplicities of infection). The full volume of FBS-free MEM was supplied after culture for another 1 to 2 hours. RGS expression and myocyte functional changes were assessed at 24 hours after transfection.

F. Fluorescence Energy Resonance Transfer Studies

Adult myocytes were infected with an adenovirus expressing either the modified EPAC-based cAMP FRET sensor (ICUE3) (DiPilato et al. (1999) J Biol Chem. 274:22048-22052) or SR-localized PKA activity sensor SR-AKAR3 (Liu et al. (2011) Biochem Biophys Res Commun. 404:581-586). Just before study, cells were washed two times with Hanks' balanced salt solution and imaged at room temperature in the dark. Dual-emission ratio imaging used a 420DF20 excitation filter, a 450DRLP dichroic mirror, and two emission filters (475DF40 for cyan fluorescent protein and 535DF25 for yellow fluorescent protein) and was performed on a Zeiss Axiovert 200 M microscope with a MicroMAX BFT512 cooled charge-coupled device camera (Roper Scientific) controlled by MetaFluor 6.2 software (Universal Imaging). Fluorescent images (taken every 20 to 30 s) were background-corrected by subtracting autofluorescence intensities of untransfected cells (or background with no cells) from the emission intensities of cells expressing reporters.

G. Human Myocardial Samples

The catheterization procedures, biopsy protocol, and RNA analysis from human LV myocardial samples have been previously reported in Vanderheyden et al. (2008) J Am Coll Cardiol. 51:129-136.

H. Statistical Analysis

Comparisons between multiple experimental groups (no repeated measures) were performed by one-way analysis of variance (ANOVA) with a Tukey multiple-comparison test. In vivo data from the same heart at multiple time points were analyzed by repeated-measures ANOVA. Data are presented as means±SEM.

Example 2: Effect of Synchronous, Dyssynchronous, or Resynchronized HF on Regional Wall Motion and Chamber Function To identify differences in β-adrenergic signaling between synchronous, dyssynchronous, and resynchronized HF, several variants of the tachypacing-induced HF canine model was used (Chakir et al. (2009) Circulation. 119:1231-1240). FIG. 1A displays examples of regional shortening (strains) determined by speckle tracking imaging for both anterior/septal and lateral walls in each model. Strains were synchronous in normal controls, whereas $HF_{dys}$ had marked discoordination that was restored by CRT (biventricular pacing). Dyssynchrony was also generated by right ventricular (RV) free wall pacing and then resynchronized by reverting to atrial pacing (V3A3; FIG. 1A, lower left/middle). $HF_{syn}$ (atrial pacing) had coordinated contraction throughout. Strain magnitude fell ~40% in all models from control levels (y-axis scales adjusted), indicating cardiac depression. Although dyssynchrony/synchrony history differed among models, all developed similar global systolic and diastolic dysfunction (FIG. 2), because all were tachy-paced for 6 weeks, and this had a dominant effect on the integrated hemodynamic response. Thus, molecular/cellular differences between the models reflected the specifics of synchronization history rather than systemic depression.

Figure 1C:
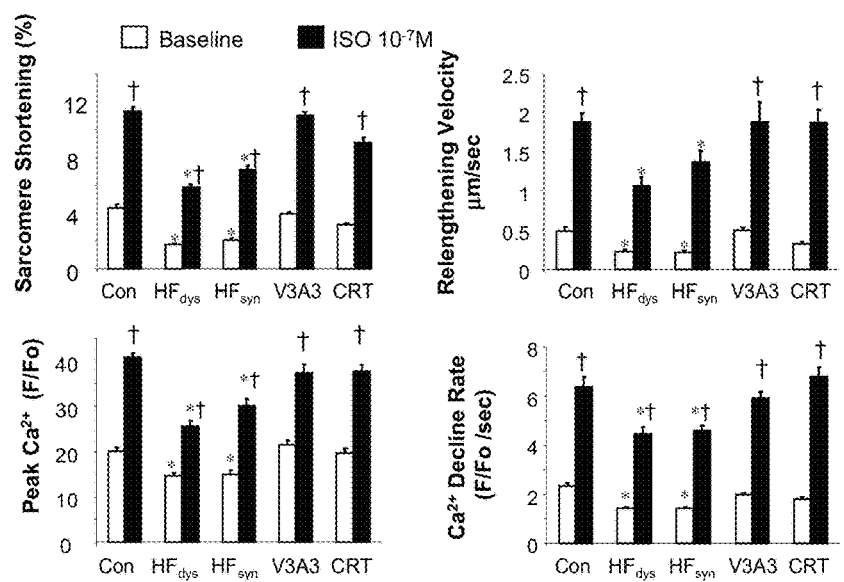
Figure 2:
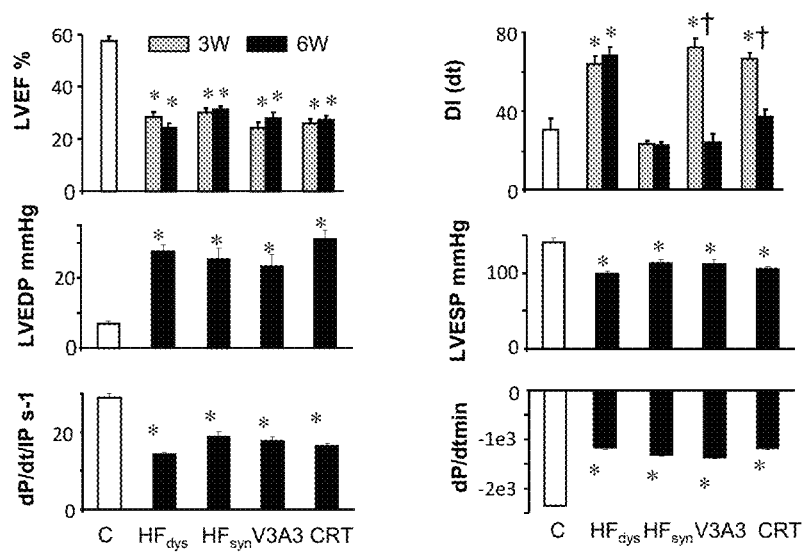
FIG. 2 shows the results of global ventricular function in five experimental models. The dyssynchrony index (DI) shows the differences between the always dyssynchronous, always synchronous, and 2 resynchronized models. A value of ~30 is typical of the normal heart. LV ejection fraction (LVEF) at 3 and 6 week time points is depressed compared to normal hearts with very modest differences among models that do not reach statistical significance in a 1-way ANOVA. Similarly, LV end-diastolic pressure (LVEDP), end-systolic pressure (LVESP), contractile function (dP/dtmax/IP) and relaxation (dP/dtmin) are abnormal in each HF model compared to control with no major differences among the models. * represents p<0.01 versus control and † represents p<0.001 versus 6-wk data.

Example 3: Effect of Resynchronization on Basal and Isoproterenol-Stimulated Function and $Ca^{2+}$ The acute impact of β-adrenergic receptor (β-AR) stimulation on myocyte dynamics and whole-cell $Ca^{2+}$ transients was determined in cells freshly isolated from each model. Rest and β-AR-stimulated (isoproterenol) sarcomere shortening and relengthening, and peak $Ca^{2+}$ transient and decay rate, were markedly and similarly depressed in myocytes from always dyssynchronous or synchronous HF. Both features returned to control levels in the resynchronization models (FIGS. 1B and 1C). Thus, enhanced β-AR responsiveness did not reflect the presence of contractile synchrony, but rather a history of dyssynchrony that was subsequently ameliorated.

Figure 3A:
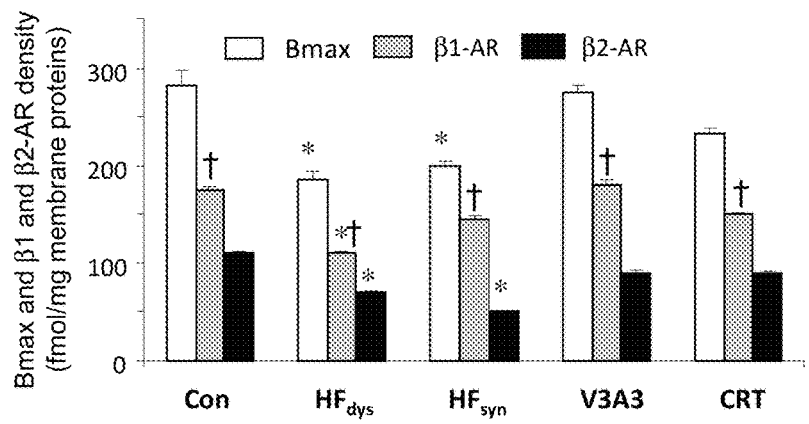
FIGS. 3A-3C show that resynchronization enhances β-receptor density and shifts signaling away from $G\alpha_i$ coupling to generate a $G\alpha_s$-biased response.
Figure 3B:
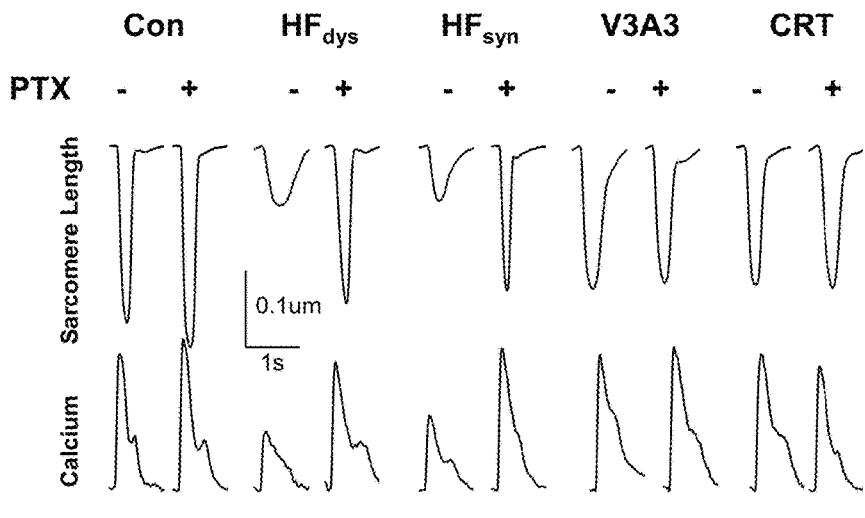
Figure 3C:
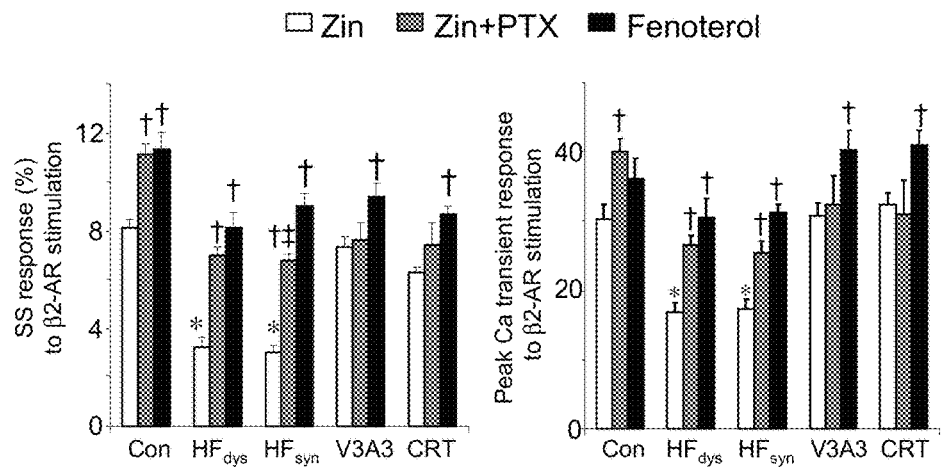
Figure 4A:
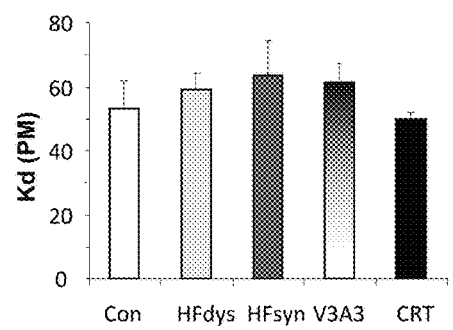
FIGS. 4A-4B show β-receptor binding affinity for normal control and four HF models.
Figure 4B:
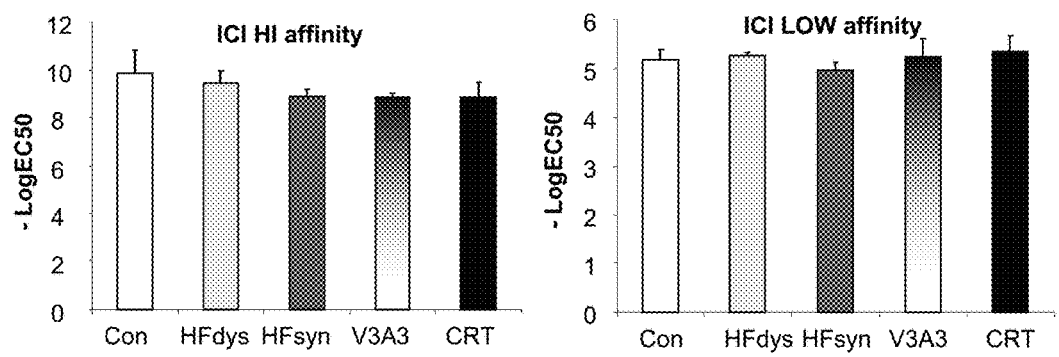
Figure 5A:
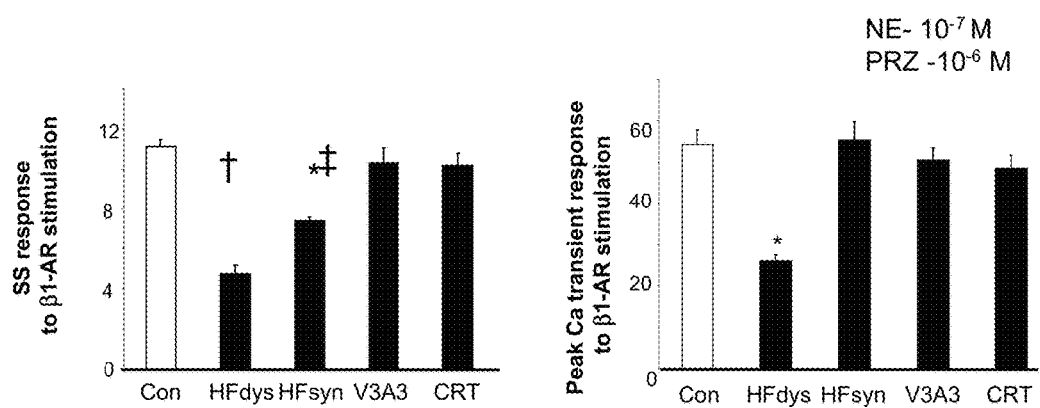
FIGS. 5A-5B show analyses of $\beta_1$-AR and $\beta_2$-AR.
Figure 5B:
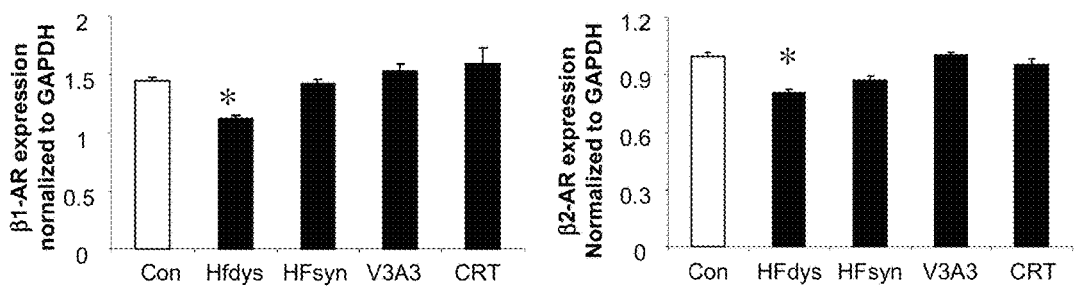

Example 4: Effect of Resynchronization on β-AR Density and $β_2$-AR $G_i$ Coupling Differential β-AR signaling was in part due to a decline in combined $β_1$ and $β_2$ subtype receptor density in $HF_{dys}$ and $HF_{syn}$ that was ameliorated by resynchronization (FIG. 3A). Receptor affinity (both subtypes) was unaltered in all models (FIG. 4). $β_1$ gene expression declined in $HF_{dys}$, and myocyte response to selective $β_1$ stimulation was depressed in this model and less so in $HF_{syn}$ (FIG. 5). Because both $HF_{dys}$ and $HF_{syn}$ had similar depressed responses to isoproterenol, it was hypothesized that differential $β_2$-AR regulation may play a more prominent role in the depressed response to β-AR signaling in $HF_{dys}$ and to its restoration with resynchronization. $β_2$-AR signaling coactivates both stimulatory and inhibitory G proteins (heterotrimeric guanine nucleotide-binding proteins). To better understand this signaling, cells were stimulated with the $β_2$-selective agonist zinterol (1 mM) with or without the $Gα_i$ inhibitor pertussis toxin (PTX; FIGS. 3B and 3C). PTX augmented zinterol-stimulated shortening and $Ca^{2+}$ transients slightly in controls, but greatly amplified the response in cells from $HF_{dys}$ and $HF_{syn}$. In contrast, cells from resynchronized hearts had enhanced responses to zinterol that were little changed after PTX, indicating that the $β_2$-AR in these hearts was already biased toward $Gα_s$-coupled signaling. To further test this, cells were treated with the R,R-enantiomer of fenoterol, a biased $β_2$ agonist that does not activate $Gα_i$ protein (Woo et al. (2009) *Mol Pharmacol.* 75:158-165). As shown in FIG. 3C, all HF models now had similar responses to fenoterol, with somewhat higher $Ca^{2+}$ transients in CRT/V3A3 groups. This was similar to zinterol+PTX responses in all groups and augmented over zinterol alone in $HF_{dys}$ and $HF_{syn}$. Fenoterol and zinterol responses were similar in the resynchronization models. These data show that a history of dyssynchrony followed by resynchronization uniquely generates a $Gα_s$-biased $β_2$-AR.

Figure 6A:
FIGS. 6A-6F show that resynchronization enhances myocyte cAMP levels and PKA activation in the SR in response to $\beta_2$ stimulation.
Figure 6B:
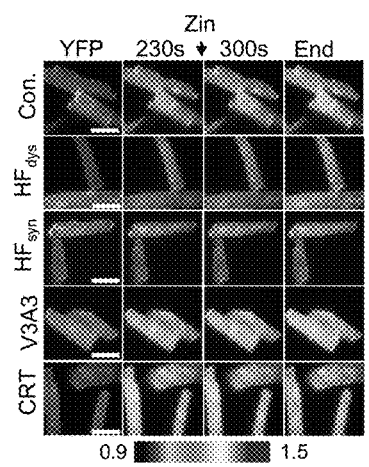
Figure 6C:
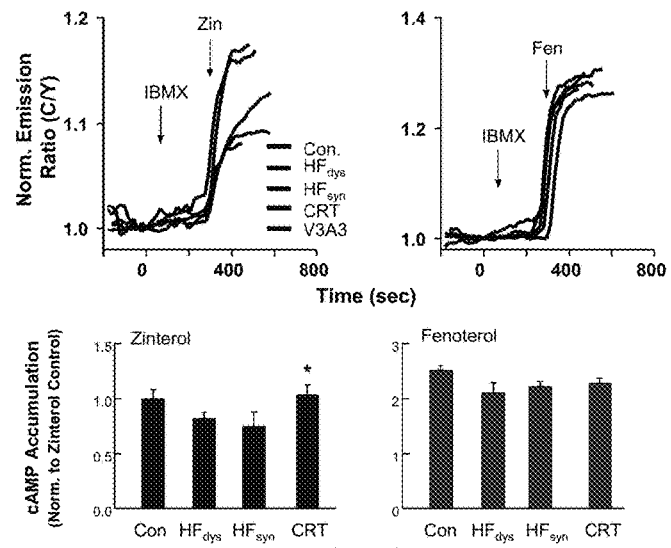
Figure 6D:
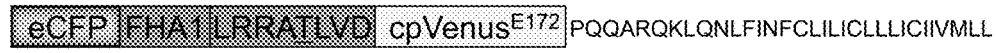
Figure 6E:
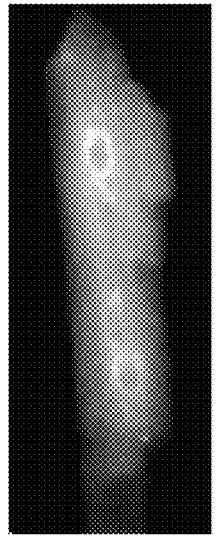
Figure 6F:
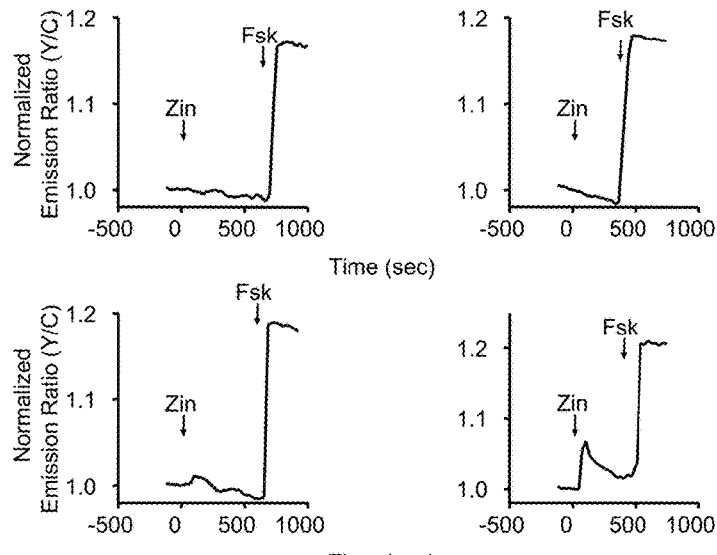
Figure 7:
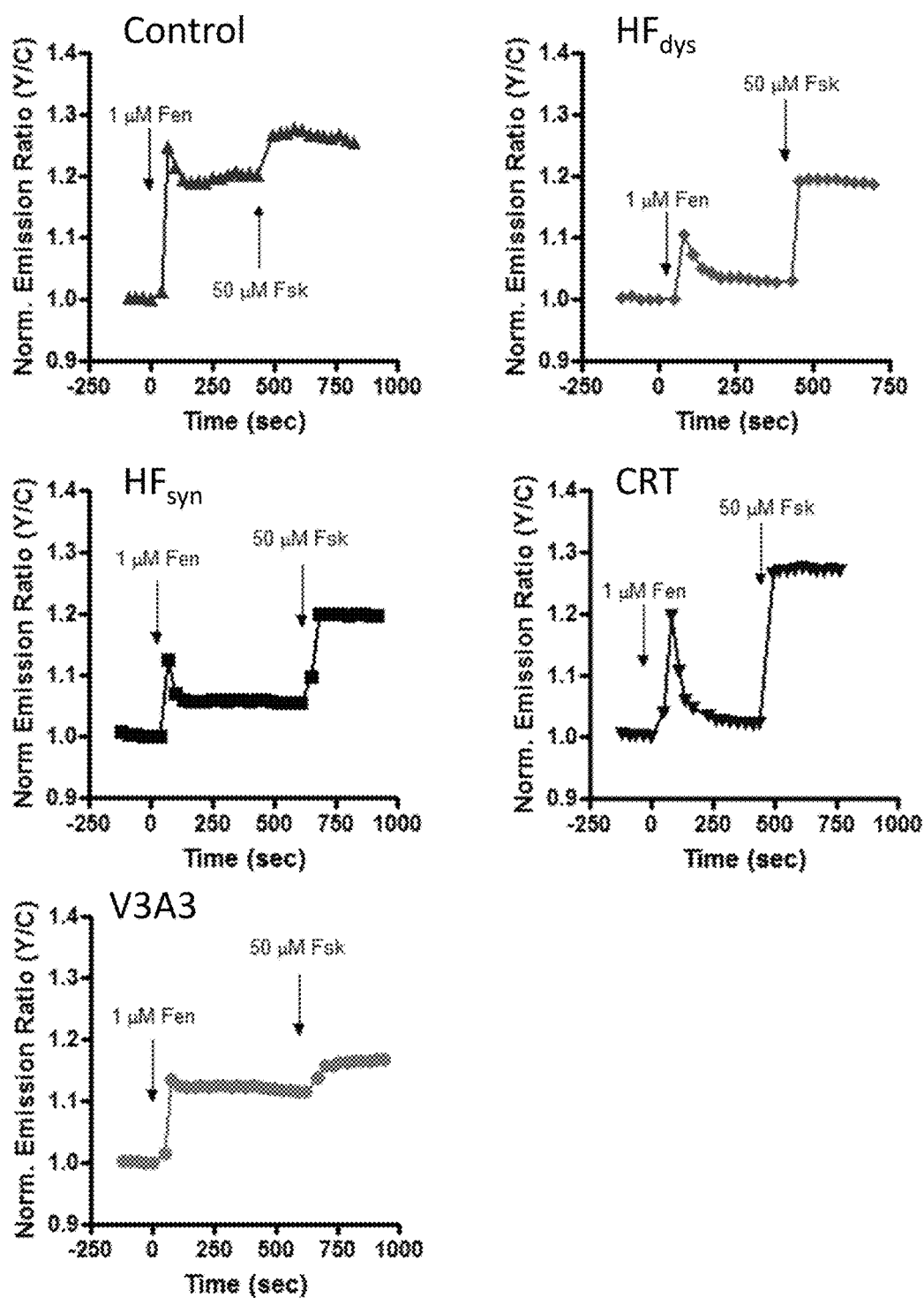
FIG. 7 shows the results of PKA activation by fenoterol, as indexed by AKAR3 in myocytes isolated from the five experimental models. Fenoterol stimulated PKA at the SR in all models. Summary data from n=4-5 in each group confirmed these responses.

Example 5: Biased $β_2$-AR Signaling is Coupled with Enhanced cAMP Generation and Protein Kinase A Activity at the Sarcoplasmic Reticulum To further clarify the nature of the altered $β_2$-AR signalling, studies were performed in isolated myocytes infected with an adenovirus containing a plasma membrane-targeted adenosine 3',5'-monophosphate (cAMP)-sensitive fluorescence resonance energy transfer (FRET) probe (ICUE3) based on the EPAC1 (exchange protein directly activated by cAMP 1) binding domain (FIG. 6A; DiPilato et al. (1999) *J Biol Chem.* 274:22048-22052). After 24 hours, cells were stimulated with either zinterol or fenoterol, each in the presence of a broad-spectrum phosphodiesterase (PDE) inhibitor, IBMX. Zinterol-stimulated cAMP increase in both resynchronization models exceeded that in the other groups (including control). In contrast, all responded similarly to fenoterol (FIG. 6C), as had been observed with sarcomere shortening. This indicated that $Gα_s$-coupled signalling was not blunted in these models, but rather, there was bias away from $Gα_i$ coupling. Because PDEs were broadly inhibited, the results support differential cAMP generation rather than hydrolysis. Previous studies have proposed that reduced $Gα_i$ coupling to the $β_2$-AR can modify the targeting of cAMP, resulting in enhanced protein kinase A (PKA) activation of sarcoplasmic reticulum (SR) calcium handling proteins and thus augmentation of the $Ca^{2+}$ and associated myocyte shortening (Kuschel et al. (1999) *J. Biol. Chem.* 274:22048-22052). Attempts to identify compartmentalized cAMP signalling in the canine myocytes using targeted FRET probes proved unsuccessful, but cells were successfully infected with a virus containing a FRET-based PKA activity reporter (AKAR3) target to the SR (FIG. 6D; Liu et al. (2011) *Biochem Biophys Res Commun.* 404:581-586). In myocytes from $HF_{dys}$ or $HF_{syn}$, zinterol resulted in negligible PKA stimulation detected at the SR, whereas in CRT cells, activation was detectable (FIG. 6F). As a control, fenoterol was used and PKA activation was detected in cells from all models (FIG. 7).

Example 6: Effect of Resynchronization on β-AR-Coupled and -Regulating Proteins

Figure 8A:
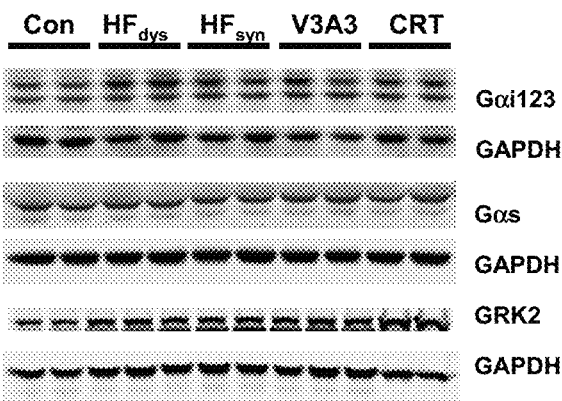
FIGS. 8A-8B show that protein expression of $G\alpha_i$ and GRK2 but not Gas increases in each HF model over control. Western blots (FIG. 8A) and summary densitometry (FIG. 8B) for protein levels of $G\alpha_i(1,2,3)$, $G\alpha_s$, and GRK2 (n=4 to 5 per group) are shown. The analyses were normalized to GAPDH as a loading control. * represents p<0.05 versus control.
Figure 8B:
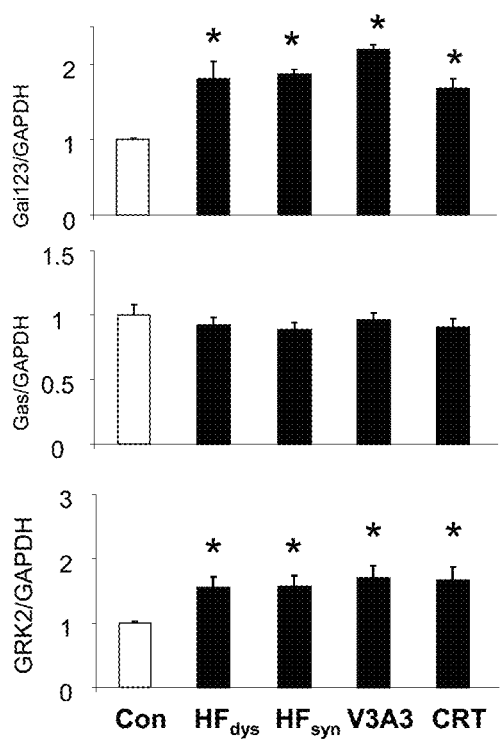
Figure 9:
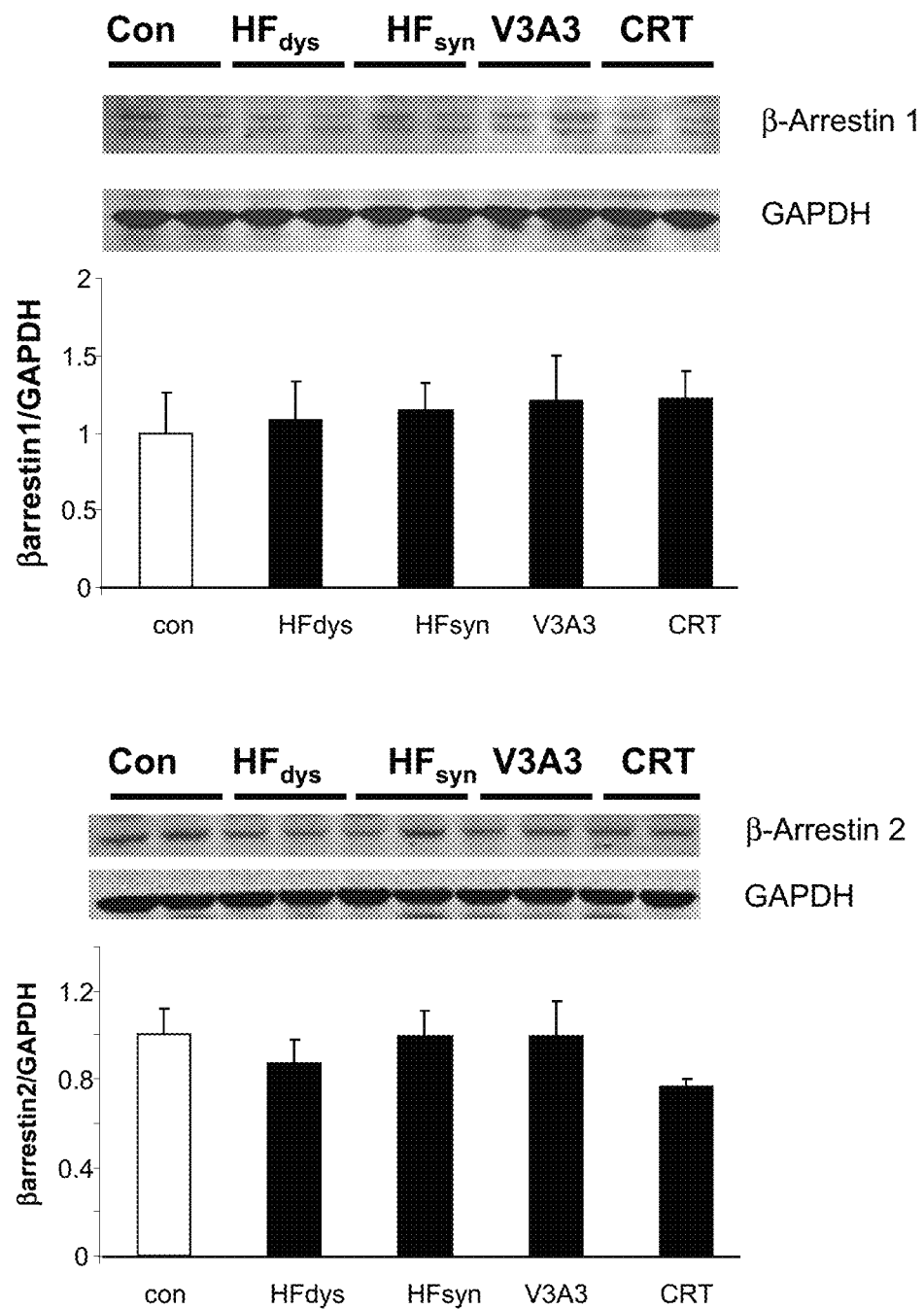
FIG. 9 shows myocardial protein expression levels of β-arrestin1 and β-arrestin2 in control and four HF models. There were no significant changes among the models of heart failure or in comparison with normal control. n=4 dogs for each group.
Figure 11:
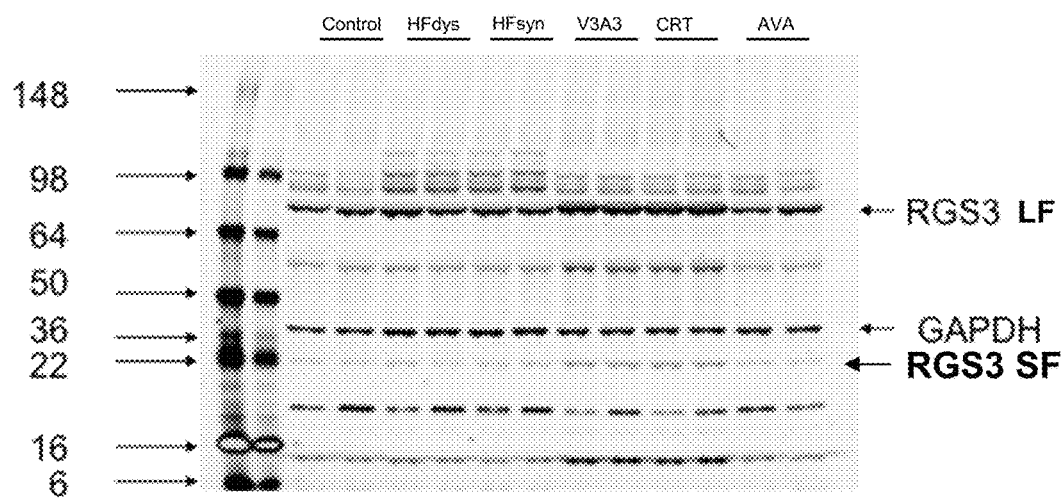
FIG. 11 shows full gel electrophoresis results for RGS3 protein analysis which displays both long and short form expression changes. RGS3 long form (LF, 70 kDa) and short form (SF, 25 kD) are shown. The long form band is displayed in FIG. 13.
Figure 12:
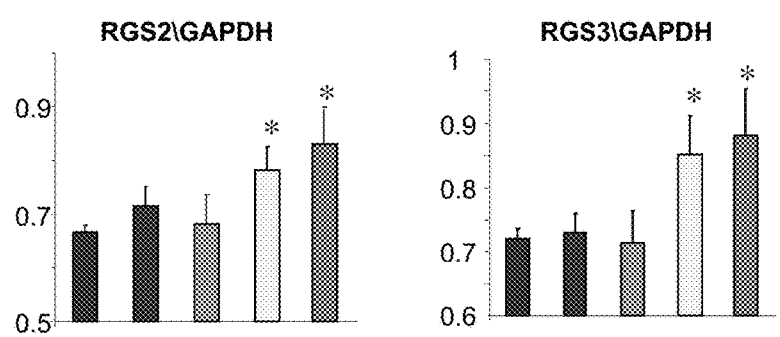
FIG. 12 shows mRNA expression levels of RGS2 and RGS3 from control and four HF models. RGS2 and RGS3 expression rose with both resynchronization models, but not in the other HF models, whereas RGS4 increased similarly in all HF models. * represents p<0.05 versus control (CON).

Depression of β-adrenergic stimulatory signaling in HF has been linked to up-regulation of $G_i$ expression (Xiao et al. (2003) *Circulation.* 108:1633-1639; Gong et al. (2000) *Br. J Pharmacol.* 131:594-600; and Rau et al. (2003) *FASEB J.* 17:523-525) and G receptor kinase 2 (GRK2; Raake et al. (2008) *Circ Res.* 103:413-422), the latter coupled to β-AR desensitization by internalization and degradation. Both were observed in $HF_{dys}$ and $HF_{syn}$ models (FIGS. 8A and 8B), but were similarly enhanced in both resynchronization models. $Gα_s$ expression was unaltered between models and versus normal controls. We also performed Analysis of β-arrestin1 and β-arrestin2 expression, but there were no consistent differences between models (FIG. 9). Another mechanism to regulate $Gα_i$ proteins is via regulators of G protein-coupled signaling (RGS), whose canonical role is as guanosine triphosphatase (GTPase)-activating proteins (GAPs) to reverse a subunit activity. In heart muscle, RGS3 and RGS4 are recognized to target $Gα_i$. Although RGS2 is thought to more prominently target $Gα_q$, recent evidence also supports $Gα_i$ regulation. Thus, all three forms were examined. As shown by Western blot analysis (FIGS. 10A and 10B), $HF_{syn}$ and $HF_{dys}$ expressed low levels of RGS2/3 protein, similar to controls, but both were up-regulated in each of the resynchronization models. In contrast, RGS4 was not significantly altered. RGS3 expression shown in FIG. 10 reflected the long form (~70 kD), but differential expression was observed in the short form (~25 kD) as well (FIG. 11). Changes in RGS2/3 protein expression were mirrored by gene expression (FIG. 12), indicating that they might provide a biomarker of CRT response. To test this, mRNA expression from left ventricular (LV) myocardial biopsy specimens obtained in 15 HF patients with dyssynchrony were determined at baseline and 4 months after initiating CRT. All had idiopathic dilated cardiomyopathy (12 men), with mean age of 66±2 years, New York Heart Association (NYHA) symptom score of 3.4±0.1, QRS duration of 158±4 ms, and resting ejection fraction (EF) of 22.1±1.5%. Of these patients, nine were clinical responders (relative increase in EF of 20% or more and fall in functional class >1) (Vanderheyden et al. (2008) *J Am Coll Cardiol.* 51:129-136), and in these patients, RGS2 and RGS3 expression increased significantly, whereas this was not observed in nonresponders (FIG. 10C). Thus, enhanced RGS2/3 expression is also observed in humans receiving CRT who demonstrate clinical benefit. There were no disparities or changes in gene expression of $G\alpha_i$ or β-arrestin2 in these same patients.

Figure 13A:
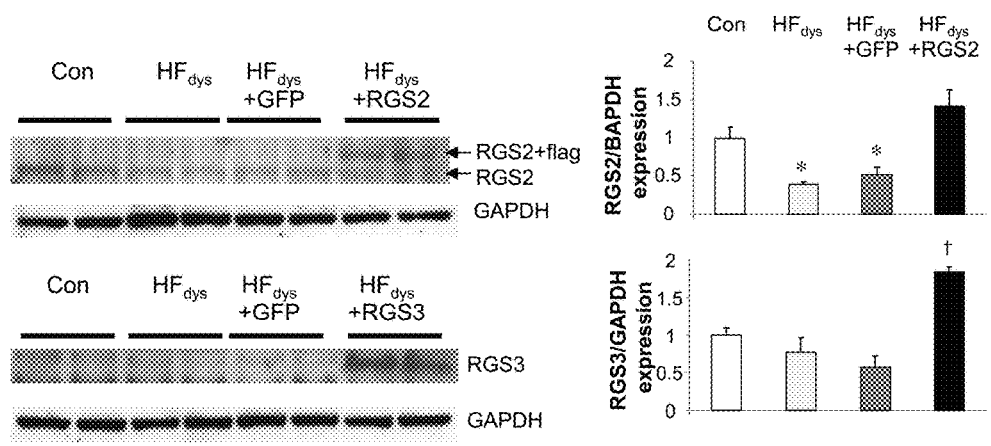
FIGS. 13A-13B show that up-regulation of RGS2 and/or RGS3 in $HF_{dys}$ myocytes is sufficient to convert the $\beta_2$-adrenergic stimulation phenotype to that of CRT (or V3A3) responses.
Figure 13B:
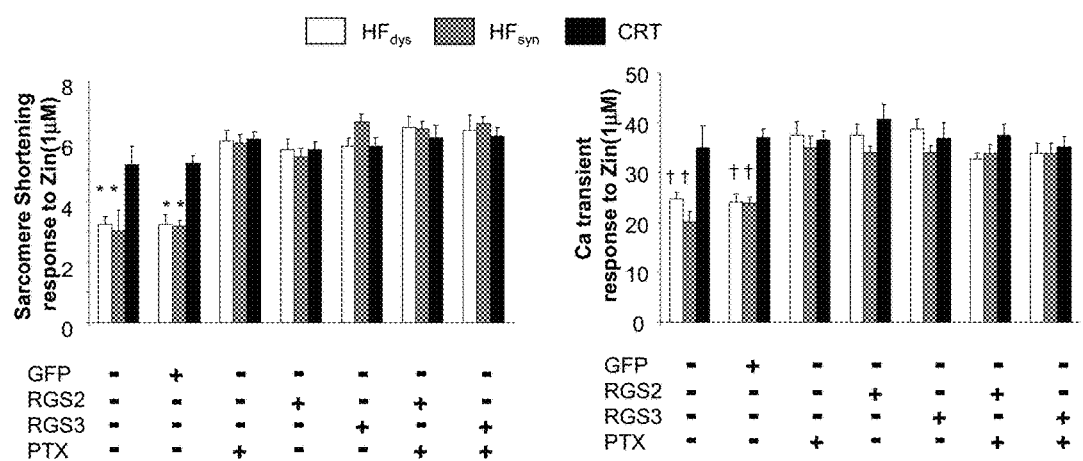

Example 7: RGS2/3 Up-Regulation is Sufficient to Explain Biased $\beta_2$ Response in Resynchronized Models To test whether up-regulation of either RGS2 and/or RGS3 is sufficient to explain differential $\beta_2$ responses, myocytes from $HF_{dys}$, $HF_{syn}$, and CRT were isolated with adenovirus expressing green fluorescent protein (GFP) (control) or wild-type RGS2 orRGS3 (FIG. 13A). Transfection with GFP did not alter RGS expression, but levels increased two- to three-fold in isolated myocytes, similar to that observed in vivo. Cell function and $Ca^{2+}$ handling were studied after 24 hours, and it was found that up-regulation of RGS2 and/or RGS3 enhanced sarcomere shortening and peak $Ca^{2+}$ response to zinterol, similar to that with zinterol+PTX (FIG. 13B). There was no further augmentation by combining RGS2 and/or RGS3 infection with PTX, indicating that targeting was likely similar.

Figure 14A:
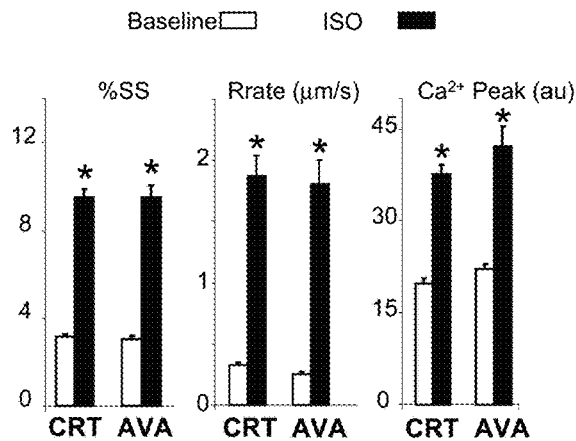
FIGS. 14A-14D show enhanced β-AR responsiveness in myocytes from hearts exposed to RV (dyssynchrony) pacing during the middle 2 weeks of otherwise 6-week atrial tachypacing (AVA).
Figure 14B:
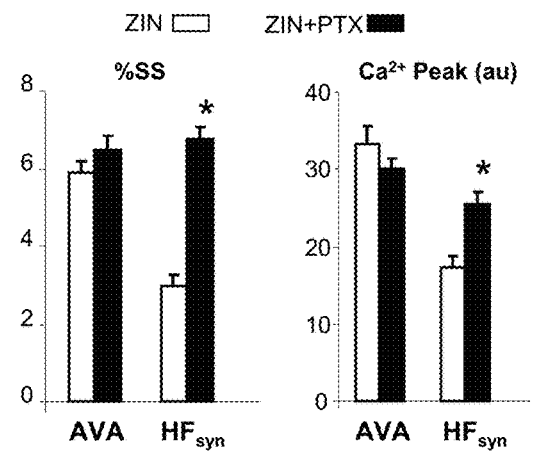
Figure 14C:
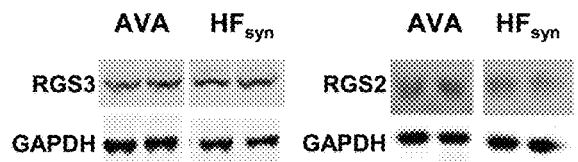
Figure 14D:
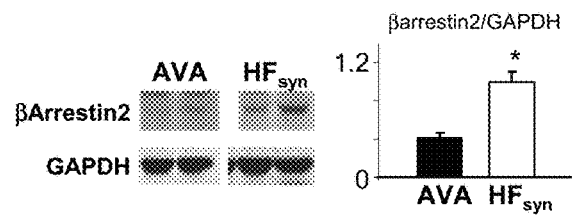
Figure 15:
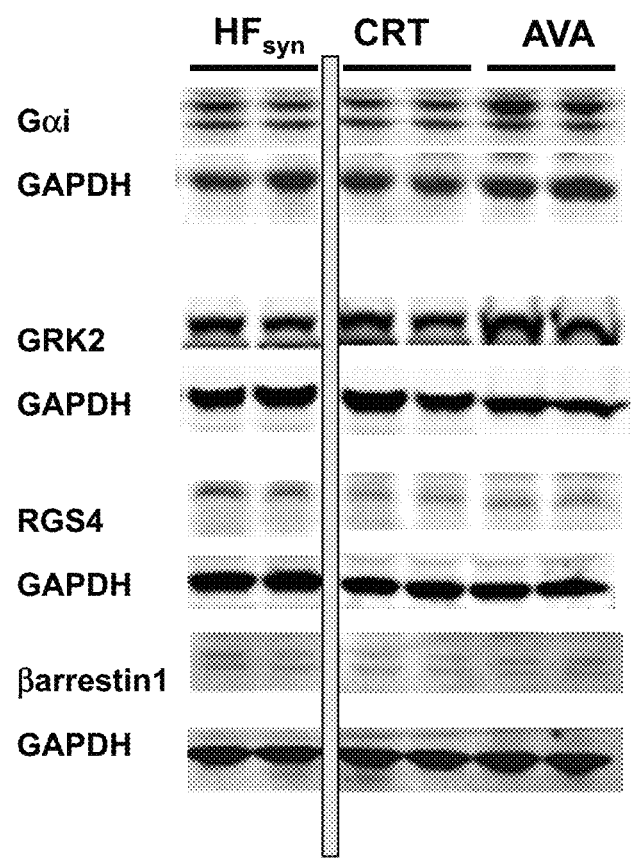
FIG. 15 shows protein expression of Gα$_i$(1,2,3), GRK2, RGS4, and β-arrestin1 in the AVA versus HF$_{syn}$ models. None of these proteins was observed to be expressed at levels different from the other HF models. Data shown here contrast to HF$_{syn}$, which is the model closest to AVA.

Example 8: Transient Dyssynchrony in Synchronous HF Induces $G\alpha_s$-Biased $\beta_2$-AR Signaling The finding that restoring synchrony from a dyssynchronous HF state was required to induce the changes in $\beta_2$-AR signalling led to the hypothesis that exposure to dyssynchrony in otherwise synchronous HF could induce a similar response. If so, then a seemingly paradoxical therapy of transient RV pacing might improve adrenergic responsiveness in $HF_{syn}$. To test this hypothesis, dogs (n=5) were sequentially exposed to atrial, RV, and then atrial tachypacing, each for 2 weeks (model referred to as AVA); the only difference between $HF_{syn}$ and AVA was the middle 2-week period. Global heart function at 6 weeks was similar to the other HF models (for example, EF, ~30%; end-diastolic pressure, 33 mmHg; dP/dtmax/IP, 16 s−1). As shown in FIG. 14A, isoproterenol-stimulated shortening, relaxation, and peak calcium in AVA myocytes were similar to that from CRT hearts. AVA cells also responded robustly to zinterol, which was not further altered by PTX, in contrast to $HF_{syn}$ behaviour (FIG. 14B). Unlike CRT, neither RGS2 nor RGS3 expression increased in the AVA model (FIG. 14C). RGS4, $G\alpha_i$, GRK2, and β-arrestin1 expression were also similar (FIG. 15) to levels observed in the other HF models (FIG. 15). However, a substantial decline in β-arrestin2 in AVA was observed, which was below that in the other HF models and in controls (FIG. 14D). Because β-arrestin can switch $\beta_2$-AR signalling toward $G\alpha_i$-coupled cascades (Baillie et al. (2003) *Proc. Natl. Acad. Sci. U.S.A.* 100:940-945), this change might be related to the loss of such coupling with AVA.

Despite the overall clinical success of CRT over the past decade, cellular and molecular mechanisms by which it confers sustained benefits are only recently being revealed. Identifying these mechanisms offers an opportunity to apply changes induced by CRT to a broader HF population without involving biventricular stimulation. The results shown in the previous examples has advanced this goal in several ways. First, it has been shown that depressed myocyte function, calcium handling, and β-AR responsiveness in synchronous or dyssynchronous HF are much improved in hearts that were first dyssynchronous and later resynchronized. Second, a major change underlying adrenergic reserve was identified herein to be Gas-biased $\beta_2$-AR signaling ($G\alpha_i$ decoupling) that enhances cAMP activation and stimulation of PKA within the SR, improving cell $Ca^{2+}$ cycling and contraction. This modification is coupled to enhanced RGS2 and RGS3 expression, changes also found in humans responsive to CRT. A similar improvement in rest and β-AR response was achieved by temporarily rendering contraction dyssynchronous by RV pacing, although here the molecular mechanism may differ, potentially involving β-arrestin2 modification. These results identify a key signaling change from CRT that could potentially benefit all forms of HF either by cardiac targeted RGS2/3 enhancement or by novel uses of traditional ventricular pacing.

These results indicate several methods to translate benefits from CRT to HF patients who are otherwise not candidates and/or respond poorly to CRT. One is that CRT in general may be enhanced by intermittently using RV pacing to stimulate molecular signalling changes that are subsequently and beneficially modified by reinstating CRT. This might enhance effects in CRT nonresponders. More provocatively, the AVA data indicate that one might purposely induce dyssynchrony by RV pacing in synchronous HF for a limited duration (weeks to a few months) and then revert to normal sinus. Many HF patients receive implantable defibrillators to counter a high risk of sudden death, and these systems could be easily modified for this purpose. Enhancement of RGS2 and/or RGS3 in the heart would benefit from myocyte targeting given their ubiquitous expression in multiple cell types. Adeno-associated virus gene transfer methods are being tested for clinical heart disease (Rapti et al. (2011) *Can J Cardiol* 0.27:265-283), and this might be further developed. Last, fenoterol as a mixture of R,R-enantiomer and S,S-enantiomer was first developed for asthma, but worsened death (Pearce (2009) *J Clin Epidemiol.* 62:582-587). However, the use of the R,R-enantiomer alone for heart disease was never examined and may still prove a viable treatment. Such therapeutic strategies take advantage of the results described herein that the $\beta_2$-AR becomes uncoupled from $G_i$ proteins in dyssynchronous failing hearts that are subsequently resynchronized, potently contributing to systolic reserve. This is not observed in HF where contraction is either always synchronous or always dyssynchronous. Whether achieved by pacemaker-induced transient dyssynchrony or by up-regulation of RGS2/3 proteins, the improved reserve can be induced in other forms of HF.

Example 9: Materials and Methods for Examples 10-13

A. Canine Pacing Models

Figure 16:
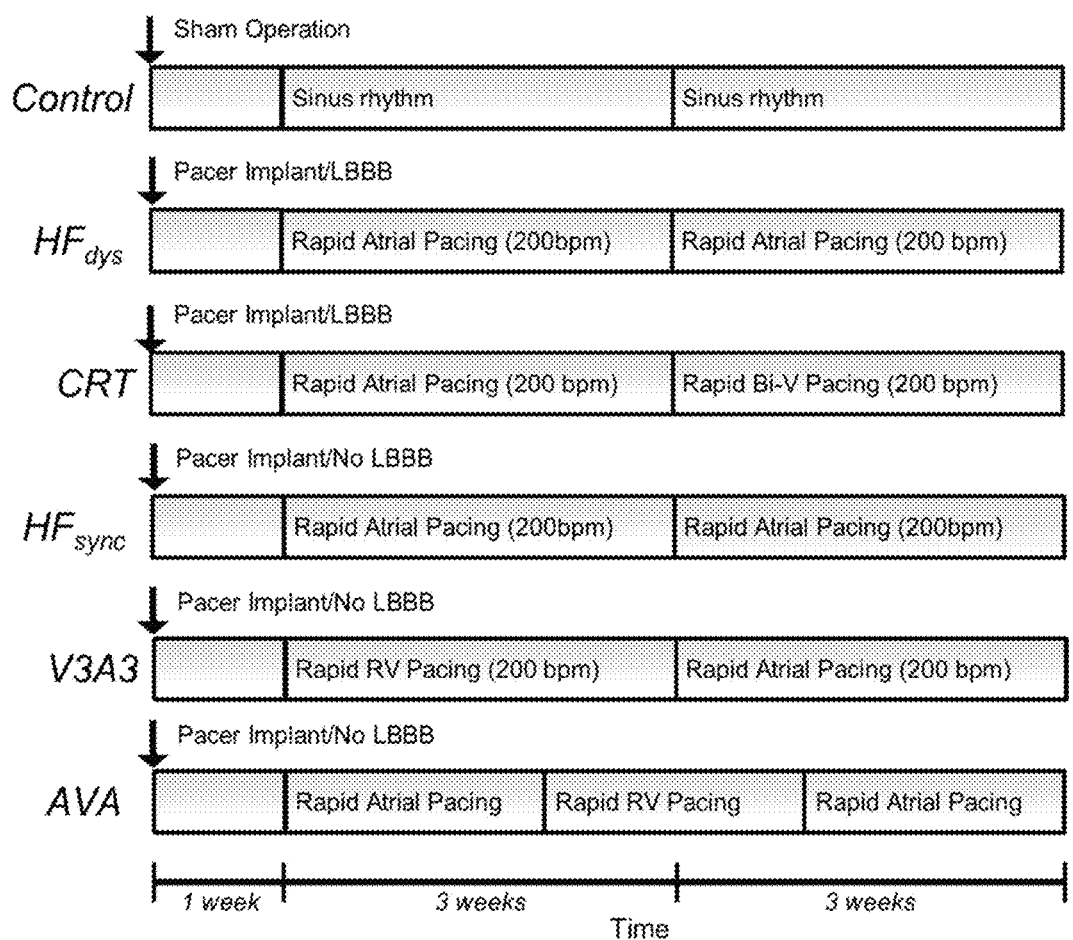
FIG. 16 shows a timeline of pacing protocols in each of the canine models: control, dyssynchronous heart failure (HF$_{dys}$), cardiac resynchronization therapy (CRT), synchronous heart failure (HF$_{sync}$), V3A3 (3 weeks RV pacing to induce dyssynchrony, 3 weeks atrial pacing to restore synchrony), and AVA (2 weeks atrial synchronous pacing, 2 weeks RV dyssynchronous pacing, and 2 weeks atrial synchronous pacing). The HF$_{dys}$ and CRT models received a left bundle branch block via radio-frequency ablation. After a 1 week recovery period from the pacemaker implant, each pacing protocol lasted 6 weeks before the animal was sacrificed.
Figure 17A:
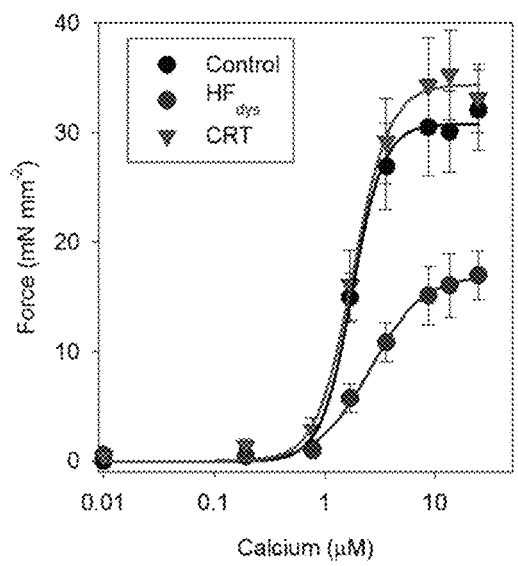
FIGS. 17A-17D show steady-state force-calcium data from skinned RV trabecular muscles. Force is normalized by cross-sectional area. Data points are mean±SEM. Data points and fitted curve for control, HF$_{dys}$, CRT, HF$_{syn}$, V3A3, and AVA.
Figure 17B:
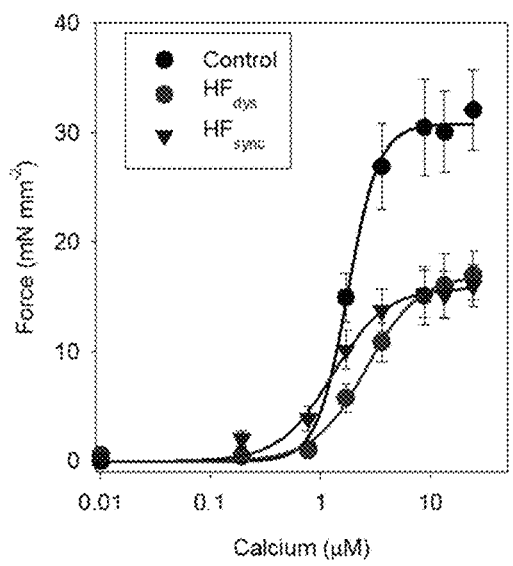
Figure 17C:
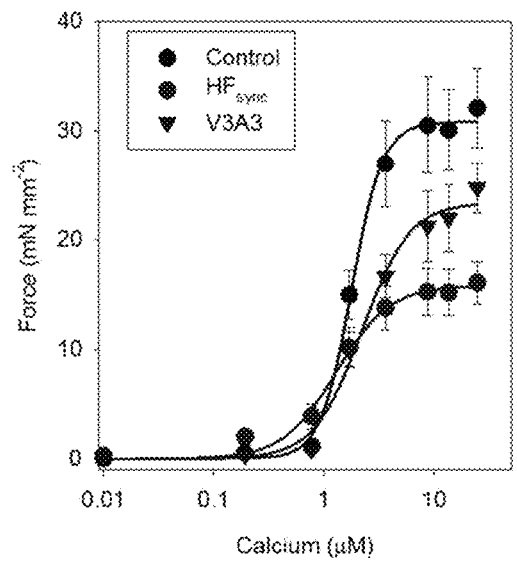
Figure 17D:
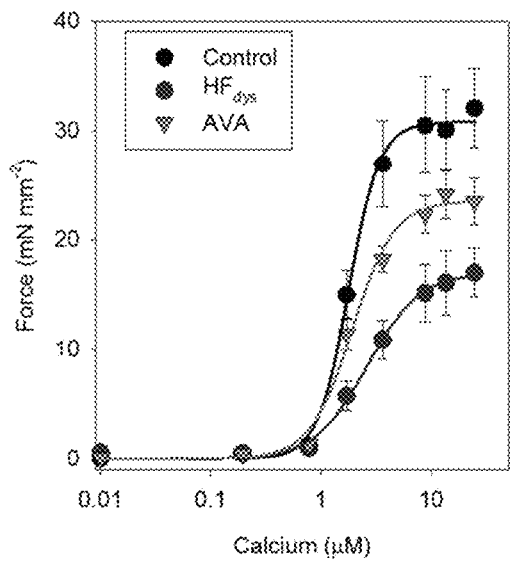

Details of the canine model have previously been reported in Chakir et al. (2008) *Circulation* 117:1369-1377; Chakir et al. (2009) *Circulation* 119:1231-1240; Spragg et al. (2003) *Circulation* 108:929-932; and Leclercq et al. (2002) *Circulation* 106:1760-1763. All dogs except control dogs received a pacemaker implant (Medtronic). The dyssynchronous heart failure ($HF_{dys}$) and CRT models received left bundle branch block (LBBB) via radio-frequency ablation at the time of pacemaker implant. After a 1 week recovery period, all dogs received six weeks of tachypacing (~200 bpm). The location and timing of pacing was different for each of the five experimental models and shown in FIG. 16. Control dogs were non-paced, non-failing, healthy dogs. $HF_{dys}$ received LBBB to achieve dyssynchrony and were subjected to six weeks right atrial (RA) tachypacing. The CRT dogs also received a LBBB to induce dyssynchrony along with three weeks RA tachypacing, then three weeks of biventricular (biV) tachypacing (resynchronization). The synchronous heart failure dogs ($HF_{sync}$) received no LBBB and were subjected to RA tachypacing for six weeks. The V3A3 model was tachy-paced at the right ventricle (RV) for three weeks to induce dyssynchrony and then tachy-paced at the RA for three weeks (resynchronization without biV stimulation). The AVA model was paced similarly to the $HF_{syn}$ model, but received two weeks of RV tachypacing in the middle of the protocol to induce transient dyssynchrony. At the end of the study, animals were anesthetized with pentobarbital and hearts were excised under ice cold cardioplegia.

B. Myofilament Function Analyses

Trabeculae were isolated from RV free wall and skinned overnight in the presence of 1% Triton X-100, protease (Sigma), and phosphatase (Roche) inhibitor cocktails. The trabeculae was then attached, via the "basket and hook" technique (Gao et al. (1994) *Circ. Res.* 74:408-415) to a force transducer (SI Heidelberg) and stationary hook. Force was measured as the calcium concentration in the bath was increased from 0 to saturating conditions. A subset of the trabeculae were treated with a phosphatase following the first force-calcium experiment. The muscle was exposed to 25,000 mU/mL PP1 (NE Biolabs) for 60 minutes and a second force-calcium curve was collected. Tissue from the endocardium layer of the left ventricular (LV) lateral wall were frozen in liquid nitrogen and stored at −80° C. Subsequently, the tissue was homogenized in the presence of Triton X-100, protease (Sigma), and phosphatase (Roche) inhibitor cocktails to prepare skinned myocytes. Myocytes were then glued using silicone to the tips of 150 µm diameter minutia pins attached to a force transducer and motor arm. Force was measured as the myocyte was exposed to increasing calcium. All force-calcium data was then fit to the Hill Equation. Data are presented as mean±SEM.

C. Proteomic Analyses

Tissue samples from control, $HF_{dys}$, and CRT hearts were treated to obtain a myofilament-enriched protein sample as previously described in Arrell et al. (2001) *Circ. Res.* 89:480-487 in the presence of protease (Sigma) and phosphatase (Roche) inhibitor cocktails. Samples were then run on a 1D SDS gel, and the lanes were divided into several bands to avoid high abundant proteins (e.g., myosin) from overwhelming the samples. The gel pieces were then subjected to standard in-gel digestion and enriched for phosphopeptides using Phos-TiO kits (GL Science). Samples were then desalted and run on Orbitrap hybrid mass spectrometer (MS) (Thermo). Myofilament-enriched samples were also run on phos-Tag gels (Wako Pure Chemical Industries, Ltd.), transferred to a membrane and cardiac troponin I (cTnI) was detected with the 81-7 cTnI antibody. The cTnI Ab was also used on samples run on conventional ID gels to detect cTnI degradation products.

Example 10: CRT Restores Myofilament Function

Figure 18A:
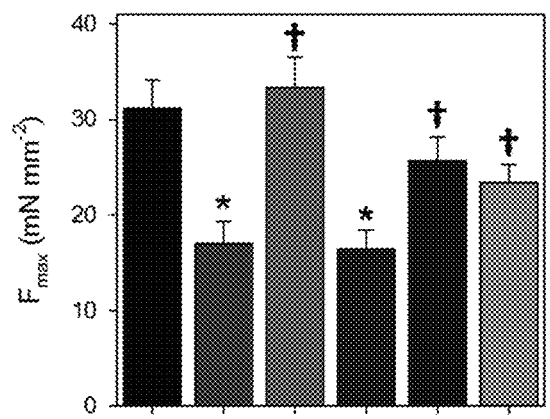
FIGS. 18A-18C show Hill equation indices for the 5 models, showing maximal calcium-activated force (F$_{max}$) (FIG. 18A), calcium concentration which generated 50% of F$_{max}$ (EC$_{50}$) (FIG. 18B), and Hill coefficient (n$_H$) (FIG. 18C). * represents p<0.05 versus control and † represents p<0.05 versus HF$_{dys}$ or HF$_{sync}$.
Figure 18B:
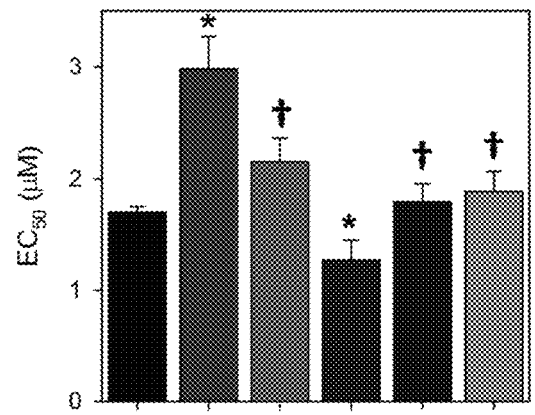
Figure 18C:
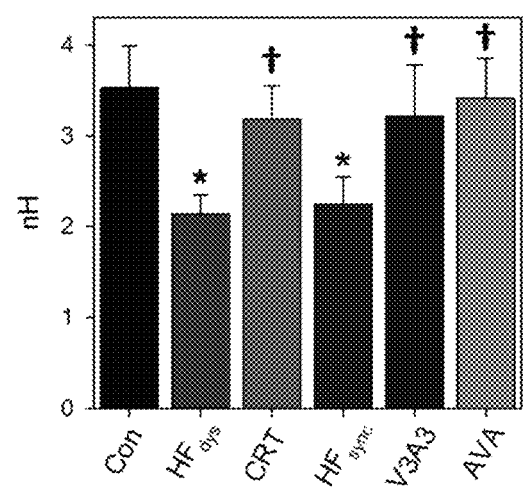

Steady state force-calcium data from skinned right ventricular trabecular are shown in FIGS. 17 and 18, with both the raw data and fitted curves (FIG. 17) and the calculated indices (FIG. 18) provided. All indices of myofilament function were depressed in the $HF_{dys}$ dog relative to the control. Maximal calcium activated force ($F_{max}$) in control (Con) dogs was 31.1±3.0 mN·mm$^{-2}$ (n=14 trabeculae from 8 dogs) and was reduced by approximately 50% in $HF_{dys}$ to 17.0±2.3 mN·mm$^{-2}$ (n=24 trabeculae from 13 dogs) (P<0.01). The calcium required for 50% force activation ($EC_{50}$) was increased in $HF_{dys}$(Con: 1.7±0.05 µM, $HF_{dys}$: 2.98±0.29 µM, P<0.01), denoting a decrease in calcium sensitivity. The Hill coefficient ($n_H$), an approximate measure of cooperativity, was also decreased (Con: 3.52±0.47, $HF_{dys}$: 2.14±0.20, P<0.01). All of these indices, however, were restored by CRT ($F_{max}$: 33.31±3.21 mN·mm$^{-2}$, $EC_{50}$: 2.15±0.22 µM, $n_H$: 3.18±0.36, P<0.05 vs. $HF_{dys}$, P=N.S. vs. control, n=18 trabeculae from 9 dogs).

The recovery of myofilament function with CRT was not merely due to contraction being synchronous, as function was also depressed in the $HF_{sync}$ dog as well. As with $HF_{dys}$, $HF_{sync}$ had reduced $F_{max}$ (16.46±1.93 mN·mm$^{-2}$, P<0.01 vs Con and CRT, P=N.S. vs $HF_{dys}$, n=22 trabeculae from 8 dogs), and $n_H$ (2.25±0.30, P<0.05 vs Con, P=0.057 vs CRT, P=N.S. vs $HF_{dys}$). However, where $HF_{dys}$ had a decrease in calcium sensitivity, $HF_{sync}$ showed an increase (1.27±0.17 µM, P<0.01 vs Con, CRT and $HF_{dys}$).

The V3A3 model, a straight forward variation on CRT, also showed significant recovery of $F_{max}$ (25.72±2.47 mN·mm$^{-2}$, P<0.05 vs $HF_{dys}$ and $HF_{sync}$, P=N.S. vs. Con, n=13 trabeculae from 5 dogs). Calcium sensitivity and cooperativity were also returned to baseline conditions ($EC_{50}$=1.80±0.16 µM, $n_H$=3.21±0.57, P<0.05 vs $HF_{dys}$, P=N.S. vs. Con).

More intriguing were results from the other variation on CRT, the AVA model. These hearts are similar to $HF_{sync}$ except that they are exposed to two weeks of RV pacing in the middle period to induce dyssynchrony which it then removed. The AVA model also showed a significant increase in $F_{max}$ (23.4±1.9 mN·mm$^{-2}$, P<0.05 vs $HF_{syn}$, P=N.S. vs. Con, n=10 trabeculae from 5 dogs). Again, similar to CRT and V3A3, the AVA dogs exhibited a recovery of calcium sensitivity and cooperativity ($EC_{50}$=1.89±0.17 µM, $n_H$=3.41±0.44, P<0.05 vs $HF_{sync}$, P=N.S. vs. Con).

Example 11: Function is Restored Independent of Region

Intact trabeculae could only be reliably obtained from the RV free. Whether the late-activated lateral LV wall behaved similarly was also determined. As muscle fibers could not be dissected from this region, skinned myocytes were analyzed. FIG. 19A shows a skinned myocyte isolated from the endocardium of the left ventricular lateral wall, FIG. 19B shows the raw data and fitted curves, and FIGS. 19C-19D show the indices. As was observed in the RV, compared to control, $HF_{dys}$ exhibited decreased $F_{max}$ (Con: 35.00±4.61

93 mN·mm$^{-2}$, n=7 myocytes from 3 dogs, HF$_{dys}$: 13.44±1.66 mN·mm$^{-2}$, n=7 myocytes from 3 dogs, P<0.01), and decreased calcium sensitivity (Con: 1.92±0.16 µM, HF$_{dys}$: 2.58±0.11, P<0.01). These parameters were returned to near control values in the CRT dog (F$_{max}$: 36.16±2.78 mN·mm$^{-2}$, EC$_{50}$: 2.00±0.19 µM, n=8 myocytes P<0.05 vs HF$_{dys}$, P=N.S. vs Con).

Again, similarly to the RV, HF$_{sync}$ myocytes from the LV lateral wall exhibited decreased F$_{max}$ (16.44±2.31 mN·mm$^{-2}$, n=8 myocytes from 3 dogs, P<0.01 vs. Con), but a significant increase in calcium sensitivity (1.51±0.10 µM, P<0.05 vs. Con).

Example 12: Calcium Sensitivity is Mediated by Phosphorylation

Examples of trabeculae before and after PP1 treatment are shown in FIG. 20A and the effect on F$_{max}$ and EC$_{50}$ are shown in FIG. 20B. None of the groups had a statistically significant change in F$_{max}$ after treatment (P=N.S.). There was an increase in EC$_{50}$ in control (ΔEC$_{50}$: 1.09±0.22 µM, n=6), CRT (ΔEC$_{50}$: 0.70±0.23 µM, n=5), HF$_{sync}$ (ΔEC$_{50}$: 0.87±0.19 µM, n=8), V3A3 (ΔEC$_{50}$: 1.51±0.51 µM, n=4), and AVA (ΔEC$_{50}$: 1.53±0.47 µM, n=4), but there was no effect on HF$_{dys}$ trabeculae (ΔEC$_{50}$: −0.06±0.14 µM, n=5, P<0.05 vs Con and CRT).

Example 13: Pacemaker that Transiently Induces Dyssynchrony

As discussed elsewhere herein, a subject in heart failure may benefit from being restored to synchronous contraction of the left ventricle, including subjects with no history of dyssynchronus LV contraction. Consequently, inducing transient LV contraction dyssynchrony in synchronous heart failure patients and then reversing it may actually be of some benefit.

A pacemaker may be programmed to induce left ventricular dyssynchrony transiently by switching between two modes: (1) a normal pacing mode, i.e., a "non-ventricular" pacing mode that monitors atrial electrical activity and applies atrial pacing through an atrial stimulation electrode if the atrial rate falls below a predetermined threshold; and (2) a dyssynchrony-inducing mode, i.e., a "ventricular" pacing mode that monitors atrial activity as in the normal mode but then applies ventricular pacing through a ventrical stimulation electrode at a single ventricular site. The ventricular stimulation is timed so that it is given slightly before the normal atrioventricular conduction would have stimulated the LV to contract. The LV contracts dyssynchronously because depolarization at a single site causes propagation from cell to cell through the gap junctions, which is a slow process compared to electrical propagation through the Purkinje fibers. The LV thereby contracts dyssynchronously as the wave of depolarization slowly propagates from the stimulation site over the LV. This type of pacing is also termed "pre-excitation" pacing, because the pacing pulses arrive before those of normal conduction. This programming is provided in a controller of the pacemaker. The pacemaker also includes a power source and the atrial and ventricular stimulation electrodes.

The pacemaker may be programmed to alternate between the normal mode and the dyssynchrony-inducing mode, in order to provide repeated periods of resynchronization following induced dyssynchrony. The time periods may vary widely, from a few minutes, to a few hours, to a day, to several days, to a week, to several weeks, to a month, or to several months. The period of normal pacing is typically (but not necessarily) equal to or longer than the period of dyssynchrony. Exemplary operational programs include:
- alternate between the normal pacing mode and the dyssynchrony-inducing mode in a cycle, with a cycle length of one month.
- apply the dyssynchrony-inducing mode for one week of the cycle and normal pacing for the remainder of the cycle.
- apply the dyssynchrony-inducing mode for two weeks of the cycle and normal pacing for the remainder of the cycle.
- the dyssynchrony-inducing mode period of time is one day, and the normal pacing mode period of time is one or more days.
- the dyssynchrony-inducing mode period of time is two days, and the normal pacing mode period of time is two or more days.
- apply the dyssynchrony-inducing mode during nighttime or when the subject is asleep, and to apply the normal pacing mode for the rest of each day.

The dyssynchrony-inducing stimulation is typically (though not necessarily) applied to one and only one site, to force propagation through the entire LV muscle cell-by-cell (comparatively slow) instead of synchronously depolarizing the LV through the normal conduction pathway (comparatively rapid). The single site of ventricular stimulation may be anywhere on the right ventricle or left ventricle.

Dyssynchronus pacing can also be targeted to the right ventricle much as described above for the left ventricle.

Example 14: The Phosphorylation Pattern is Altered in Dyssynchrony and CRT

Many phosphorylation sites were identified by MS in the myofilament- and phospho-enriched samples. Table 1 shows the myofilament protein phosphorylation sites which were identified in at least one of the three groups, but not all three (differentially phosphorylated). These sites are on actin, myosin binding protein C (MyBPC), and tropomyosin (Tm).

Figure 21A:
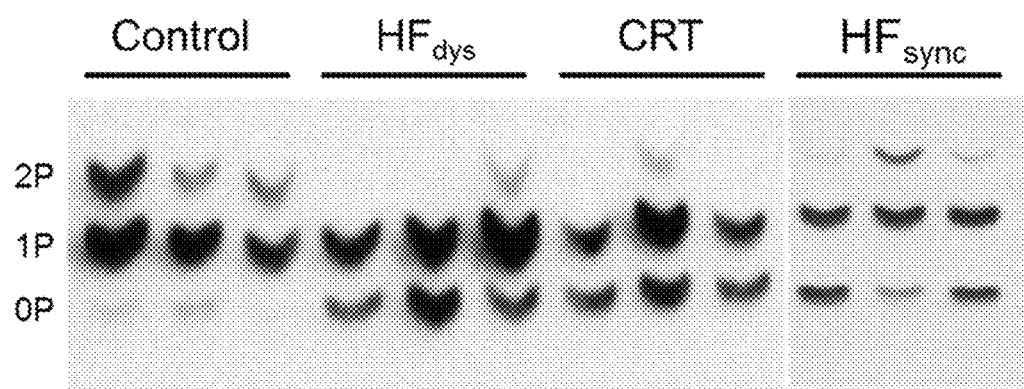
FIGS. 21A-21B show phosphorylated protein detection results.
Figure 21B:
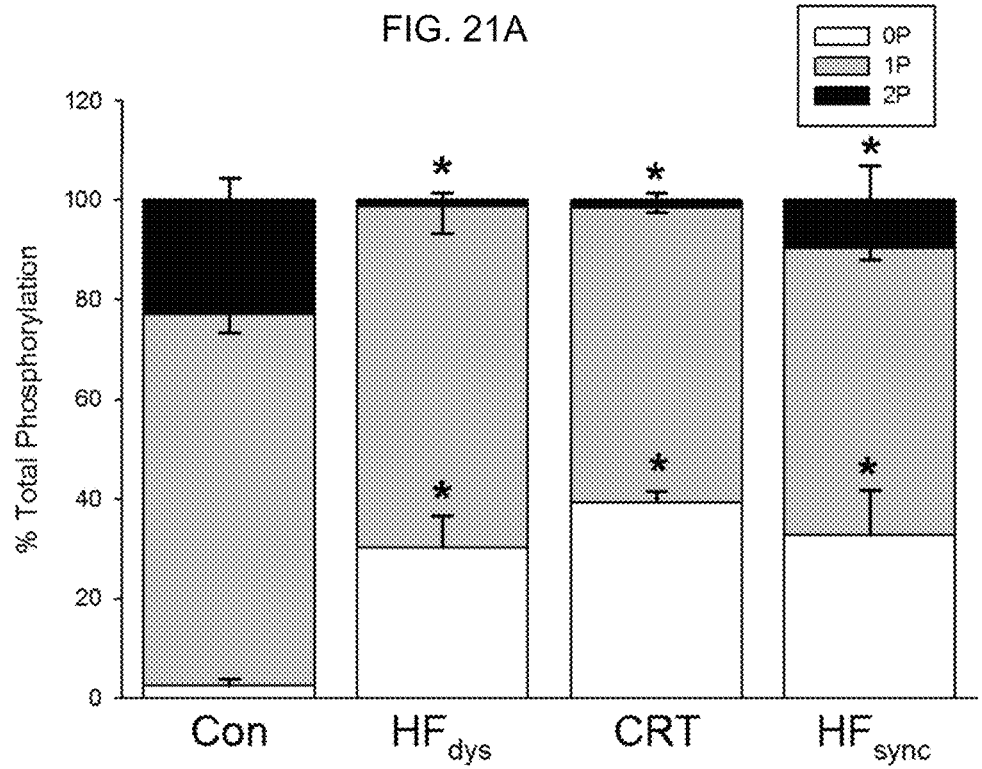

Troponin I phosphorylation is known to be a powerful mediator of contractility (Kirk et al. (2009) *Circ. Res.* 105:1232-1239), so it was studied using Western blots of phos-Tag and 1D gels. FIG. 21A shows the phos-Tag blot for control, HF$_{dys}$, and CRT, with the bands arbitrarily labeled as unphosphorylated (0P) up to 3 phosphorylation sites (3P). FIG. 21B shows the quantification of each site as a percentage of the total. Both HF$_{dys}$ and CRT had a statistically significant decrease in the 1P band (Con: 13±1%, HF$_{dys}$: 39±4%, CRT: 51±5%, n=3 per group, P<0.05). Moreover, the control dogs had no 0P band, but HF$_{dys}$ and CRT both had low levels (HF$_{dys}$: 8±11%, CRT: 4±2%). FIG. 21C shows a Western blot for cTnI run on a 1D gel, with the quantification of the degradation bands shown in FIG. 21D. There was an increase in degradation product in both HF$_{dys}$ and CRT (Con: 0.12±0.02, HF$_{dys}$: 0.34±0.04, CRT: 0.25±0.04, n=3 dogs per group, P<0.05 Con vs. HF$_{dys}$ and P=0.05 Con vs. CRT).

Thus, the data show that cardiac resynchronization therapy restores the ability of the myofilament to generate force in response to calcium. This indicates a mechanism for CRT's ability to improve systolic function in patients with heart failure yet also improve mortality. Moreover, the post-translational modifications that mediate this effect have been identified.

In the dog model of synchronous heart failure, HF$_{sync}$, a decrease in F$_{max}$ and an increase in calcium sensitivity was observed. Myofilament function in dyssynchronous heart failure, $HF_{dys}$ was similar to that in always synchronous HF in several, but not all aspects. While $F_{max}$ and $n_H$ declined similarly, $HF_{dys}$ cells displayed decreased calcium sensitivity. This suggests a novel mechanism by which dyssynchrony further worsens systolic function in the failing heart, consistent with clinical prognosis data (Iuliano et al. (2002) *Am. Heart J.* 143:1085-1091).

The CRT models, whether achieved by bi-ventricular pacing in the presence of a LBBB, or restoration of atrial stimulation following RV stimulation, each involved 3 weeks of $HF_{dys}$ followed by three weeks of $HF_{sync}$. This temporal sequence resulted in significant improvement in $F_{max}$, $EC_{50}$ and $n_H$ over what would transpire when either were administered alone for six weeks. In fact, the magnitude of improvement was so great with CRT, these indices returned to levels that resembled the control dog. This response is surprising because the CRT dog also received six weeks of tachypacing to induce heart failure, and the control dogs were non-paced, non-failing, healthy controls. At the intact chamber level, the CRT models did not appear as healthy controls either, but displayed elevation of diastolic pressures, reduced ejection fraction and contractile properties. All of these observations are consistent with the exposure to six weeks tachypacing. However, at the myocyte level, these were very different hearts.

If the calcium sensitizing effect is desirable, it may seem counter-intuitive that synchronous heart failure would lead to an increase in calcium sensitivity, as we saw in the $HF_{sync}$ model. The simultaneous decrease in $F_{max}$ and $n_H$ was so large, however, that the increase in calcium sensitivity would only result in increased force production at the very lowest of calcium concentrations, around the level of diastolic calcium. Administering a calcium sensitizer in this situation could endanger diastolic function, and lead to a situation where the myocardium generates too much force during diastole, but still too little during systole. This may be why calcium sensitizing drugs have not worked sufficiently. The sensitizing effect of CRT may only be beneficial after the desensitizing effect observed in $HF_{dys}$, so the calcium-force relationship looks identical to myofilament from healthy myocardium.

In order to rule out the possibility that the method of inducing dyssynchrony and resynchronization was responsible for the observed effects, an additional model of CRT, the V3A3 model, was developed. In V3A3 dyssynchrony is induced not by LBBB, but by right ventricular pacing, and resynchronization occurs by returning the pacing site to the atrium, not through biventricular pacing. This model recapitulated most of the effects of traditional CRT: changes in $F_{max}$, $EC_{50}$ and $n_H$ that return the myofilament to control levels. However, while $EC_{50}$ and nH were completely restored, the increase in $F_{max}$ was of smaller magnitude than what was observed in the CRT model. This may be because either RV pacing was not as efficient at generating dyssynchrony as a LBBB, or synchrony was not completely restored without biventricular pacing. Regardless, most of the effects were recapitulated in this model.

Given the observation that the temporal restoration of synchrony was required to observe the myofilament effects, it was determined whether the response could be replicated by taking synchronous HF and only transiently rendering the heart dyssynchronous. The AVA model is similar to the $HF_{sync}$ dog, except the middle 2 weeks are RV paced to induce transient dyssynchrony. The removal of the RV pacing during the last two weeks allowed the heart to resynchronize itself. There were significant improvements in $F_{max}$, $EC_{50}$ and $n_H$ compared to the $HF_{sync}$ dog. Thus, paradoxically, myofilament function in otherwise synchronous heart failure can be improved by introducing a brief period of dyssynchrony. This represents a novel avenue for providing the clinically-proven benefits of CRT to patients who would not otherwise be candidates. It is contemplated that a patient with synchronous heart failure could be paced dyssynchronously at night and resynchronized during the day, or applying one for several weeks followed by the other, to yield improved function, morbidity and mortality similar to that observed in CRT responders.

Dyssynchrony is a disease punctuated with regional heterogeneity, with areas of increased and decreased stress. For this reason, it cannot be assumed that myofilament function will be identical throughout the heart. To identify the possible regional effects of dyssynchrony and CRT, function was tested in the LV lateral wall in addition to the RV. Due to the paucity of trabeculae in this region, experiments were performed on isolated skinned myocytes. While differences in this region compared to the RV were expected, none were observed. Myofilament function in the LV lateral wall in the 3 groups was identical to the RV free wall.

Regarding the myofilament results, although there are several types of PTMs known to occur to myofilament proteins, including phosphorylation (Kiuchi et al. (1993) *J. Clin. Invest.* 91:907-914; Parissis et al. (2009) *Heart Fail. Rev.* 14:265-275), acetylation (Gupta et al. (2008) *J. Biol. Chem.* 283:10135-10146), methylation (Cassidy et al. (1991) *J. Mol. Cell Cardiol.* 23:589-601), and oxidation (Avner et al. (2010) *Am. J. Physiol. Heart Circ. Physiol.* 299:H723-H730), phosphorylation is the best characterized. Treatment with the phosphatase PP1 had a differential effect on calcium sensitivity between the groups; desensitizing in control and CRT, but no change in $HF_{dys}$. This indicates that the calcium sensitizing effect of CRT is modulated by myofilament phosphorylation. The change in $F_{max}$ and $n_H$ could also be due to phosphorylation, but on proteins and residues that are not dephosphorylated by PP1. Myofilament function has been shown to be altered with phosphorylation of many sarcomeric proteins, including cardiac troponin I (cTnI; Burkart et al. (2003) *J. Biol. Chem.* 278:11265-11272 and Wang et al. (2006) *J. Mol. Cell. Cardiol.* 41:823-833), cTnT (Kooij et al. (2009) *Basic Res. Cardiol.* 105:289-300), cTnC (Biesiadecki et al. (2007) *Circ. Res.* 100:1486-1493), tropomyosin (Tm), myosin binding protein C (MyBP-C; Kooij et al. (2009) *Basic Res. Cardiol.* 105:289-300 and Bardswell et al. (2010) *J. Biol. Chem.* 285:5674-5682), myosin light chain (Colson et al. (2010) *J. Physiol.* 588: 981-993), titin (Anderson et al. (2010) *J. Struct. Biol.* 170:270-277), and others.

To explore this idea further, myofilament- and phospho-enriched samples were analyzed using an Orbitrap mass spectrometer to identify phosphorylation sites which may be present in one or more of the groups, but not all three. This would provide a list of possible candidate phosphorylation sites that could mediate the observed functional changes. Little is known about actin as a phosphoprotein and the tyrosine site is a novel phosphorylation site. Of the MyBPC sites, the S312 site, has been previously shown as a PKA substrate (Jia et al. (2010) *J. Proteome Res.* 9:1843-1853), and the T292 and S1042 sites in human tissue were also identified herein. The tropomyosin T282 site is a novel site that is in the critical head to tail overlap region of consecutive tropomyosins. This site is next to a known phosphorylation site, S282 (Wu and Saolaro (2007) *J. Biol. Chem.* 282:30691-30698). Changes in the phosphorylation pattern of cTnI between the control and $HF_{dys}$, CRT, and $HF_{sync}$ groups were also observed. However, there were no significant differences between the HF$_{dys}$, CRT, and HF$_{sync}$ groups, suggesting that the majority of these changes are due to the general effects of heart failure (which was induced in HF$_{dys}$, CRT, and HF$_{sync}$ by tachypacing). Large changes at the major PKA sites (S22/S23, which was identified by MS in all three groups) may be overshadowing small but significant changes at other sites, however, between the HF$_{dys}$, CRT, and HF$_{sync}$ groups. Taken together, the data indicate that cTnI is altered by heart failure, but is most likely not the mechanism of recovery from CRT.

TABLE 1

Representative RGS2 and RGS3 nucleic acid and amino acid sequences

Human RGS2 cDNA Sequence

SEQ ID NO: 1

```
  1 atgcaaagtg ctatgttctt ggctgttcaa cacgactgca gacccatgga caagagcgca
 61 ggcagtggcc acaagagcga ggagaagcga gaaaagatga aacggaccct tttaaaagat
121 tggaagaccc gtttgagcta cttcttacaa aattcctcta ctcctgggaa gcccaaaacc
181 ggcaaaaaaa gcaaacagca agctttcatc aagccttctc ctgaggaagc acagctgtgg
241 tcagaagcat ttgacgagct gctagccagc aaatatggtc ttgctgcatt cagggctttt
301 ttaaagtcgg aattctgtga agaaaatatt gaattctggc tggcctgtga agacttcaaa
361 aaaaccaaat caccccaaaa gctgtcctca aaagcaagga aaatatatac tgacttcata
421 gaaaaggaag ctccaaaaga gataaacata gattttcaaa ccaaaactct gattgcccag
481 aatatacaag aagctacaag tggctgcttg acaactgccc agaaaagggt atacagcttg
541 atggagaaca actcttatcc tcgtttcttg gagtcagaat tctaccagga cttgtgtaaa
601 aagccacaaa tcaccacaga gcctcatgct acatga
```

Human RGS2 Amino Acid Sequence

SEQ ID NO: 2

```
  1 mqsamflavq hdcrpmdksa gsghkseekr ekmkrtllkd wktrlsyflq nsstpgkpkt
 61 gkkskqqafi kpspeeaqlw seafdellas kyglaafraf lksefceeni efwlacedfk
121 ktkspqklss karkiytdfi ekeapkeini dfqtktliaq niqeatsgcf ttaqkrvysl
181 mennsyprfl esefyqdlck kpqittepha t
```

Mouse RGS2 cDNA Sequence

SEQ ID NO: 3

```
  1 atgcaaagtg ccatgttcct ggctgtccag cacgactgcg tacccatgga caagagtgca
 61 ggcaacggcc ccaaggtcga ggagaagcgg gagaaaatga agcggacact cttaaaggat
121 tggaagaccc gtttgagcta cttcttgcag aattcctctg ctcctgggaa gcccaaaact
181 ggcaagaaaa gcaaacagca aacttttatc aagccttctc ctgaggaagc gcagctctgg
241 gcagaagcat ttgatgaact gctggccagt aaatatgggc tggctgcatt cagggcgttt
301 ttaaagtccg agttctgtga agaaaacatt gaattctggt tggcttgtga agacttcaaa
361 aaaaccaaat caccccaaaa actgtcctca aaagcaagga aaatctatac cgacttcata
421 gagaaggaag ctcccaaaga gataaacata gacttccaaa cgaaatctct gattgcccaa
481 aatatccaag aggctacaag tggctgcttc accacagctc agaagagggt gtacagtttg
541 atggagaaca attcttatcc tcggttcttg gagtccgaat tctaccagga cttatgtaaa
601 aagccacaga tcaccacgga gccccatgct acatga
```

Mouse RGS2 Amino Acid Sequence

SEQ ID NO: 4

```
  1 mqsamflavq hdcvpmdksa gngpkveekr ekmkrtllkd wktrlsyflq nssapgkpkt
 61 gkkskqqtfi kpspeeaqlw aeafdellas kyglaafraf lksefceeni efwlacedfk
121 ktkspqklss karkiytdfi ekeapkeini dfqtksliaq niqeatsgcf ttaqkrvysl
181 mennsyprfl esefyqdlck kpqittepha t
```

Canine RGS2 cDNA Sequence

SEQ ID NO: 5

```
  1 atgaggaaac cctgcatcct tgcactccca ggacgaggat ggctctggcg catcacagtt
 61 tccacgtctt ggtgtttccc tccgtctcct cgtgaggaga gctgggactt ctctgtcctg
121 gaaggagaag caaccaagga tttcggagaa aaagctttgc aaccccacgg gaagacccaa
181 tcacgcaggt tgcgggagc aaggctgcac accctcttaa aacacggccg tcggataaag
241 tcccttctc cgcacgactg cggatccatg gacaagagct cgagcaacag ctccaagcac
301 gaggagaagc gggaaaagat gaagcggacc ctattaaaag attggaagac ccgtttgagc
361 tacttcttac aaaattcgtc gtctcctggg aagcccaaaa atggcaagaa aagcaaacag
421 caaaccttca tcaagccttc tcctgaggaa gcacagctgt ggtcagaagc gtttgatgag
481 ctgctagcca gtaaatatgg tcttgctgca ttcagggctt ttttaaaatc tgagttttgt
541 gaagaaaata ttgagttctg gctggcctgc gaagacttca aaaaaaccaa gtcaccccaa
601 aagctgtcct ccaaagcaag gaaaatatat actgatttca tagaaaaaga agcacctaaa
661 gagataaaca tagactttca aaccaaaact ctgattgccc aaaacataca agaagctaca
721 agtggctgct ttacaaccgc ccagaaaagg gtctacagct tgatggagaa caactcttat
781 cccgttcct tggagtcaga attctatcag gacttgtgta aaaagccaca gatcgccaca
841 gagcccatg ctacatga
```

Canine RGS2 Amino Acid Sequence

SEQ ID NO: 6

```
  1 mrkpcilalp grgwlwritv stswcfppsp reeswdfsvl egeatkdfge kalqphgktq
 61 srrlrgarlh tllkhgrrik slsphdcgsm dksssnsskh eekrekmkrt llkdwktrls
121 yflqnssspg kpkngkkskq qtfikpspee aqlwseafde llaskyglaa fraflksefc
181 eeniefwlac edfkktkspq klsskarkiy tdfiekeapk einidfqtkt liaqniqeat
241 sgcfttaqkr vyslmennsy prflesefyq dlckkpqiat ephat
```

TABLE 1-continued

Representative RGS2 and RGS3 nucleic acid and amino acid sequences

Human RGS3 (Isoform 1) cDNA Sequence
SEQ ID NO: 7

```
   1 atgaaccgct tcaatgggct ctgcaaggtg tgctcggagc gccgctaccg ccagatcacc
  61 atcccgaggg gaaaggacgg cttttggcttc accatctgct gcgactctcc agttcgagtc
 121 caggccgtgg attccggggg tccggcggaa cgggcaggc tgcagcagct ggacacggtg
 181 ctgcagctga atgagagggcc tgtggagcac tggaaatgtg tggagctggc ccacgagatc
 241 cggagctgcc ccagtgagat catcctactc gtgtggcgca tggtccccca ggtcaagcca
 301 ggaccagatg gcggggtcct gcggcgggcc tcctgcaagt cgacacatga cctccagtca
 361 cccccaaca aacgggagaa gaactgcacc catggggtcc aggcacggcc tgagcagcgc
 421 cacagctgcc acctggtatg tgacagctct gatgggctgc tgctcggcgg ctgggagcgc
 481 tacaccgagg tggcaagcc cgggggccag cacacccttgc ctgcactgtc ccgtgccact
 541 gcccccaccg accccaacta catcatcctg gccccgctga atcctgggag ccagctgctc
 601 cggcctgtgt accaggagga taccatcccc gaagaatcag ggagtcccag taaagggaag
 661 tcctacacag gcctggggaa gaagtcccgg ctgatgaaga cagtgcaaac catgaagggc
 721 cacgggaact accaaaactg cccggttgtg aggccgcatg ccacgcactc aagctatggc
 781 acctacgtca ccctggcccc caaagtcctg gtgttccctg tctttgttca gcctctagat
 841 ctctgtaatc ctgccgac cctcctgctg tcagaggagc tgctgctgta tgaagggagg
 901 aacaaggctg ccgaggtgac actgtttgcc tattcggacc tgctgctctt caccaaggag
 961 gacgacctg gccgctgcga cgtcctgagg aaccccctct acctccagag tgtgaagctg
1021 caggaaggtt cttcagaaga cctgaaattc tgcgtgctct atctagcaga gaaggcagag
1081 tgcttattca ctttggaagc gcactcgcag gagcagaaga gagagtgtg ctggtgcctg
1141 tcggagaaca tcgccaagca gcaacagctg gcagcatcc cccggacag caagatgttt
1201 gagacggagg cagatgagaa gagggagatg gccttggagg aagggaaggg gcctggtgcc
1261 gaggattccc cacccagcaa ggagccctct cctggccagg agcttcctcc aggacaagac
1321 cttccacca acaaggactc cccttctggg caggaacccg ctcccagcca agaaccactg
1381 tccagcaaag actcagctac ctctgaagga tcccctccag gcccagatgc tccgcccagc
1441 aaggatgtgc caccatgcca ggaaccccct ccagcccaag acctctcacc ctgccaggac
1501 ctacctgctg gtcaagaacc cctgcctcac caggaccctc tactcaccaa agacctccct
1561 gccatccagg aatccccac cgggaccctt ccaccctgtc aagatctgcc tctagccag
1621 gtctccctgc cagccaaggc ccttactgag acaccatga gctccgggga cctactagca
1681 gctactgggg acccacctgc ggcccccagg ccagccttcg tgatccctga ggtccggctg
1741 gatagcacct acagccgaaa ggcaggggca gagcagggct gctcgggaga tgaggaggat
1801 gcagaagagg ccgaggaggt ggaggagggg gaggaagggg aggaggacga ggatgaggac
1861 accagcgatg acaactacgg agagcgcagt gaggccaagc gcagcagcat gatcgagacg
1921 ggccagggg ctgagggtgg cctctcactg cgtgtgcaga actcgctgcg gcgccggacg
1981 cacagcgagg gcagcctgct gcaggagccc gagggccct gctttgcctc cgacaccacc
2041 ttgcactgct cagacggtga gggcgccgcc tccacctggg gcatgccttc gcccagcacc
2101 ctcaagaaag agctgggccg caatggtggc tccatgcacc accttttcct cttcttcaca
2161 ggacacagga gatgagcgg ggctgacacc gttggggatg atgacgaagc ctccccggaa
2221 agaaagagca aaaacctagc caaggacatg aagaacaagc tgggatcttt cagacggcgg
2281 aatgagtccc ctggagcccc tccgcgggc aaggcagaca aatgatgaa gtcattcaag
2341 cccaccctcag aggaagccct caagtgggc gagtccttgg agaagctgct ggttcacaaa
2401 tacgggttag cagtgttcca agccttcctt cgcactgagt tcagtgagga gaatctgagg
2461 ttctggttgg cttgtgagga cttcaagaag gtcaagtcac agtccaagat ggcatccaag
2521 gccaagaaga tctttgctga atacatcgcg atccaggcat gcaaggaggt caacctggac
2581 tcctacacgc gggagcacac caaggacaac ctgcagagcg tcacgcgggg ctgcttcgac
2641 ctggcacaga gcgcatctt cgggctcatg gaaaaggact cgtaccctcg ctttctccgt
2701 tctgacctct acctggacct tattaaccag aagaagatga gtccccgct ttag
```

Human RGS3 (Isoform 1) Amino Acid Sequence
SEQ ID NO: 8

```
   1 mnrfnglckv cserryrqit iprgkdgfgf ticcdspvrv qavdsggpae raglqqldtv
  61 lqlnerpveh wkcvelahei rscpseiiill vwrmvpqvkp gpdggvlrra scksthdlqs
 121 ppnkreknct hgvqarpeqr hschlvcdss dglllggwer ytevakrggq htlpalsrat
 181 aptdpnyiil aplnpgsqll rpvyqedtip eesgspskgk sytglgkksr lmktvqtmkg
 241 hgnyqncpvv rphathssyg tyvtlapkvl vfpvfvqpld lcnpartlll seelllyegr
 301 nkaaevtlfa ysdllllftke depgrcdvlr nplylqsvkl qegssedlkf cvlylaekae
 361 clftleahsq eqkkrvcwcl seniakqqql aasppdskmf eteadekrem aleegkgpga
 421 edsppskeps pgqelppgqd lppnkdspsg qepapsqepl sskdsatseg sppgpdapps
 481 kdvppcqepp paqdlspcqd lpagqeplph qdplltkdlp aiqesptrdl ppcqdlppsq
 541 vslpakalte dtmssgdlla atgdppaapr pafvipevrl dstysqkaga eqgcsgdeed
 601 aeeaeeveeg eegeededed tsddnyegers eakrssmiet gqgaegglsl rvqnslrrrt
 661 hsegsllqep rgpcfasdtt lhcsdgegaa stwgmpspst lkkelgrngg smhhlslfft
 721 ghrkmsgadt vgddddeasrk rksknlakdm knklgifrrr nespgappag kadkmmksfk
 781 ptseealkwg eslekllvhk yglavfqafl rtefseenle fwlacedfkk vksqskmask
 841 akkifaeyia iqackevnld sytrehtkdn lqsvtrgcfd laqkrifglm ekdsyprflr
 901 sdlyldlinq kkmsppl
```

Human RGS3 (Isoform 2) cDNA Sequence
SEQ ID NO: 9

```
   1 atgtttgaga cggaggcaga tgagaagagg gagatggcct tggaggaagg gaaggggcct
  61 ggtgccgagg attccccacc cagcaaggag ccctctcctg gccaggagct tcctccagga
 121 caagaccttc cacccaacaa ggactcccct tctgggcagg aacccgctcc cagccaagaa
 181 ccactgtcca gcaaagactc agctacctct gaaggatccc ctccaggccc agatgctccg
 241 cccagcaagg atgtgccacc atgccaggaa cccctccag cccaagacct ctcaccctgc
 301 caggacctac ctgctggtca agaaccctg cctcaccagg accctctact caccaaagac
 361 ctccctgcca tccaggaatc ccccaccccgg gaccttccac cctgtcaaga tctgcctcct
```

TABLE 1-continued

Representative RGS2 and RGS3 nucleic acid and amino acid sequences

```
 421 agccaggtct ccctgccagc caaggccctt actgaggaca ccatgagctc cggggaccta
 481 ctagcagcta ctggggaccc acctgcggcc cccaggccag ccttcgtgat ccctgaggtc
 541 cggctggata gcacctacag ccagaaggca ggggcagagc agggctgctc gggagatgag
 601 gaggatgcag aagaggccga ggaggtggag gaggggggagg aaggggagga ggacgaggat
 661 gaggacacca gcgatgacaa ctacggagag cgcagtgagg ccaagcgcag cagcatgatc
 721 gagacgggcc agggggctga gggtggcctc tcactgcgtg tgcagaactc gctgcggcgc
 781 cggacgcaca gcgagggcag cctgctgcag gagccccgag ggccctgctt tgcctccgac
 841 accaccttgc actgctcaga cggtgagggc gccgcctcca cctggggcat gccttcgccc
 901 agcaccctca gaaaagagct gggccgcaat ggtggctcca tgcaccacct ttccctcttc
 961 ttcacaggac acaggaagat gagcggggct gacaccgttg gggatgatga cgaagcctcc
1021 cggaagagaa agagcaaaaa cctagccaag gacatgaaga acaagctggg gatcttcaga
1081 cggcggaatg agtcccctgg agccctccc gcgggcaagg cagacaaaat gatgaagtca
1141 ttcaagccca cctcagagga agccctcaag tggggcgagt ccttggagaa gctgctggtt
1201 cacaaatacg gggttagcagt gttccaagcc ttccttcgca ctgagttcag tgaggagaat
1261 ctggagttct ggttggcttg tgaggacttc aagaaggtca agtcacagtc caagatggca
1321 tccaaggcca agaagatctt tgctgaatac atcgcgatcc aggcatgcaa ggaggtcaac
1381 ctggactcct acacgcggga gcacaccaag gacaacctgc agagcgtcac gcggggctgc
1441 ttcgacctgg cacagaagcg catcttcggg ctcatggaaa aggactcgta cccctcgcttt
1501 ctccgttctg acctctacct ggaccttatt aaccagaaga gatgagtcc cccgctttag
```

Human RGS3 (Isoform 2) Amino Acid Sequence
SEQ ID NO: 10
```
   1 mfeteadekr emaleegkgp gaedsppske pspgqelppg qdlppnkdsp sgqepapsqe
  61 plsskdsats egsppgpdap pskdvppcqe pppaqdlspc qdlpagqepl phqdplltkd
 121 lpaiqesptr dlppcqdlpp sqvslpakal tedtmssgdl laatgdppaa prpafvipev
 181 rldstysqka gaeqgcsgde edaeeaeeve egeegeeded edtsddnyge rseakrssmi
 241 etgqgaeggl slrvqnslrr rthsegsllq eprgpcfasd ttlhcsdgeg aastwgmpsp
 301 stlkkelgrn ggsmhhlslf ftghrkmsga dtvgdddeas rkrksknlak dmknklgifr
 361 rrnespgapp agkadkmmks fkptseealk wgeslekllv hkyglavfqa flrtefseen
 421 lefwlacedf kkvksqskma skakkifaey iaiqackevn ldsytrehtk dnlqsvtrgc
 481 fdlaqkrifg lmekdsyprf lrsdlyldli nqkkmsppl
```

Human RGS3 (Isoform 3) cDNA Acid Sequence
SEQ ID NO: 11
```
   1 atggagcgct ccctgcaccg cgtctccctc gggagccggc gtgcccaccc ggacttgtcc
  61 ttctacctca ccaccttttg tcagctgagg ctgtccattg atgcccagga ccgggttctg
 121 ctgcttcaca ttatagaagg taaaggcctg atcagcaaac agcctggcac ctgtgatccg
 181 tatgtgaaga tttctttgat ccctgaagat agtagactac gccaccagaa gacgcagacc
 241 gttccagact gcagagaccc ggctttccac gagcacttct tctttcctgt ccaagaggag
 301 gatgatcaga agcgtctctt ggttactgtg tggaacaggg ccagcagtc cagacagagt
 361 ggactcattg gctgcatgag ctttggggtg aagtctctcc tgactccaga caaggagatc
 421 agtggttggt actacctcct aggggagcac ctgggccgga ccaagcactt gaaggtggcc
 481 aggcggcgac tgcggccgct gagagacccg ctgctgagaa tgccaggagg tggggacact
 541 gagaatggga agaaactaaa gatcaccatc ccgaggggaa aggacggctt tggcttcacc
 601 atctgctgcg actctccagt tcgagtccag gccgtgagtt ccggggggtcc ggcggaacgg
 661 gcagggctgc agcagctgga cacggtgctg cagctgaatg agaggcctgt ggagcactgg
 721 aaatgtgtgg agctggccca cgagatccgg agctgcccca gtgagatcat cctactcgtg
 781 tggcgcatgg tccccaggt caagccagga ccagatggcg gggtcctgcg cgggcctcc
 841 tgcaagtcga cacatgacct ccagtcaccc cccaacaaac gggagaagaa ctgcacccat
 901 ggggtccagg cacggcctga gcagcgccac agctgcctgg tgtcatgtga cagctctgat
 961 gggctgctgc tcggcggctg ggagcgctac accgaggtgg ccaagcgcgg gggccagcac
1021 accctgcctg cactgtcccg tgccactgcc ccaccgacc caactacat catcctggcc
1081 ccgctgaatc ctgggagcca gctgctccgg cctgtgtacc aggaggatac catccccgaa
1141 gaatcaggga gtcccagtaa agggaagtcc tacacaggcc tggggaagaa gtcccggctg
1201 atgaaagacag tgcagaccat gaagggccac gggaactacc aaaactgccc ggttgtgagg
1261 ccgcatgcca cgcactcaag ctatggcacc tacgtcaccc tggccccaa agtcctggtg
1321 ttccctgtct tgttcagcc tctagatctc tgtaatcctg cccggaccct cctgctgtca
1381 gaggagctgc tgctatga ggggaggaac aaggctgccg aggtgacact gtttgcctat
1441 tcggacctgc tgctcttcac caaggaggac gagcctggcc gctgcgacgt cctgaggaac
1501 cccctctacc tccagagtgt gaagctgcag gaaggttctt cagaagacct gaaattctgc
1561 gtgctctatc tagcagagaa ggcagagtgc ttattcactt tggaagcgca ctcgcaggag
1621 cagaagaaga gagtgtgctg tgcctgtcg gaaacatcg ccaagcagca acagctggca
1681 gcatcacccc cggacagcaa gaaactccac cctttcggct ctctccagca ggagatgggg
1741 ccggtcaact caaccaatgc cacccaggat agaagcttta cctcaccagg acagactctg
1801 attggctga
```

Human RGS3 (Isoform 3) Amino Acid Sequence
SEQ ID NO: 12
```
   1 merslhrvsl gsrrahpdls fylttfgqlr lsidaqdrvl llhiiegkgl iskqpgtcdp
  61 yvkisliped srlrhqktqt vpdcrdpafh ehfffpvqee ddqkrllvtv wnrasqsrqs
 121 gligcmsfgv kslltpdkei sgwyyllgeh lgrtkhlkva rrrlrplrdp llrmpgggdt
 181 engkklkiti prgkdgfgft iccdspvrvq avdsggpaer aglqqldtvl qlnerpvehw
 241 kcvelaheir scpseiillv wrmvpqvkpg pdggvlrras cksthdlqsp pnkrekncth
 301 gvqarpeqrh schlvcdssd glllggwery tevakrggqh tlpalsrata ptdpnyiila
 361 plnpgsqllr pvyqedtipe esgspskgks ytglgkksrl mktvqtmkgh gnyqncpvvr
 421 phathssygt yvtlapkvlv fpvfvqpldl cnpartllls eelllyegrn kaaevtlfay
```

TABLE 1-continued

Representative RGS2 and RGS3 nucleic acid and amino acid sequences

```
481 sdlllftked epgrcdvlrn plylqsvklq egssedlkfc vlylaekaec lftleahsqe
541 qkkrvcwcls eniakqqqla asppdskklh pfgslqqemg pvnstnatqd rsftspgqtl
601 ig
```

Human RGS3 (Isoform 4) cDNA Sequence
SEQ ID NO: 13
```
  1 atgaagaaca agctggggat cttcagacgg cggaatgagt cccctggagc ccctcccgcg
 61 ggcaaggcag acaaaatgat gaagtcattc aagcccacct cagaggaagc cctcaagtgg
121 ggcgagtcct tggagaagct gctggttcac aaatacgggt tagcagtgtt ccaagccttc
181 cttcgcactg agttcagtga ggagaatctg gagttctggt tggcttgtga ggacttcaag
241 aaggtcaagt cacagtccaa gatggcatcc aaggccaaga agatctttgc tgaatacatc
301 gcgatccagg catgcaagga ggtcaacctg gactcctaca cgcgggagca caccaaggac
361 aacctgcaga gcgtcacgcg ggctgcttc gacctggcac agaagcgcat cttcgggctc
421 atggaaaagg actcgtaccc tcgctttctc cgttctgacc tctacctgga ccttattaac
481 cagaagaaga tgagtccccc gctttag
```

Human RGS3 (Isoform 4) Amino Acid Sequence
SEQ ID NO: 14
```
  1 mknklgifrr rnespgappa gkadkmmksf kptseealkw geslekllvh kyglavfqaf
 61 lrtefseenl efwlacedfk kvksqskmas kakkifaeyi aiqackevnl dsytrehtkd
121 nlqsvtrgcf dlaqkrifgl mekdsyprfl rsdlyldlin qkkmsppl
```

Human RGS3 (Isoform 5) cDNA Sequence
SEQ ID NO: 15
```
  1 atggtaacga ggaggccagt cacaaatagc tgggactggc ttcctgccgg ggcggcccca
 61 gaggctgtcc cttgcagaca catgcccctt tcacggctcc ctctcagggt tggccagaag
121 gaattttttt ttccgctcc cctcctggtc cctcccattt cctggctcct cctgtctgag
181 tcccagcccc ggcttgtgcc tgggagtcca gtcatcaggc caggattcca gagagcgtgt
241 gtggctgcag cctgcaccgt tgctgcccgc tgcccaggac gcggggtggg ggacaggagc
301 cagagtggtg cctcctacag accaatctgc ggcccaaagg tgggggccc tacagagatg
361 ctccgaggca tgtacctcac tcgcaacggg aacctgcaga ggcgacacac gatgaaggaa
421 gccaaggaca tgaagaacaa gctggggatc ttcagacggc ggaatgagtc ccctggagca
481 cctcccgcgg caaggcagac aaaatgatg aagtcattca gcccacctc agaggaagcc
541 ctcaagtggg gcgagtcctt ggagaagctg ctggttcaca aatacgggt agcagtgttc
601 caagccttcc ttcgcactga gttcagtgag gagaatctgg agttctggt ggcttgtgag
661 gacttcaaga aggtcaagtc acagtccaag atggcatcca aggccaagaa gatctttgct
721 gaatacatcg cgatccaggc atgcaaggag gtcaacctgg actcctacac gcgggagcac
781 accaaggaca acctgcagag cgtcacgcgg gctgcttcg acctggcaca gaagcgcatc
841 ttcgggctca tggaaaagga ctcgtaccct cgctttctcc gttctgacct ctacctggac
901 cttattaacc agaagaagat gagtccccg ctttag
```

Human RGS3 (Isoform 5) Amino Acid Sequence
SEQ ID NO: 16
```
  1 mvtrrpvtns wdwlpagaap eavperhmpl srlplrvgqk efffplpllv ppiswlllse
 61 sqprlvpgsp virpgfqrac vaaactvaar cpgrgvgdrs qsgasyrpic gpkvggptem
121 lrgmyltrng nlqrrhtmke akdmknklgi frrrnespga ppagkadkmm ksfkptseea
181 lkwgeslekl lvhkyglavf qaflrtefse enlefwlace dfkkvksqsk maskakkifa
241 eyiaiqacke vnldsytreh tkdnlqsvtr gcfdlaqkri fglmekdsyp rflrsdlyld
301 linqkkmspp l
```

Human RGS3 (Isoform 6) cDNA Sequence
SEQ ID NO: 17
```
  1 atgcctgtaa tcccagcact ttgggaggtt gagatgggca gatcgcaagg tcaggagatc
 61 gagaccatcc tggctaacag gtcacattca gacagcacac ctttgcccaa ttttctttct
121 ggatctcacc gtcctgagtg ttgtacctgc aggttgctca cagcctctg agcccaagat
181 agtctcccct ttgggaggag gctctacagt ggtccctggc gaagttgtga agaggtctgc
241 cacgtctctg tgctcagtgt cctctctaca tcctgtgact tgagcctgag cttgcccata
301 ttccctggct ggatggagtg gctaagccct gatatcgctc tgcccagaag agatgagtgg
361 actcaaactt ctccagccag gaagaggatc acgcatgcca aagtccaggg tgcaggtcag
421 ctgaggctgt ccattgatgc ccaggaccgg ttctgctgc ttcacattat agaaggtaaa
481 ggcctgatca gcaaacagcc tggcacctgt gatccgtatg ttaagattct tttgatcct
541 gaagatagta gactacgcca ccagaagacg cagaccgttc cagactcag agacccggct
601 ttccacgagc acttcttctt cctgtccaa gaggaggatg atcagaaacg tctcttggtt
661 actgtgtgga caggccag ccagtccaga cagagtggac tcattggctg catgagcttt
721 ggggtgaagt ctctcctgac tccagacaag gagatcagtg gttggtacta cctcctaggg
781 gagcacctgg gccgaccaa gcacttgaag gtggccaggc ggcgactgcg gccgctgaga
841 gacccgctgc tgagaatgcc aggaggtggg gacactgaga tgggaagaa actaaagatc
901 accatcccga ggggaaagga cggctttggc ttcaccatct gctgcgactc tccagttcga
961 gtccaggccg tggattccgg gggtccgggc gaacgggcag ggctgacga gctgagacg
1021 gtgctgcagc tgaatgagag gcctggagc cactggaaat gtgtggagct ggcccacgag
1081 atccggagct gccccagtga gatcatccta ctcgtgtggc gcatggtccc ccaggtcaag
1141 ccaggaccag atggcggggt cctgcggcgg gcctcctgca gtcgacaca tgacctccag
1201 tcaccccca caaacggga gaagaactgc acccatgggg tccagtacgg gcctgagcag
1261 cgccacagct gccacctggt atgtgacaga tctgatggct gctgctcgg cggctgggag
1321 cgctacaccg aggtggccaa gcgcggggcc cagcacaccc tgcctgcact gtcccgtgcc
1381 actgccccca cccgacccaa ctacatcatc ctggccccgc tgaatcctgg gagccagctg
1441 ctccggcctg tgtaccagga ggataccatc cccgaagaat cagggagtcc cagtaaaggg
1501 aagtccctaca caggcctggg gaagaagtcc cggctgatga agacagtgca gaccatgaag
```

TABLE 1-continued

Representative RGS2 and RGS3 nucleic acid and amino acid sequences

```
1561 ggccacggga actaccaaaa ctgcccggtt gtgaggccgc atgccacgca ctcaagctat
1621 ggccacctacg tcacctggc ccccaaagtc ctggtgttcc ctgtctttgt tcagcctcta
1681 gatctctgta atcctgcccg gaccctcctg ctgtcagagg actgctgct gtatgaaggg
1741 aggaacaagg ctgccgaggt gacactgttt gcctattcgg acctgctgct cttcaccaag
1801 gaggacgagc ctggccgctg cgacgtcctg aggaaccccc tctacctcca gagtgtgaag
1861 ctgcaggaag gttcttcaga agacctgaaa ttctgcgtgc tctatctagc agagaaggca
1921 gagtgcttat tcactttgga agcgcactcg caggagcaga agaagagagt gtgctggtgc
1981 ctgtcggaga acatcgccaa gcagcaacag ctggcagcat caccccccgga cagcaagatg
2041 tttgagacgg aggcagatga aagagggag atggccttgg aggaaggga ggggcctggt
2101 gccgaggatt ccccacccag caaggagccc tctcctggcc aggagcttcc tccaggacaa
2161 gaccttccac ccaacaagga ctccccttct gggcaggaag ccgctcccag ccaagaacca
2221 ctgtccagca aagactcagc tacctctgaa ggatcccctc caggcccaga tgctccgccc
2281 agcaaggatg tgccaccatg ccaggaaccc cctccagccc aagacctctc accctgccag
2341 gacctacctg ctggtcaaga acccctgcct caccaggacc ctctactcac caaagacctc
2401 cctgccatcc aggaatcccc caccgggac cttccacctt gtcaagatct gcctcctagc
2461 caggtctccc tgccagccaa ggccttact gaggacacca tgagctccgg ggacctacta
2521 gcagctactg ggacccacc tgcggcccc aggccagcct tcgtgatccc tgaggtccgg
2581 ctggatagca cctacagcca aaggcaggg gcagagcagg gctgctcggg agatgaggag
2641 gatgcagaag aggccgagga ggtggaggaa gggaggaaga cggaggatga gcaggatgag
2701 gacaccagcg atgacaacta cggagagcgc agtgaggcca agcgcagcag catgatcgag
2761 acgggccagg gggctgaggg tggcctctca ctgcgtgtgc agaactcgct gcggcgccgg
2821 acgcacagcg agggcagcct gctgcaggag cccgaggc cctgctttgc ctccgacacc
2881 accttgcact gctcagacgg tgagggcgcc gcctccacct ggggcatgcc ttcgcccagc
2941 accctcaaga aagagctggg ccgcaatggt ggctccatgc accacctttc cctcttcttc
3001 acaggacaca ggaagatgag cggggctgac accgttgggg atgatgacga agcctcccgg
3061 aagagaaaga gcaaaaacct agccaaggac atgaagaaca agctggggat cttcagacgg
3121 cggaatgagt cccctggagc ccctccgcg ggcaaggcag acaaaatgat gaagtcattc
3181 aagcccacct cagaggaagc cctcaagtgg ggcgagtcct tggagaagct gctggttcac
3241 aaatacgggt tagcagtgtt ccaagcctc cttcgcactg agttcagtga ggagaatctg
3301 gagttctggt tggcttgtga ggacttcaag aaggtcaagt cacagtccaa gatggcatcc
3361 aaggccaaga agatctttgc tgaatacatc gcgatccagg catgcaagga ggtcaacctg
3421 gactcctaca cgcggggaca caccaaggac aacctgcagg tcgtcacgcg gggctgcttc
3481 gacctggcac agaagcgcat cttcgggctc atggaaaagg actcgtaccc tcgctttctc
3541 cgttctgacc tctacctgga ccttattaac cagaagaaga tgagtccccc gctttag
```

Human RGS3 (Isoform 6) Amino Acid Sequence
SEQ ID NO: 18
```
   1 mpvipalwev emgrsqggei etilanrshs dstplpnfls gshrpecctc rlltasgaqd
  61 slpfgrrlys gpwrsceevc hvsvlsvlst scglslslpi fpgwmewlsp dialprrdew
 121 tqtsparkri thakvqgagq lrlsidaqdr vllhiiegk gliskqpgtc dpyvkislip
 181 edsrlrhqkt qtvpdcrdpa fhehfffpvq eeddqkrllv twnrasqsr qsgligcmsf
 241 gvkslltpdk eisgwyyllg ehlgrtkhlk varrrlrplr dpllrmpggg dtengkklki
 301 tiprgkdgfg fticcdspvr vqavdsggpa eraglqqldt vlqlnerpve hwkcvelahe
 361 irscpseiil lvwrmvpqvk pgpdggvlrr asckssthdlq sppnkreknc thgvqarpeq
 421 rhschlvcds sdglllggwe rytevakrgg qhtlpalsra taptdpnyii laplnpgsql
 481 lrpvyqedti peesgspskg ksytglgkks rlmktvqtmk ghgnyqncpv vrphathssy
 541 gtyvtlapkv lvfpvfvqpl dlcnpartll lseelllyeg rnkaaevtlf aysdllllftk
 601 edepgrcdvl rnplylqsvk lqegssedlk fcvlylaeka eclftleahs qeqkkrvcwc
 661 lseniakqqq laasppdskm feteadekre maleegkgpg aedsppskep spgqelppgq
 721 dlppnkdsps gqepapsqep lsskdsatse gsppgpdapp skdvppcqep ppaqdlspcq
 781 dlpagqeplp hqdplltkdl paiqesptrd lppcqdlpps qvslpakalt edtmssgdll
 841 aatgdppaap rpafvipevr ldstysqkag aeqgcsgdee daeeaeevee geegeedede
 901 dtsddnyger seakrssmie tgqqaeggls lrvqnslrrr thsegsllqe prgpcfasdt
 961 tlhcsdgega astwgmpsps tlkkelgrng gsmhhlslff tghrkmsgad tvgdddeasr
1021 krksknlakd mknklgifrr rnespgappa gkadkmmksf kptseealkw geslekllvh
1081 kyglavfqaf lrtefseenl efwlacedfk kvksqskmas kakkifaeyi aiqackevnl
1141 dsytrehtkd nlqsvtrgcf dlaqkrifgl mekdsyprfl rsdlyldlin qkkmspppl
```

Mouse RGS3 (Isoform 1) cDNA Sequence
SEQ ID NO: 19
```
   1 atggagaggc cacatcagga tgcttccttg tccaaaaaag atgcctgcac ccagacttac
  61 ccacctagga ggaggatcag gcatgcccaa gtgcaggatg caggtcaact gaagctgtcc
 121 attgatgccc aggatcgggt tctgctgctg cacatcatag aaggcaaagg cctgatgagc
 181 agggagcctg gcatctgcga tccctatgtg aaggtttctt tgatcccaga agacagccag
 241 ctcccctgcc agaccacaca gatcattcca gactgccgag acccagcttt ccacgagcac
 301 ttcttcttc ctgtcccaga ggagggtgat cagaagcgtc ttctggtgac agtgtggaac
 361 cgggccagtg agaccaggca gcatacgctt attggctgca tgagctttgg ggtgaggtct
 421 ctcttgactc cggacaagga gatcagtggc tggtactatc tgctagggga ggacctgggt
 481 cggaccaagc acctcaaggt ggctaggcgg cggctccgac ccctgagaga catgctgttg
 541 agaatgccag gagagggga ccctgagaac gggagaaac tccagatcac catcccggagg
 601 ggcaaagacg gctttggctt caccatctgc tgtgactctc cggtccgagt ccaggctgtg
 661 gattctgggg gcccggcaga gagggcggga ctgcagcagc tggacacagt gctacaactg
 721 aatgagagac ccgtggagca ctggaaatgt gtggagctgg cacatgagat ccggagctgt
 781 cctagcgaga tcatcctgct cgtgtggcgt gtggtccccc agatcaagcc ggggcagat
 841 ggcggagtct tgcggcgggc ctcctgcaag tccacacatg acctcctgtc ccccctaac
 901 aagagggaga agaactgtac tcatggggcc ccagttcgtc ctgagcagcg ccacagctgc
 961 cacctggtgt gtgacagctc tgatggtcta ctgcttggtg gctggggcg ctacactgag
1021 gtgggcaagc gcagtggcca gcacaccctg cctgcactgt cccggaccac caccccctact
```

TABLE 1-continued

Representative RGS2 and RGS3 nucleic acid and amino acid sequences

```
1081 gaccccaact acatcatcct ggccccactg aatcctggaa gccagttgct gcggcctgtg
1141 taccaggagg atacaatccc tgaagaaccg gggactacta ctaaaggaa atcgtacacc
1201 ggcctgggca agaagtctcg gctcatgaag acagtgcaga ccatgaaggg ccacagtaac
1261 taccaagact gctcagccct gagaccgcac atcccgcatt ccagttacgg cacctatgtc
1321 accctggccc ctaaagtcct ggtgttccct gtctttgtgc agccctaga tctctgtaac
1381 cctgcccgga ctctcctgct gtcggaggag ctgctgctgt atgagggag gaacaagact
1441 tcccaggtga cactgtttgc ctactcggac ctgctgctgt tcactaagga ggaggagcca
1501 ggccgctgcg acgtcctgag aaatccctc tacctccaga gcgtgaagct acaggagggc
1561 tcttcagaag acttgaaatt ctgtgtgctg tacctggcag agaaggcaga gtgcttattc
1621 actttggagg cacactcgca ggagcagaag aagagagtgt gctggtgcct gtcggagaac
1681 atcgccaagc agcaacagct ggccgcacca cctacagaga ggaagaaact tcacccttac
1741 ggctctctcc agcaggagat ggggccagtc acctccatca gtgccaccca ggatagaagc
1801 tttacctcat caggacagac cctgattggc tga
```

Mouse RGS3 (Isoform 1) Amino Acid Sequence

SEQ ID NO: 20
```
  1 merphqdasl skkdactqty pprrrirhaq vqdagqlkls idaqdrvlll hiiegkglms
 61 repgicdpyv kvslipedsq lpcqttqiip dcrdpafheh fffpvpeegd qkrllvtvwn
121 rasetrqhtl igcmsfgvrs lltpdkeisg wyyllgedlg rtkhlkvarr rlqplrdmll
181 rmpgegdpen geklqitirr gkdgfgftic cdspvrvqav dsggpaerag lqqldtvlql
241 nerpvehwkc velaheirsc pseiillvwr vvpqikpgpd ggvlrrassck sthdllsppn
301 kreknctghga pvrpeqrhsc hlvcdssdgl llggweryte vgkrsgqhtl palsrttpt
361 dpnyiilapl npgsqllrpv yqedtipeep gtttkgksyt glgkksrlmk tvqtmkghsn
421 yqdcsalrph iphssygtyv tlapkvlvfp vfvqpldlcn partlllsee lllyegrnkt
481 sqvtlfaysd llllftkeeep grcdvlrnpl ylqsvklqeg ssedlkfcvl ylaekaeclf
541 tleahsqeqk krvcwclsen iakqqqlaap pterkklhpy gslqqemgpv tsisatqdrs
601 ftssgqtlig
```

Mouse RGS3 (Isoform 2) cDNA Sequence

SEQ ID NO: 21
```
   1 atgaaccgct tcaatgggct ctgcaaagtg tgttcagaac gccgctaccg cagatcacc
  61 atccggaggg gcaaagacgg cttttgcttc accatctgct gtgactctcc ggtccgagtc
 121 caggctgtgg attctggggg cccggcagag agggcgggac tgcagcagct ggacacagtg
 181 ctacaactga atgagagacc cgtggagcac tggaaatgtg tggagctggc acatgagatc
 241 cggagctgtc ctagcgagat catcctgctc gtgtggcgtg tggtccccca gatcaagccg
 301 ggccagatg gcggagtctt gcggcgggcc tcctgcaagt ccacacatga cctcctgtca
 361 cccctaaca agagggagaa gaactgtact catggggccc cagttcgtc tgagcagcgc
 421 cacagctgcc acctggtgtg tgacagtct gatggtctac tgcttggtgg ctgggagcgc
 481 tacactgagg tgggcaagcg cagtggccag cacaccctgc ctgcactgtc ccggaccacc
 541 accccctactg accccaacta catcatcctg gccccactga atcctggaag ccagttgctg
 601 cggcctgtgt accaggagga tacaatccct gaagaaccgg ggactactac taaagggaaa
 661 tcgtacaccg gcctgggcaa gaagtctcgg ctcatgaaga cagtgcagac catgaagggc
 721 cacagtaact accaagactg ctcagccctg agaccgcaca tcccgcattc cagttacggc
 781 acctatgtca ccctggcccc taaagtcctg gtgttccctg tctttgtgca gccctagat
 841 ctctgtaacc ctgcccggac tctcctgctg tcggaggagc tgctgctgta tgagggagg
 901 aacaagactt cccaggtgac actgtttgcc tactcggacc tgctgctgtt cactaaggag
 961 gaggagccag gccgctgcga cgtcctgaga aatcccctct acctccagag cgtgaagcta
1021 caggagggct cttcagaaga cttgaaattc tgtgtgctgt acctggcaga gaaggcagag
1081 tgcttattca ctttggaggc acactcgcag gagcagaaga agagagtgtg ctggtgcctg
1141 tcggagaaca tcgccaagca gcaacagctg gccgcaccac ctacagagag gaagatgttt
1201 gagacagagg cagatgagaa ggagatgccc ctggtcgagg ggaaggggcc aggtgctgag
1261 gaacccgcac ccagcaaaaa tccctctcct ggccaggagc ttcctccagg acaagacctc
1321 cctcccagca aagaccctc tcccagccag gagcttcctg caggacaaga tctccctccc
1381 agcaaagacc cctctcccag ccaggagctt cctgcaggac aagatctccc tcccagcaaa
1441 gacccctctc ccagccagga gcttcctgta ggacaagacc tcccacccag gaagactcc
1501 tcaggccaag aagctgctcc tggcccagaa tcaccatcca gtgaagacat agcaacctgc
1561 cctaagcccc ctcaaagccc agaaacctca acaagcaagg actccccacc aggccaggga
1621 tcctccccga ccacagaact cccatcttgc cagggccttc ctgctggtca agaatctact
1681 agccaggacc ctctgctcag tcaagagccc cctgttatcc agaatcctc tgcctccgtc
1741 cagaaacgcc taccctctca ggagtcaccc tccagcctgg gctccctgcc agagaaggac
1801 cttgctgagc agaccatcag ctccggggag ccaccagtgc ccactggtgc tgtactgcca
1861 gcctctagac ctaactttgt gatccccgag gtgcgtctgg ataatgccta cagccaactg
1921 gatggggccc acggaggcag ctctggcgag gacgaggatg cagaagaggg agaggagggg
1981 ggagaagggg aggaagatga ggaggacgac accagcgacg acaactacgg ggatcgtagt
2041 gaggccaagc gcagcagcct gattgagact ggccaaggcg ccgagggcgg cttctcgttg
2101 cgtgtgcaga actcgctcg gcgccggacg cacagcggac cagcctgct gcaggagtcc
2161 cggggggccct gctttgcctc tgacaccacc ttacactgct ctgatgcgca gggcgccaca
2221 tccacctggg ctatcccttc accccgcacc ctcaaaaaag aactgggtcg taatgaggc
2281 tccatgcacc acctttcct gttcttcacg gacacagga agatgagtgg gactgacctc
2341 acagaatgtg atgaagcttc ccggaagaga aagcaaaa acatagccaa ggacatgaag
2401 aataagctgg ccatcttcag gcggcggaac gaatctcagcc gggctcagcc agccagcaag
2461 acagacaaga caaccaagtc cttcaagcct acctcggagg aagccctcaa gtggagcgag
2521 tccctggaaa agttgctgct tcataaatat ggcttagaag tgttccaggc cttcctgcgc
2581 accgagttca gtgaggagaa cctggagttt tggctcgctt gcgaggactt caagaaggtc
2641 aaatcacagt ccaagatggc agccaaagcc aagaagatct ttgctgaatt catcgcaatc
2701 caggcttgca aagaggtaaa cctggactcc tacacacgag aacacaccaa ggagaatctg
```

TABLE 1-continued

Representative RGS2 and RGS3 nucleic acid and amino acid sequences

```
2761 cagagcatca cccgaggctg ctttgacttg gcacagaaac gtatctttgg gctcatggag
2821 aaggactctt accctcgctt cctccgctct gacctctacc tggacctcat taaccagaag
2881 aagatgagtc ccccgctcta g
```

Mouse RGS3 (Isoform 2) Amino Acid Sequence
SEQ ID NO: 22
```
  1 mnrfnglckv cserryrqit irrgkdgfgf ticcdspvrv qavdsggpae raglqqldtv
 61 lqlnerpveh wkcvelahei rscpseiill vwrvvpqikp gpdggvlrra scksthdlls
121 ppnkreknct hgapvrpeqr hschlvcdss dglllggwer ytevgkrsgq htlpalsrtt
181 tptdpnyiil aplnpgsqll rpvyqedtip eepgtttkgk sytglgkksr lmktvqtmkg
241 hsnyqdcsal rphiphssyg tyvtlapkvl vfpvfvqpld lcnpartlll seelllyegr
301 nktsqvtlfa ysdllllftke eepgrcdvlr nplylqsvkl qegssedlkf cvlylaekae
361 clftleahsq eqkkrvcwcl seniakqqql aappterkmf eteadekemp lvegkgpgae
421 epapsknpsp gqelppgqdl ppskdpspsq elpagqdlpp skdpspsqel pagqdlppsk
481 dpspsqelpv gqdlpprkds sgqeaapgpe spssediatc pkppqspets tskdsppgqg
541 sspttelpsc qglpagqest sqdpllsqep pvipessasv qkrlpsqesp sslgslpekd
601 laeqtissge ppvatgavlp asrpnfvipe vrldnaysql dgahggssge dedaeeegeeg
661 gegeedeedd tsddnygdrs eakrsslliet gqgaeggfsl rvqnslrrrt hsegsllqes
721 rgpcfasdtt lhcsdgegat stwaipsprt lkkelgrngg smhhlslffft ghrkmsgtdl
781 tecdeasrkr kskniakdmk nklaifrrrn espgaqpask tdkttksfkp tseealkwse
841 slekllhhky glevfqaflr tefseenlef wlacedfkkv ksqskmaaka kkifaefiai
901 qackevnlds ytrehtkenl qsitrgcfdl aqkrifglme kdsyprflrs dlyldlinqk
961 kmsppl
```

Mouse RGS3 (Isoform 3) cDNA Sequence
SEQ ID NO: 23
```
  1 atgaaccgct tcaatgggct ctgcaaagtg tgttcagaac gccgctaccg gcagatccag
 61 atccggaggg gcaaagacgg ctttggcttc accatctgct gtgactctcc ggtccgagtc
121 caggctgtgg attctggggg cccggcagag agggcgggac tgcagcagct ggacacagtg
181 ctacaactga atgagagacc cgtggagcac tggaaatgtg tggagctggc acatgagatc
241 cggagctgtc ctagcgagat catcctgctc gtgtggcgtg tggtccccca gatcaagccg
301 gggccagatg gcggagtctt gcggcgggcc tcctgcaagt ccacacatga cctcctgtca
361 ccccctaaca agagggagaa gaactgtact catggggccc cagttcgtcc tgagcagcgc
421 cacagctgcc acctggtgtg tgacagctct gatggtctac tgcttggtgg ctgggagcgc
481 tacactgagg tgggcaagcg cagtggccag cacaccctgc ctgcactgtc ccggaccacc
541 accccctactg accccaacta catcatcctg gccccactga atcctggaag ccagttgctg
601 cggcctgtgt accaggagga tacaatccct gaagaaccgg ggactactac taaagggaaa
661 tcgtacaccg gcctgggcaa gaagtctcgg ctcatgaaga cagtgcagac catgaagggc
721 cacagtaact accaagactg ctcagccctg agaccgcaca tcccgcattc agttacggc
781 acctatgtca ccctggcccc taaagtcctg gtgttccctg tctttgtgca gcccctagat
841 ctctgtaacc ctgcccggac tctcctgctg tcggaggagc tgctgctgta tgagggggag
901 aacaagactt cccaggtgac actgtttgcc tactcggacc tgctgctgtt cactaaggag
961 gaggagccag gccgctgcga cgtcctgaga atcccctct acctccagag cgtgaagcta
1021 caggagggct cttcagaaga cttgaaattc tgtgtgctgt acctggcaga gaaggcagag
1081 tgcttattca ctttggaggc acactcgcag gagcagaaga gagagtgtg ctggtgcctg
1141 tcggagaaca tcgccaagca gcaaacagctg gccgcaccac ctacagagag gaagaaactt
1201 caccccttacg gctctctcca gcaggagatg gggccagtca cctccatcag tgccacccag
1261 gatagaagct ttacctcatc aggacagacc ctgattggct ga
```

Mouse RGS3 (Isoform 3) Amino Acid Sequence
SEQ ID NO: 24
```
  1 mnrfnglckv cserryrqit irrgkdgfgf ticcdspvrv qavdsggpae raglqqldtv
 61 lqlnerpveh wkcvelahei rscpseiill vwrvvpqikp gpdggvlrra scksthdlls
121 ppnkreknct hgapvrpeqr hschlvcdss dglllggwer ytevgkrsgq htlpalsrtt
181 tptdpnyiil aplnpgsqll rpvyqedtip eepgtttkgk sytglgkksr lmktyqtmkg
241 hsnyqdcsal rphiphssyg tyvtlapkvl vfpvfvqpld lcnpartlll seelllyegr
301 nktsqvtlfa ysdllllftke eepgrcdvlr nplylqsvkl qegssedlkf cvlylaekae
361 clftleahsq eqkkrvcwcl seniakqqql aappterkkl hpygslqqem gpvtsisatq
421 drsftssgqt lig
```

Canine RGS3 cDNA Sequence
SEQ ID NO: 25
```
  1 atgcagcgct ccctgcaccg cgtggccctc gggagccggc gcgcccgccc cggcctgtcc
 61 ttctacctcg ccaccttcgg tcagctgaag ctgtcgatcg atgcccggga ccggggttctg
121 ctgctccaca tcatagaagg caaaggcctg atgagcagag agcctggcat ctgtgatccc
181 tacgtgaaga tttctttgat cccagaagat aatcgactac gtcgccagaa gacgcagacg
241 gtcccagact gcagagagcc agtcttccac gagcacttct ttttttcctgt ccaagaggaa
301 gatgaacaga agcgcctttct ggtcactgtg tggaataggg caggtgactc caggcagagt
361 ggactcattg gctgcatgag ctttggggtg aagtccctcc tgactccgga caagaaatc
421 agtggctggt actaccttct gggggaagac ctgggccgga ctaaacacct gaaggtgcc
481 aggcggcggc tgcggcccct gagagacccg ctgctgagaa caccaggatg tggggatgct
541 gagaacgggg agaaactcaa gatcaccatc ccgaggggga aggacggctt tggcttcacc
601 atctgctgtg actctccggt tcgagtccaa gctgtggatt ctggaggtcc agcggagcgg
661 gcagggctgc agcagctgga caccgtgctg cagctgaacg agaggcccgt ggagcactgg
721 aaatgcgtgg agctggccca tgagatccgg agctgcccca gtgagatcat cctgcttgtg
781 tggcgcatgg tccccaggt caagccaggg ccggacggcg gggtcctgcg gcgggcctcc
841 tgcaagtcga cacatgacct ccagtcaccc cccaataagc gggagaagaa ttgcacccac
901 ggggcccagg cacggcccga gcagcgccac agctgccacc tggtgtgtga cagctcagat
```

TABLE 1-continued

Representative RGS2 and RGS3 nucleic acid and amino acid sequences

```
 961 gggctgctgc tcggcggctg ggaacgctac accgaggtgg ccaagcgtgg gggccagcat
1021 accctgcctg cgctgtcccg ggccacggcc tccacggacc ccaactacat catcttggcc
1081 ccattgaacc ccgggagcca gctgctgcga cctgtgtacc aagaggatgc catccccgaa
1141 gaatcaggta gtcccagtaa agggaagtcc tacacgggcc tggggaagaa gtcccggctg
1201 atgaaaacag tgcagaccat gaagggccac gggaactacc agaactgccc ggtcatgagg
1261 ccgcatgccc cacactcaag ctatggcacc tacgtcaccc tggcccccaa agtcctcgtg
1321 tttccagtct ttgttcagcc tttagatctc tgtaaccctg cccggacact cctgttgtct
1381 gaggagctgc tgctgtacga ggggaggaac aaggctgtgg aggtgacgct gtttgcctac
1441 tcggacctgc tgctcttcac caaggaagat gagccgggac gctgcaacgt cctgaggaac
1501 cccctctacc tccagagcgt gaagctgcag gaaggttctt cagaagacct gaaattctgt
1561 gtgctgtacc tagcagagaa ggcagagtgc ttattcactt tggaagcgca ctcgcaggag
1621 cagaagaaga gagtgtgctg gtgcctgtcg gagaacatcg ccaagcagca acagctggcc
1681 gcttcgcccc tggagagcaa gaaactccac ccttatggct ctctccagca ggagatgggg
1741 ccggccaact caaccaatgc tacccaggat agaagcttta cctcatcagg acagactctg
1801 attggctga
```

Canine RGS3 Amino Acid Sequence

SEQ ID NO: 26

```
  1 mqrslhrval gsrrarpgls fylatfgqlk lsidardrvl llhiiegkgl msrepgicdp
 61 yvkisliped nrlrrqktqt vpdcrepvfh ehfffpvqee deqkrllvtv wnragdsrqs
121 gligcmsfgv kslltpdkei sgwyyllged lgrtkhlkva rrrlrplrdp llrtpgcgda
181 engeklkiti prgkdgfgft iccdspvrvq avdsggpaer agiqqldtvl qlnerpvehw
241 kcvelaheir scpseiillv wrmvpqvkpg pdggvlrras cksthdlgsp pnkrekncth
301 gaqarpeqrh schlvcdssd glllggwery tevakrggqh tlpalsrata stdpnyiila
361 plnpgsqllr pvyqedaipe esgspskgks ytglgkksrl mktvqtmkgh gnyqncpvmr
421 phaphssygt yvtlapkvlv fpvfvqpldl cnpartllls eelllyegrn kavevtlfay
481 sdlllftked epgrcnvlrn plylqsvklq egssedlkfc vlylaekaec lftleahsqe
541 qkkrvcwcls eniakqqqla aspleskklh pygslqqemg panstnatqd rsftssgqtl
601 ig
```

TABLE 2

Phosphorylation sites of myofilament phosphorylated proteins in canine pacing models

| Protein | Site | Control | HF$_{dys}$ | CRT |
|---|---|---|---|---|
| Actin | Y241 | | ✓ | |
| MyBPC | T292 | | | ✓ |
| MyBPC | S312 | ✓ | | ✓ |
| MyBPC | S1042 | | ✓ | |
| Tm | T282 | | | ✓ |

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating heart failure, comprising:
induction dyssynchronous contractions of a ventricle in a subject suffering from heart failure, wherein at least part of the ventricle contracts dyssynchronously relative to another part of the subject's ventricle, wherein the dyssynchronous contractions are induced using a device, comprising:
a power source;
an atrial stimulation electrode operably connected to an atrium of the subject's heart;
a ventricular stimulation electrode operably connected to the ventricle of the subject's heart; and
a controller that is:
operably connected to the power source and to the stimulation electrodes;
configured to receive a signal indicative of atrial electrical activity; and
programmed to:
monitor the signal to detect an atrial heart rate;
operate the device in a normal pacing mode, for which the controller is programmed to cause the atrial stimulation electrode to depolarize atrial tissue of the subject if the atrial heart rate is below a predetermined limit; and
periodically transiently operate the device in a dyssynchrony-inducing mode, for which the controller is programmed to cause the ventricular stimulation electrode to depolarize ventricular tissue of the subject at a single site with a delay relative to atrial electrical activity shorter than a normal atrioventricular conduction delay; alternate between the normal pacing mode and the dyssynchrony-inducing mode in a cycle; and have a cycle length of at least one month; or
operate the device in a dyssynchrony-inducing mode, for which the controller is programmed to cause the ventricular stimulation electrode to depolarize ventricular tissue of the subject at a single site with a delay relative to atrial electrical activity shorter than a normal atrioventricular conduction delay; and
periodically apply the dyssynchrony-inducing mode for a period of time of at least a few hours sufficient to stimulate molecular signaling changes that are subsequently modified by reinstating normal pacing;
periodically transiently operating the device in the dyssynchrony-inducing mode to cause the ventricular stimulation electrode to depolarize the ventricular tissue of the subject at the single site with the delay relative to atrial electrical activity shorter than the normal atrioventricular conduction delay;
maintaining the dyssynchronous contractions for a period of time;
alternating between the normal pacing mode and the dyssynchrony-inducing mode in the cycle, wherein the cycle length is of at least the one month; and
restoring synchronous contractions of the subject's ventricle.

2. A method of treating heart failure, comprising:
induction dyssynchronous contractions of a ventricle in a subject suffering from heart failure, wherein at least part of the ventricle contracts dyssynchronously relative to another part of the subject's ventricle, wherein the dyssynchronous contractions are induced using a device, comprising:
a power source;
an atrial stimulation electrode operably connected to an atrium of the subject's heart;
a ventricular stimulation electrode operably connected to the ventricle of the subject's heart; and
a controller that is:
operably connected to the power source and to the stimulation electrodes;
configured to receive a signal indicative of atrial electrical activity; and
programmed to:
monitor the signal to detect an atrial heart rate;
operate the device in a normal pacing mode, for which the controller is programmed to cause the atrial stimulation electrode to depolarize atrial tissue of the subject if the atrial heart rate is below a predetermined limit; and
periodically transiently operate the device in a dyssynchrony-inducing mode, for which the controller is programmed to cause the ventricular stimulation electrode to depolarize ventricular tissue of the subject at a single site with a delay relative to atrial electrical activity shorter than a normal atrioventricular conduction delay;
alternate between the normal pacing mode and the dyssynchrony-inducing mode in a cycle; and have a cycle length of at least one month;
maintaining the dyssynchronous contractions for a period of time; and
restoring synchronous contractions of the subject's ventricle.

3. The method of claim 2, wherein dyssynchronous contractions are induced by periodically applying ventricular pacing to the subject.

4. The method of claim 3, wherein the ventricular pacing is timed to the subject's atrial electrical activity and applied with a delay relative to the atrial electrical activity that is shorter than a normal atrioventricular conduction delay, thereby causing at least part of the subject's ventricle to contract dyssynchronously relative to another part of the subject's ventricle that is stimulated to contract by normal atrioventricular conduction.

5. The method of claim 4, wherein the ventricular pacing is applied at no more than one site.

6. The method of claim 5, wherein the one site is a left-ventricular site.

7. The method of claim 5, wherein the one site is a right-ventricular site.

8. The method of claim 3, wherein non-ventricular pacing is applied when the ventricular pacing is not being applied.

9. The method of claim 2, wherein induced dyssynchronous contractions are maintained for a period of time of at least a few hours sufficient to stimulate molecular signaling changes that are subsequently modified by restoring synchronous contractions.

10. The method of claim 2, further comprising alternating between induced dyssynchronous contractions and restored synchronous contractions to provide repeated periods of resynchronization following induced dyssynchrony.

11. The method of claim 2, wherein induced dyssynchronous contractions are maintained during nighttime, and restored synchronous contractions are maintained for the rest of each day.

12. The method of claim 2, comprising monitoring the signal to detect the atrial heart rate.

13. The method of claim 2, comprising operating the device in a normal pacing mode to cause the atrial stimulation electrode to depolarize the atrial tissue of the subject if the atrial heart rate is below the predetermined limit.

14. The method of claim 2, comprising:
periodically transiently operating the device in the dyssynchrony-inducing mode to cause the ventricular stimulation electrode to depolarize the ventricular tissue of the subject at the single site with the delay relative to atrial electrical activity shorter than the normal atrioventricular conduction delay; and,
alternating between the normal pacing mode and the dyssynchrony-inducing mode in the cycle, wherein the cycle length is of at least the one month.

15. The method of claim 2, comprising:
operating the device in the dyssynchrony-inducing mode to cause the ventricular stimulation electrode to depolarize the ventricular tissue of the subject at the single site with the delay relative to atrial electrical activity shorter than the normal atrioventricular conduction delay; and,
periodically applying the dyssynchrony-inducing mode for the period of time of at least the few hours sufficient to stimulate the molecular signaling changes that are subsequently modified by reinstating the normal pacing.

16. A method of treating heart failure, comprising:
inducing dyssynchronous contractions of a ventricle in a subject suffering from heart failure, wherein at least part of the ventricle contracts dyssynchronously relative to another part of the subject's ventricle, wherein the dyssynchronous contractions are induced using a device, comprising:
a power source;
an atrial stimulation electrode operably connected to an atrium of the subject's heart;
a ventricular stimulation electrode operably connected to the ventricle of the subject's heart; and
a controller that is:
operably connected to the power source and to the stimulation electrodes;
configured to receive a signal indicative of atrial electrical activity; and
programmed to:
monitor the signal to detect an atrial heart rate;
operate the device in a dyssynchrony-inducing mode, for which the controller is programmed to cause the ventricular stimulation electrode to depolarize ventricular tissue of the subject at a single site with a delay relative to atrial electrical activity shorter than a normal atrioventricular conduction delay; and
periodically apply the dyssynchrony-inducing mode for a period of time of at least a few hours sufficient to stimulate molecular signaling changes that are subsequently modified by reinstating normal pacing;
periodically transiently operating the device in the dyssynchrony-inducing mode to cause the ventricular stimulation electrode to depolarize the ventricular tissue of the subject at the single site with the delay relative to atrial electrical activity shorter than the normal atrioventricular conduction delay;
maintaining the dyssynchronous contractions for a period of time;
alternating between the normal pacing mode and the dyssynchrony-inducing mode in the cycle, wherein the cycle length is of at least the one month; and
restoring synchronous contractions of the subject's ventricle.

\* \* \* \* \*

UNITED STATES PATENT AND TRADEMARK OFFICE
CERTIFICATE OF CORRECTION

PATENT NO. : 10,525,269 B2
APPLICATION NO. : 15/359041
DATED : January 7, 2020
INVENTOR(S) : David Kass, Gordon Tomaselli and Jonathan Kirk Page 1 of 1

It is certified that error appears in the above-identified patent and that said Letters Patent is hereby corrected as shown below:

In the Specification

Column 1, Line 21, delete "Grants PO1- HL077180 , RO1-HL-089297, T32-HL0072, RO1-DK073368, DP1 OD006419, F31-GM087079, RO1-GM085058, RO1-HL-053432AI93256, AI67854, and AI24755", and insert therefor --HL077180 and HL007227--.

Signed and Sealed this
Fifth Day of May, 2020

Andrei Iancu
*Director of the United States Patent and Trademark Office*